United States Patent
Yamamoto

(10) Patent No.: US 7,487,052 B2
(45) Date of Patent: *Feb. 3, 2009

(54) STATE DETECTION DEVICE

(75) Inventor: Tomoshige Yamamoto, Tokyo (JP)

(73) Assignee: Yamatake Corporation, Tokyo (JP)

( * ) Notice: Subject to any disclaimer, the term of this patent is extended or adjusted under 35 U.S.C. 154(b) by 6 days.

This patent is subject to a terminal disclaimer.

(21) Appl. No.: 11/662,306

(22) PCT Filed: Sep. 21, 2005

(86) PCT No.: PCT/JP2005/017409

§ 371 (c)(1),
(2), (4) Date: Mar. 8, 2007

(87) PCT Pub. No.: WO2006/033365

PCT Pub. Date: Mar. 30, 2006

(65) Prior Publication Data

US 2008/0028867 A1    Feb. 7, 2008

(30) Foreign Application Priority Data

Sep. 22, 2004    (JP) .......................... 2004-275249

(51) Int. Cl.
*G06F 19/00* (2006.01)
*G01N 11/00* (2006.01)
*G01L 7/00* (2006.01)

(52) U.S. Cl. .................. 702/50; 702/38; 702/100; 73/1.16; 73/700; 73/861.12

(58) Field of Classification Search ............ 702/38, 702/45, 50, 100; 73/861.12, 861.16, 861.17, 73/700, 735, 1.16

See application file for complete search history.

(56) References Cited

U.S. PATENT DOCUMENTS 4,408,497 A * 10/1983 Suzuki .................. 73/861.17

(Continued)

FOREIGN PATENT DOCUMENTS

JP    06-241855 A    9/1994
JP    2004-108973 A    4/2004

(Continued)

OTHER PUBLICATIONS

JNMIHF edition, "Flow Rate Measurement A to Z for Instrumentation Engineers", Kogyo Gijutusha, 1995, pp. 147-148.

*Primary Examiner*—Edward Raymond
*Assistant Examiner*—Elias Desta
(74) *Attorney, Agent, or Firm*—Blakely, Sokoloff, Taylor & Zafman LLP

(57) ABSTRACT

An exciting unit, applies, to a fluid, a time-changing magnetic field asymmetrical to a plane (PLN). An electrode is placed on the plane in a measuring tube, and detects a resultant electromotive force of an electromotive force based on $\partial A/\partial t$ component (A: vector potential, t: time) irrelevant to a flow velocity of the fluid and an electromotive force based on a v×B component originating from the flow velocity of the fluid. A state quantifying unit extracts the $\partial A/\partial t$ component and a variation factor dependent on a parameter to be detected, and quantifies the parameter on the basis of the variation factor. The characteristic and state of the fluid and the state in the measuring tube can be detected regardless of the flow rate of the fluid by using the same hardware arrangement as that of an electromagnetic induction type flowmeter.

15 Claims, 29 Drawing Sheets

U.S. PATENT DOCUMENTS 4,726,236 A * 2/1988 Wada .................. 73/861.16
5,625,155 A * 4/1997 Yoshida ................ 73/861.11
7,369,949 B2 * 5/2008 Yamamoto .............. 702/45

FOREIGN PATENT DOCUMENTS

JP       2004-108975 A    4/2004
WO     WO 03/027614 A    4/2003

* cited by examiner

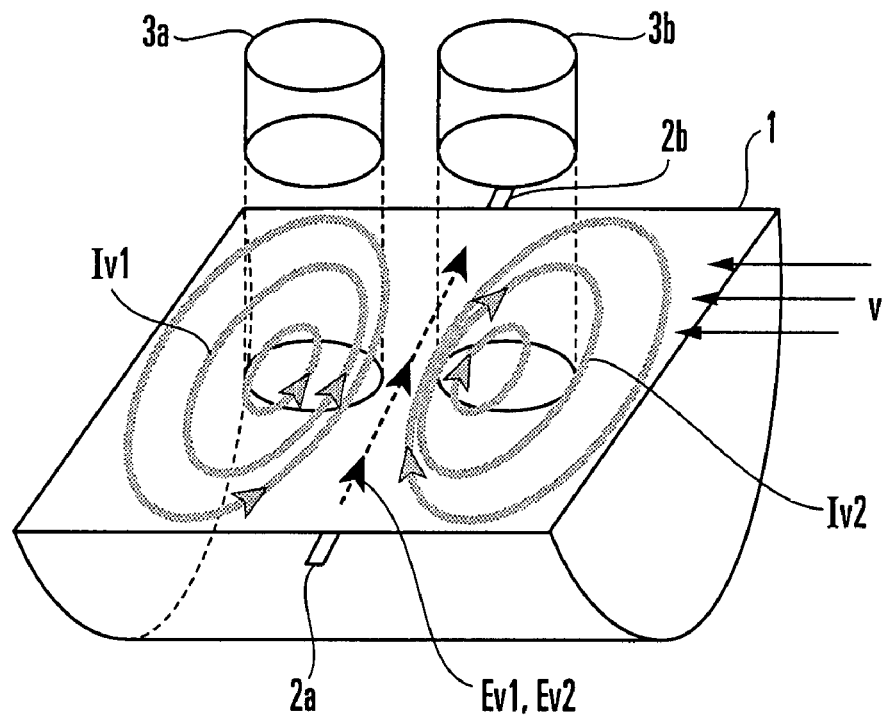
F I G. 7
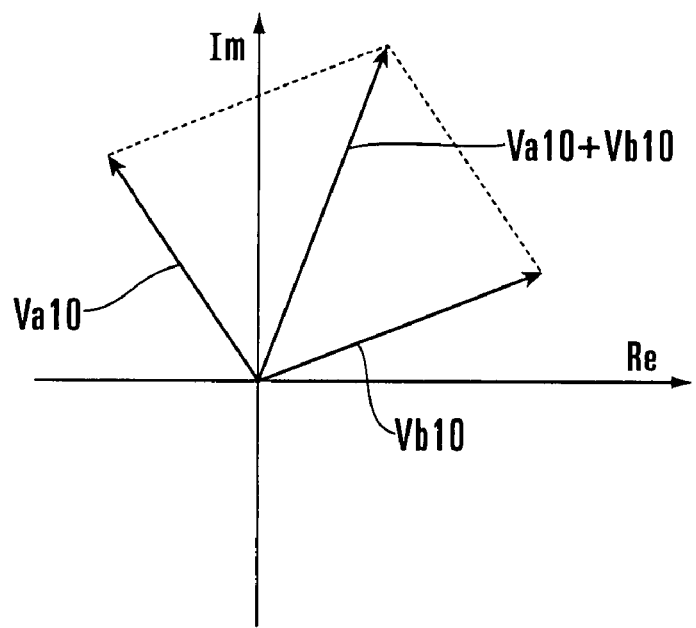
F I G. 8

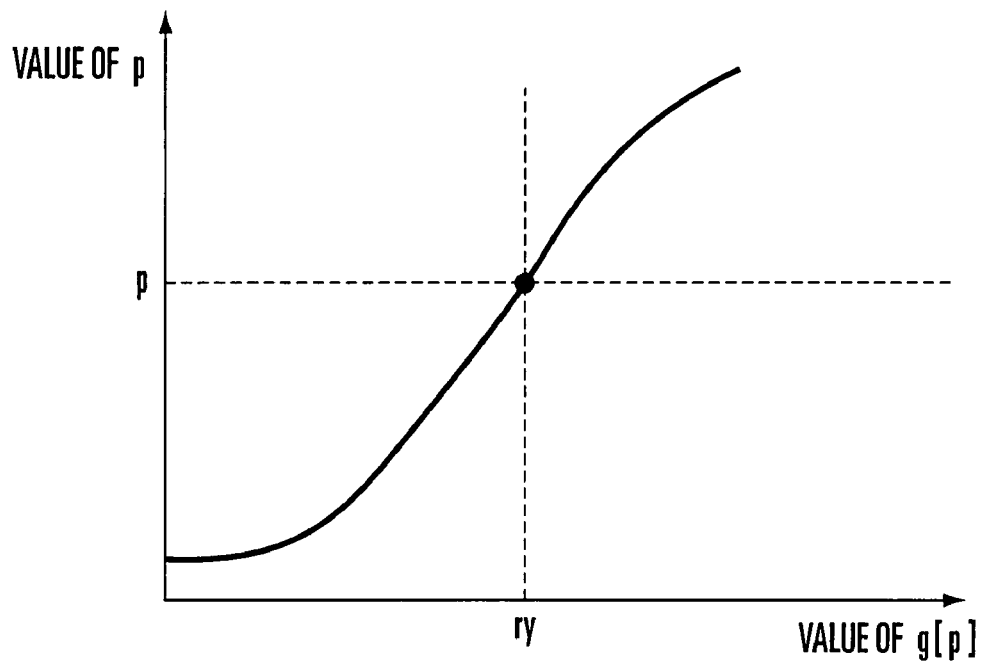
F I G. 21
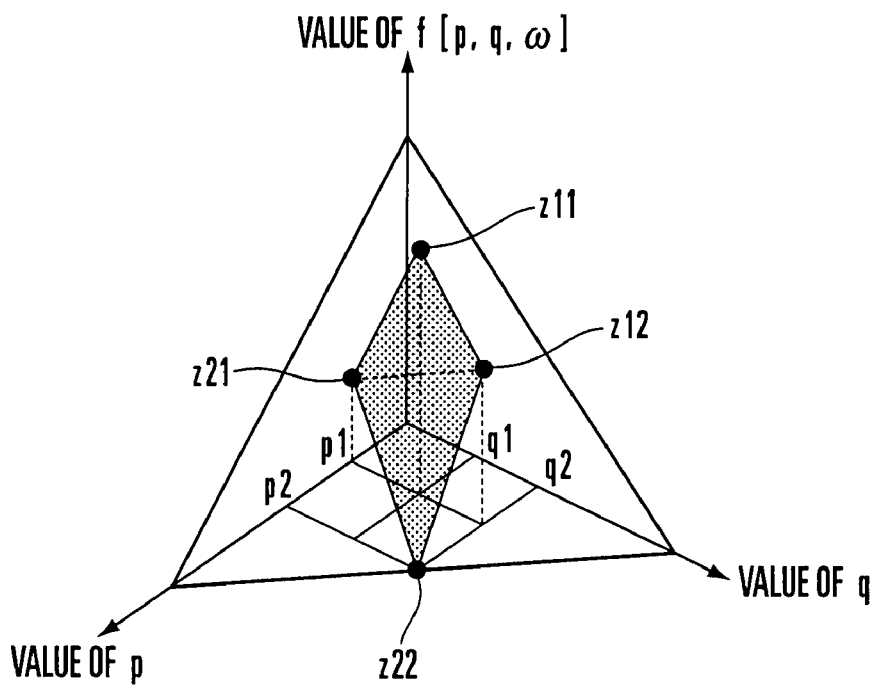
F I G. 22

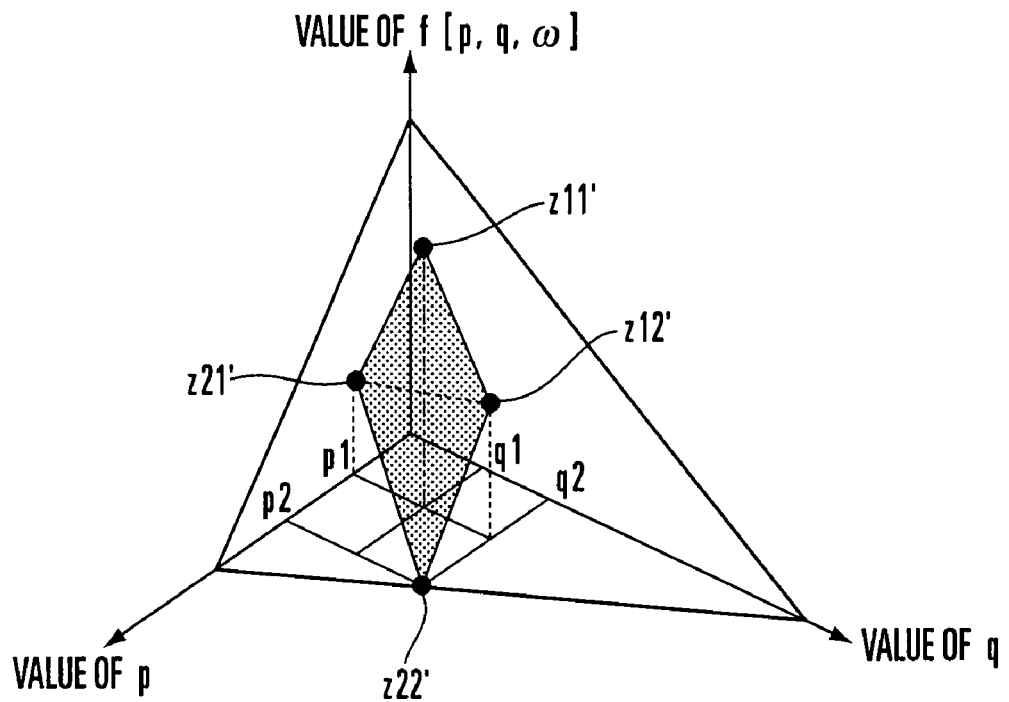
F I G. 23
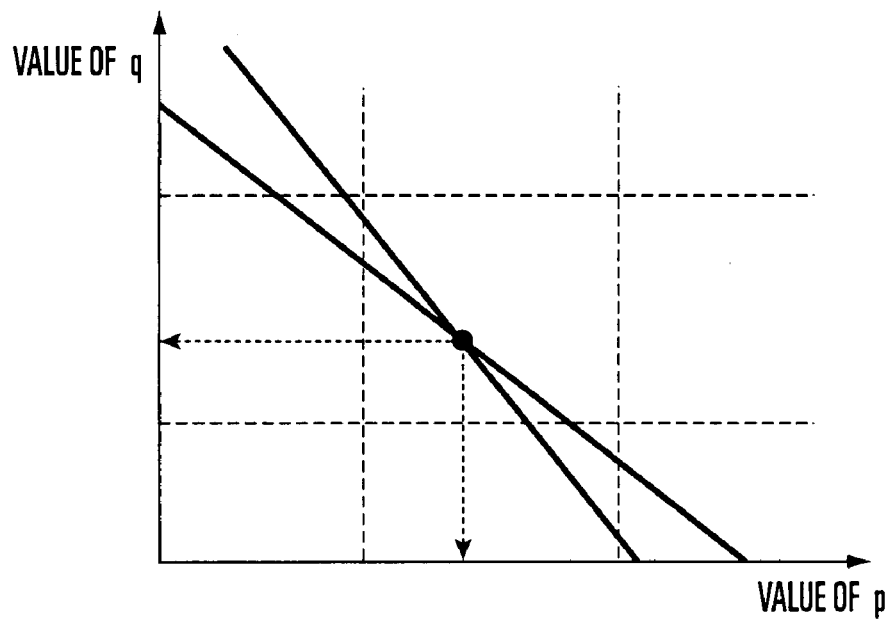
F I G. 24

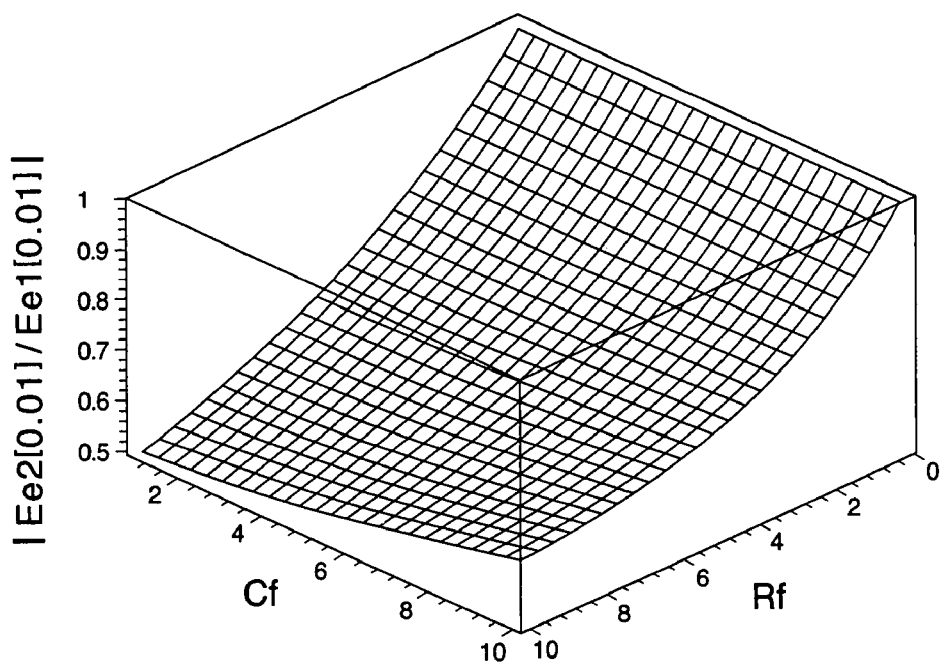
F I G. 42
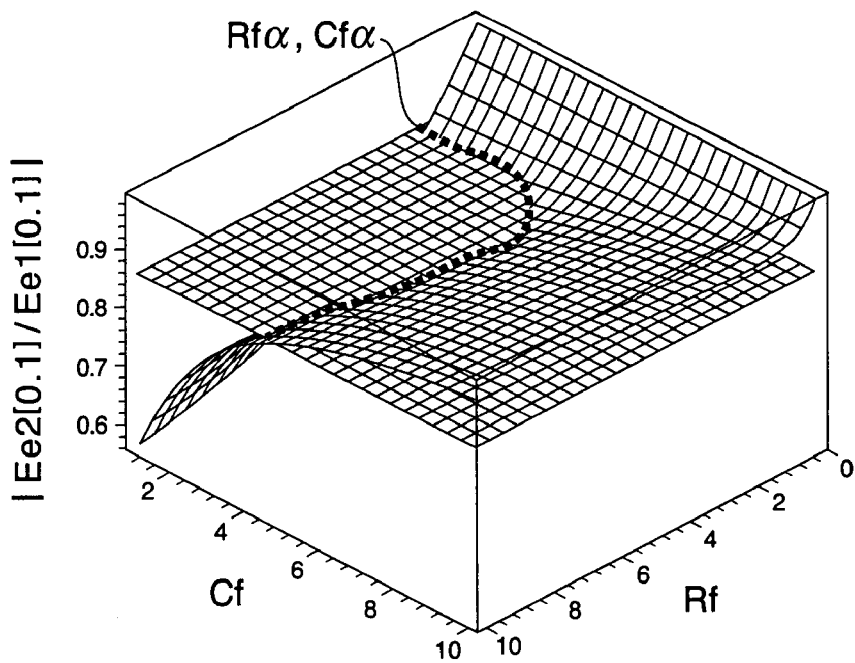
F I G. 43

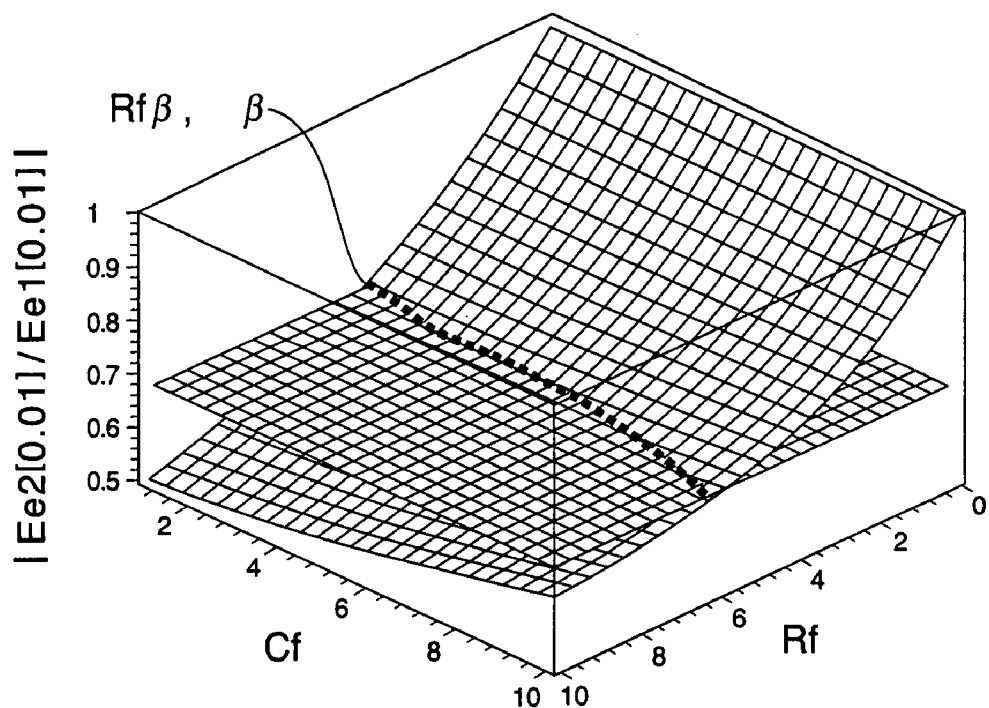
F I G. 44
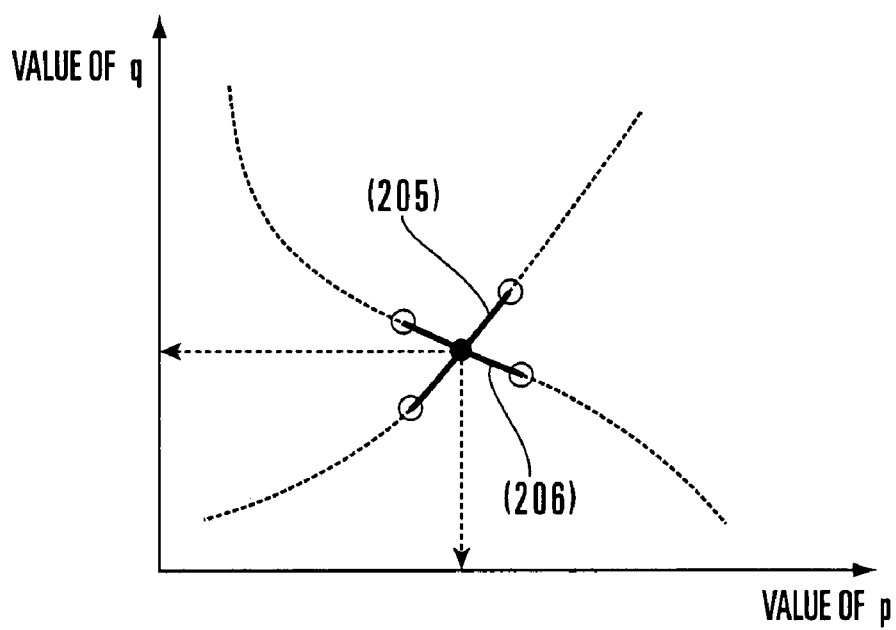
F I G. 45

STATE DETECTION DEVICE

This is a non-provisional application claiming the benefit of International application No. PCT/JP2005/017409 filed Sep. 21, 2005.

TECHNICAL FIELD

The present invention relates to a state detection device which detects a characteristic or state of a fluid or a state in a measuring tube through which the fluid flows.

BACKGROUND ART

Generally, in order to measure a flow rate by using a flowmeter, there is a demand for detecting a characteristic or state of the fluid and a state in a tube through which the fluid flows, together with the flow rate of a fluid to be measured. For example, in a manufacturing line for mixing a chemical solution or the like, the characteristic such as the conductivity or permittivity of the fluid is measured together with the flow rate of the fluid. Also, when a large amount of substance adheres to the inside of a measuring tube, the deposition state of the substance in the measuring tube is measured in order to know the maintenance cycle of the measuring tube. As for a sewer, a demand has arisen for measuring the state such as a level of the fluid and the deposition state of the substance adhering to the inside of the measuring tube together with the flow rate. Actually, the state of the fluid and the state in the measuring tube are measured by using a measuring device other than the flowmeter.

As described above, a demand has arisen for measuring the characteristic or state of the fluid or the state in the measuring tube though which the fluid flows, together with the flow rate of the fluid, and executing measurement processing by using basically the same hardware arrangement as that of a flowmeter. That is, there is a demand for selectively implementing various functions such as measurement of the flow rate of the fluid, measurement of the conductivity of the fluid, and simultaneous measurement of the flow rate and conductivity by using one measurement device. Since the flow rate and state are preferably measured at the same time, it is obviously important to measure the characteristic or state of the fluid regardless of the flow rate of the fluid.

When an electromagnetic flowmeter serves as the flowmeter, in addition to the above demands, a demand has arisen for measuring the characteristic or state of the fluid or the state in the measuring tube from the viewpoint of the self-diagnosis of the electromagnetic flowmeter. For example, when an insulator or the like adheres to the electrode, an electrode type flowmeter for extracting a potential from an electrode which is in contact with the fluid can neither accurately extract the potential, nor measure the flow rate with precision. To cope with this problem, when the resistance of the fluid containing the substance can be measured by using the same electrode, the deposition state of the substance adhering to the electrode can be measured, thus preventing any trouble that an abnormal flow rate measurement value is obtained. In a general electromagnetic flowmeter, an abnormal flow rate measurement value is obtained when the conductivity of the fluid falls outside a specific range. In this case, as long as the resistance of the fluid can be measured, it is determined that an output error which has occurred when the fluid having conductivity falling within the specific range flows originates from a change in the flow rate, or the fluid conductivity falling outside the specific range. As a result, the electromagnetic flowmeter can have a self-diagnosis function as the flowmeter.

As described above, a demand has arisen for meeting the request for executing various measurement processes in addition to the measurement process of the flow rate by using basically the same hardware arrangement as that of a flowmeter.

The solution to the request is not presented now. However, an electromagnetic flowmeter which detects a parameter other than the flow velocity is disclosed, as a relatively closer technique, in reference 1 (Japanese Patent Laid-Open No. 6-241855) and reference 2 (JNMIHF edition, "Flow Rate Measurement A to Z for Instrumentation Engineers", Kogyo Gijutusha, 1995, pp. 147-148). In references 1 and 2, a device which measures the level, conductivity, and the like of the fluid is disclosed as an application of the electromagnetic flowmeter. Such electromagnetic flowmeter obtains the level of the fluid on the basis of the ratio between a signal electromotive force obtained from an electrode when driving exciting coils placed above and under a tube and a signal electromotive force obtained when driving the exciting coil placed above the tube by itself, and obtains the conductivity of the fluid on the basis of the ratio between the signal electromotive forces obtained when changing an input impedance of a preamplifier connected to the electrode.

DISCLOSURE OF INVENTION

Problem to be Solved by the Invention

However, an electromagnetic flowmeter disclosed in references 1 and 2 detects a characteristic or state of a fluid on the basis of the fluid between flow rate signals. Hence, a large error occurs as the flow rate of the fluid decreases to 0, and the electromagnetic flowmeter cannot detect the characteristic or state of the fluid when the flow rate is 0.

The present invention has been made to solve the above problem, and has as its object to provide a state detection device which can accurately detect the characteristic or state of the fluid or the state in the measuring tube regardless of the flow velocity of the fluid by using basically the same hardware arrangement as that of an electromagnetic induction type flowmeter.

Means of Solution to the Problem

According to the present invention, there is provided a state detection device characterized by comprising a measuring tube through which a fluid flows, an exciting unit which applies, to the fluid, a time-changing magnetic field asymmetrical to a first plane perpendicular to an axial direction of the measuring tube, an electrode which is placed on the first plane in the measuring tube to detect a resultant electromotive force of an electromotive force based on a $\partial A/\partial t$ component (A: vector potential, t: time) irrelevant to a flow velocity of the fluid and an electromotive force based on a v×B component (v: flow velocity, B: magnetic flux density) originating from the flow velocity of the fluid, the resultant electromotive force being generated by the magnetic field applied to the fluid and a flow of the fluid, and a state quantifying unit which extracts the $\partial A/\partial t$ component from the resultant electromotive force detected by the electrode, extracts, from the $\partial A/\partial t$ component, a variation factor dependent on a parameter to be detected, and quantifies the parameter on the basis of the variation factor, wherein the parameter is at least one of a characteristic and state of the fluid and a state in the measuring tube.

According to the present invention, a $\partial A/\partial t$ component is extracted from a resultant vector of a v×B component dependent on the flow velocity of the fluid and a $\partial A/\partial t$ component independent of the flow velocity of the fluid. On the basis of the detected ∂A/∂t component, a characteristic or state of the fluid or a state in a measuring tube can be measured. This is a solution to the demand for detecting the characteristic or state of the fluid and the state in the measuring tube through which the fluid flows in addition to the flow rate of the fluid. That is, the present invention can provide a device which can detect the characteristic or state of the fluid or the state in the measuring tube regardless of the flow velocity of the fluid by using basically the same hardware arrangement as that of a flowmeter. Furthermore, the technique of the present invention can cope with the demand for measuring the characteristic or state of the fluid in addition to the level, conductivity, and permittivity of the fluid.

BRIEF DESCRIPTION OF DRAWINGS

FIG. 7 is a view showing eddy currents and inter-electrode electromotive forces when the flow rate of the fluid to be measured is not 0 in the state detection device shown in FIG. 5;

FIG. 8 is a graph showing a ∂A/∂t component vector, a v×B component vector, and a resultant vector obtained when performing excitation by using only the first exciting coil in the first excitation state in the state detection device shown in FIG. 5;

FIG. 21 is a graph for explaining another method of generating the second table in the state detection device of the present invention;

FIG. 22 is a graph for explaining a method of generating the third table in the state detection device of the present invention;

FIG. 23 is a graph for explaining a method of generating the third table in the state detection device of the present invention;

FIG. 24 is a graph for explaining a method of generating the third table in the state detection device of the present invention;

FIG. 42 is a graph showing another example of the relationship between the magnitude of the ratio between variation factors and the resistance component of the fluid impedance according to the fifth embodiment of the present invention;

FIG. 43 is a graph showing the candidates of solutions of the resistance component and capacitive component of a fluid impedance with the first angular frequency;

FIG. 44 is a graph showing the candidates of solutions of the resistance component and capacitive component of a fluid impedance with the second angular frequency;

FIG. 45 is a graph showing a method of obtaining the solutions of the resistance component and capacitive component of the fluid impedance;

BEST MODE FOR CARRYING OUT THE INVENTION

Figure 1:
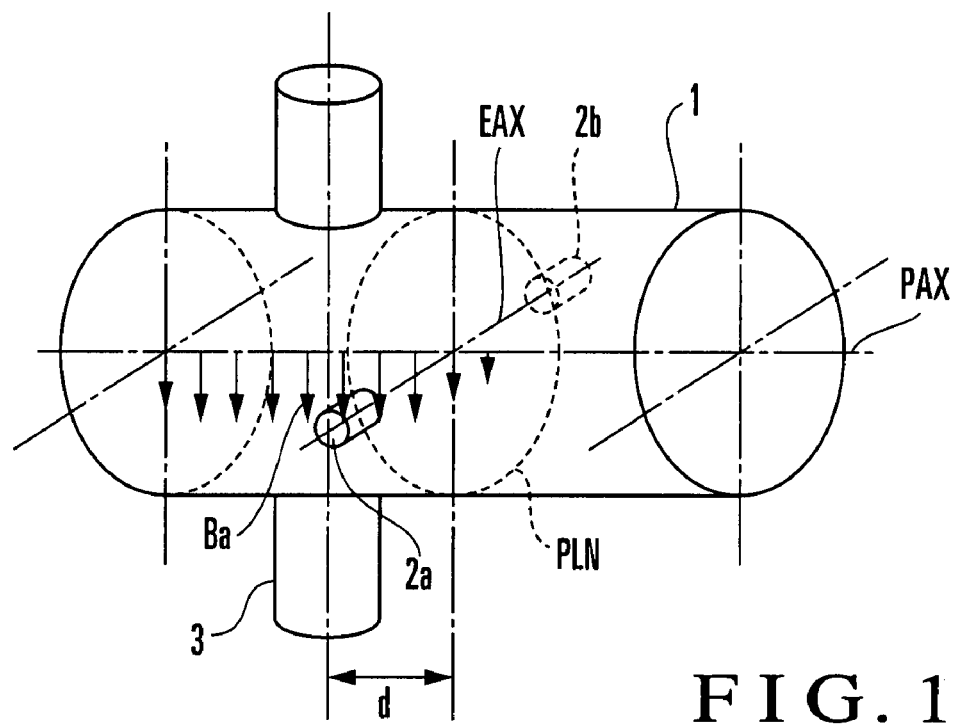
FIG. 1 is a block diagram for explaining the first principle of a state detection device of the present invention.

A logical propositional portion necessary to understand the present invention will be described. Generally known mathematical basic knowledge will be described first.

A cosine wave $P \cdot \cos(\omega \cdot t)$ and a sine wave $Q \cdot \sin(\omega \cdot t)$ which have the same frequency but different amplitudes are combined into the following cosine wave. Let P and Q be amplitudes, and $\omega$ be an angular frequency.

$$P \cdot \cos(\omega \cdot t) + Q \cdot \sin(\omega \cdot t) = (P^2 + Q^2)^{1/2} \cdot \cos(\omega \cdot t - \epsilon) \text{ for } \epsilon = \tan^{-1}(Q/P) \quad (1)$$

In order to analyze the combining operation in equation (1), it is convenient to perform mapping on a complex coordinate plane so as to plot an amplitude P of cosine wave $P \cdot \cos(\omega \cdot t)$ along a real axis and an amplitude Q of the sine wave $Q \cdot \sin(\omega \cdot t)$ along an imaginary axis. That is, on the complex coordinate plane, a distance $(P^2 + Q^2)^{1/2}$ from the origin gives the amplitude of the combined wave, and an angle $\epsilon = \tan^{-1}(Q/P)$ with respect to the real axis gives the phase difference between the combined wave and fit.

In addition, on the complex coordinate plane, the following relational expression holds.

$$L \cdot \exp(j \cdot \epsilon) = L \cdot \cos(\epsilon) + j \cdot L \cdot \sin(\epsilon) \quad (2)$$

Equation (2) is an expression associated with a complex vector, in which j is an imaginary unit, L gives the length of the complex vector, and $\epsilon$ gives the direction of the complex vector. In order to analyze the geometrical relationship on the complex coordinate plane, it is convenient to use conversion to a complex vector.

The following description uses mapping onto a complex coordinate plane like that described above and geometrical analysis using complex vectors to show how an inter-electrode electromotive force behaves and explain how the present invention uses this behavior.

A physical phenomenon necessary for explanation of a state detection device of the present invention will be described next. When an object moves in a changing magnetic field, electromagnetic induction generates two types of electric fields, namely (a) electric field $E^{(i)} = \partial A / \partial t$ which is generated by a temporal change in magnetic field, and (b) electric field $E^{(v)} = v \times B$ which is generated as the object moves in the magnetic field. In this case, $v \times B$ represents the outer product of v and B, $\partial A / \partial t$ represents the partial differential of A with respect to time. In this case, v, B, and A respectively correspond to the following and are vectors having directions in three dimensions (x, y, and z) (v: flow velocity, B: magnetic flux density, and A: vector potential (whose relationship with the magnetic flux density is represented by B=rotA). Note, however, that the three-dimensional vectors in this case differ in meaning from vectors on a complex plane. These two types of electric fields generate a potential distribution in the fluid, and electrodes can detect this potential. Consider an eddy current which is generated in a fluid by a $\partial A / \partial t$ component irrelevant to the flow velocity. The flow path or current density of the eddy current changes depending on a characteristic or state of the measuring tube including the fluid and the input impedance generated when a potential is extracted. Extracting this change as a potential makes it possible to measure a characteristic or state other than the fluid.

[First Principle]

FIG. 1 is a block diagram for explaining the first principle of the state detection device of the present invention. This state detection device includes a measuring tube 1 through which a fluid to be measured flows, a pair of electrodes 2a and 2b which are placed to face each other in the measuring tube 1 so as to be perpendicular to both a magnetic field to be applied to the fluid and an axis PAX of the measuring tube 1 and come into contact with the fluid, and detect the electromotive force generated by the magnetic flow and the flow of the fluid, and an exciting coil 3 which applies, to the fluid, a time-changing magnetic field asymmetric on the front and rear sides of the measuring tube 1 which are bordered on a plane PLN which includes the electrodes 2a and 2b perpendicular to the axis PAX of the measuring tube, with the plane PLN serving as a boundary of the measuring tube 1.

As shown in FIG. 1, the present invention is configured to apply, to the fluid, a magnetic field asymmetric on the front and rear sides of the measuring tube 1 which are bordered on a plane PLN which includes the electrodes 2a and 2b perpendicular to the axis PAX of the measuring tube, with the plane PLN serving as a boundary of the measuring tube 1, so as to detect the resultant vector of a v×B component dependent on the flow velocity of the fluid and a ∂A/∂t component independent of the flow velocity and extract the ∂A/∂t component independent of the flow velocity of the fluid from the resultant vector. The extracted ∂A/∂t component contains a component which changes depending on the state or characteristic of the fluid and that in the measuring tube 1. The conductivity, permittivity, and level of the fluid, or a state in the measuring tube 1 can be measured from the values of the components regardless of the flow rate of the fluid. The flow velocity can also be calculated from the v×B component contained in the resultant vector as in a general electromagnetic flowmeter.

Assume that, of a magnetic field Ba generated by the exciting coil 3, a magnetic field component (magnetic flux density) B1 orthogonal to both an electrode axis EAX connecting the electrodes 2a and 2b and the measuring tube axis PAX on the electrode axis EAX is given by $$B1 = b1 \cdot \cos(\omega 0 \cdot t - \theta 1) \quad (3)$$

In equation (3), b1 is the amplitude of the magnetic field B1, ω0 is an angular frequency, and θ1 is a phase difference (phase delay) between the magnetic flux density B1 and ω0·t. The magnetic flux density B1 will be referred to as the magnetic field B1 hereinafter.

An inter-electrode electromotive force which originates from a change in magnetic field and is irrelevant to the flow velocity of a fluid will be described first. Since the electromotive force originating from the change in magnetic field depends on a time derivative dB/dt of the magnetic field, and hence the magnetic field B1 generated by the exciting coil 3 is differentiated according to $$dB1/dt = -\omega 0 \cdot b1 \cdot \sin(\omega 0 \cdot t - \theta 1) \quad (4)$$

Figure 2:
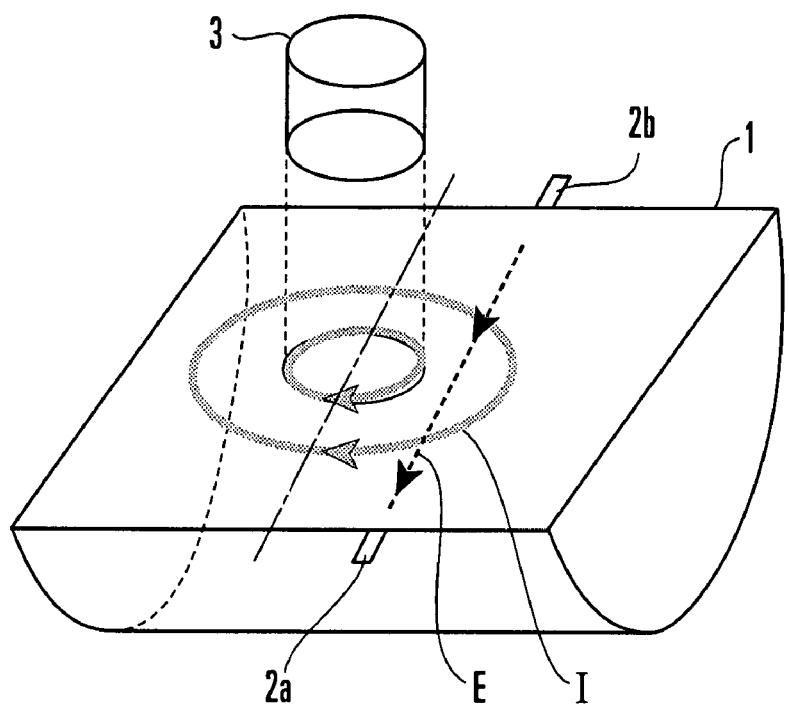
FIG. 2 is a view showing an eddy current and an inter-electrode electromotive force when the flow rate of a fluid to be measured is 0 in the state detection device shown in FIG. 1.

If the flow velocity of the fluid to be measured is 0, a generated eddy current is only a component originating from a change in magnetic field. An eddy current I due to a change in the magnetic field Ba is directed as shown in FIG. 2. Therefore, an inter-electrode electromotive force E which is generated by a change in the magnetic field Ba and is irrelevant to the flow velocity is directed as shown in FIG. 2 within a plane including the electrode axis EAX and the measuring tube axis PAX. This direction is defined as the negative direction.

At this time, the inter-electrode electromotive force E is the value obtained by multiplying a time derivative –dB1/dt of a magnetic field whose direction is taken into consideration by a proportion coefficient rk, and substituting θ1+θ00 into the phase θ1 (rk and θ00 are associated with the conductivity and permittivity of the fluid to be measured and the structure of the measuring tube 1 including the arrangement of the electrodes 2a and 2b), as indicated by the following equation:

$$E = rk \cdot \omega 0 \cdot b1 \cdot \sin(\omega 0 \cdot t - \theta 1 - \theta 00) \quad (5)$$

Equation (5) is rewritten into the following equation:

$$\begin{aligned}
E &= rk \cdot \omega 0 \cdot b1 \cdot \{\sin(-\theta 1 - \theta 00)\} \cdot \cos(\omega 0 \cdot t) + \\
&\quad rk \cdot \omega 0 \cdot b1 \cdot \{\cos(-\theta 1 - \theta 00)\} \cdot \sin(\omega 0 \cdot t) \\
&= rk \cdot \omega 0 \cdot b1 \cdot \{-\sin(\theta 1 + \theta 00)\} \cdot \cos(\omega 0 \cdot t) + \\
&\quad rk \cdot \omega 0 \cdot b1 \cdot \{\cos(\theta 1 + \theta 00)\} \cdot \sin(\omega 0 \cdot t)
\end{aligned} \quad (6)$$

In this case, if equation (6) is mapped on the complex coordinate plane with reference to ω0·t, a real axis component Ex and an imaginary axis component Ey are given by $$\begin{aligned}
Ex &= rk \cdot \omega 0 \cdot b1 \cdot \{-\sin(\theta 1 + \theta 00)\} \\
&= rk \cdot \omega 0 \cdot b1 \cdot \{\cos(\pi/2 + \theta 1 + \theta 00)\}
\end{aligned} \quad (7)$$

$$\begin{aligned}
Ey &= rk \cdot \omega 0 \cdot b1 \cdot \{\cos(\theta 1 + \theta 00)\} \\
&= rk \cdot \omega 0 \cdot b1 \cdot \{\sin(\pi/2 + \theta 1 + \theta 00)\}
\end{aligned} \quad (8)$$

In addition, Ex and Ey represented by equations (7) and (8) are transformed into a complex vector Ec represented by $$\begin{aligned}
Ec &= Ex + j \cdot Ey \\
&= rk \cdot \omega 0 \cdot b1 \cdot \{\cos(\pi/2 + \theta 1 + \theta 00)\} + \\
&\quad j \cdot rk \cdot \omega 0 \cdot b1 \cdot \{\sin(\pi/2 + \theta 1 + \theta 00)\} \\
&= rk \cdot \omega 0 \cdot b1 \cdot \\
&\quad \{\cos(\pi/2 + \theta 1 + \theta 00) + j \cdot \sin(\pi/2 + \theta 1 + \theta 00)\} \\
&= rk \cdot \omega 0 \cdot b1 \cdot \exp\{j \cdot (\pi/2 + \theta 1 + \theta 00)\}
\end{aligned} \quad (9)$$

The inter-electrode electromotive force Ec represented by equation (9) which is transformed into complex coordinates becomes an inter-electrode electromotive force which originates from only a temporal change in magnetic field and is irrelevant to the flow velocity. In equation (9), rk·ω0·b1·exp{j·(π/2+θ1+θ00)} is a complex vector having a length rk·ω0·b1 and an angle π/2+θ1+θ00 with respect to the real axis.

In addition, the proportion coefficient rk and angle θ00 described above can be transformed into a complex vector kc to obtain the following equation:

$$\begin{aligned}
kc &= rk \cdot \cos(\theta 00) + j \cdot rk \cdot \sin(\theta 00) \\
&= rk \cdot \exp(j \cdot \theta 00)
\end{aligned} \quad (10)$$

In equation (10), rk is the magnitude of the vector kc, and θ00 is the angle of the vector kc with respect to the real axis.

Figure 3:
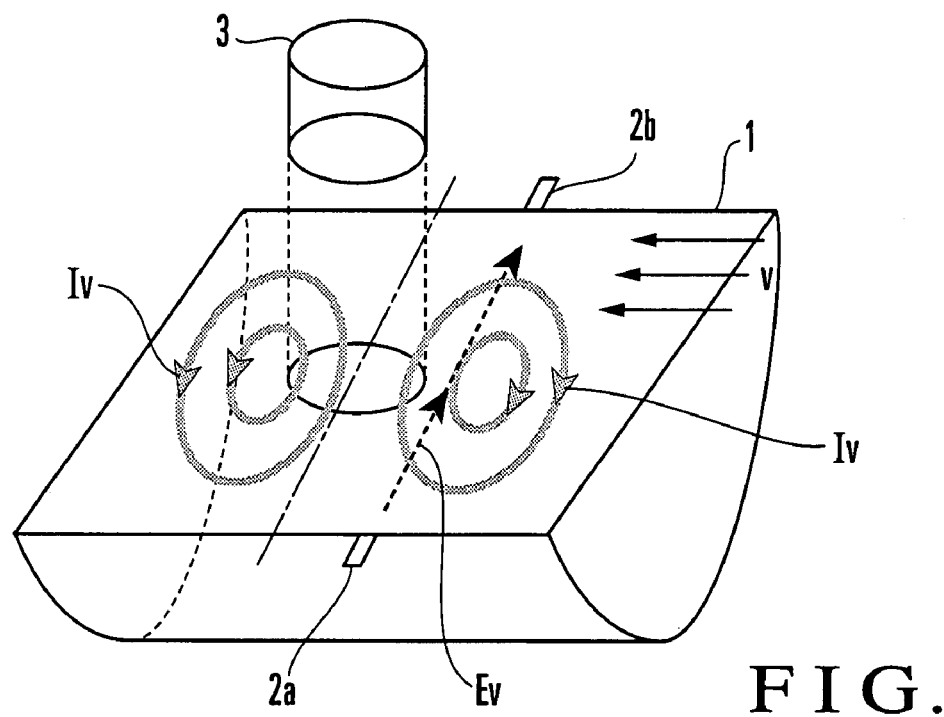
FIG. 3 is a view showing eddy currents and an inter-electrode electromotive force when the flow rate of the fluid to be measured is not 0 in the state detection device shown in FIG. 1.

An inter-electrode electromotive force originating from the flow velocity of a fluid to be measured will be described next. Letting V (V≠0) be the magnitude of the flow velocity of the fluid, since a component v×Ba originating from a flow velocity vector v of the fluid is generated in a generated eddy current in addition to the eddy current I when the flow velocity is 0, an eddy current Iv generated by the flow velocity vector v and the magnetic field Ba is directed as shown in FIG. 3. Therefore, the direction of an inter-electrode electromotive force Ev generated by the flow velocity vector v and the magnetic field Ba becomes opposite to the direction of the inter-electrode electromotive force E generated by the temporal change, and the direction of Ev is defined as the positive direction.

In this case, as indicated by the following equation, the inter-electrode electromotive force Ev originating from the flow velocity is the value obtained by multiplying the magnetic field B1 by a proportion coefficient rkv, and substituting $\theta 1+\theta 01$ into the phase $\theta 1$ (rkv and $\theta 1$ are associated with a magnitude V of the flow velocity, the conductivity and permittivity of the fluid to be measured, and the structure of the measuring tube 1 including the arrangement of the electrodes 2a and 2b):

$$Ev = rkv \cdot \{b1 \cdot \cos(\omega 0 \cdot t - \theta 1 - \theta 01)\} \quad (11)$$

Equation (11) is rewritted into $$\begin{aligned} Ev &= rkv \cdot b1 \cdot \cos(\omega 0 \cdot t) \cdot \cos(-\theta 1 - \theta 01) - \\ &\quad rkv \cdot b1 \cdot \sin(\omega 0 \cdot t) \cdot \sin(-\theta 1 - \theta 01) \\ &= rkv \cdot b1 \cdot \{\cos(\theta 1 + \theta 01)\} \cdot \cos(\omega 0 \cdot t) + \\ &\quad rkv \cdot b1 \cdot \{\sin(\theta 1 + \theta 01)\} \cdot \sin(\omega 0 \cdot t) \end{aligned} \quad (12)$$

In this case, when mapping equation (12) on the complex coordinate plane with reference to $\omega 0 \cdot t$, a real axis component Evx and an imaginary axis component Evy are given by $$Evx = rkv \cdot b1 \cdot \{\cos(\theta 1 + \theta 01)\} \quad (13)$$

$$Evy = rkv \cdot b1 \cdot \{\sin(\theta 1 + \theta 01)\} \quad (14)$$

In addition, Evx and Evy represented by equations (13) and (14) are transformed into a complex vector Evc represented by $$\begin{aligned} Evc &= Evx + j \cdot Evy \\ &= rkv \cdot b1 \cdot \{\cos(\theta 1 + \theta 01)\} + \\ &\quad j \cdot rkv \cdot b1 \cdot \{\sin(\theta 1 + \theta 01)\} \\ &= rkv \cdot b1 \cdot \{\cos(\theta 1 + \theta 01) + j \cdot \sin(\theta 1 + \theta 01)\} \\ &= rkv \cdot b1 \cdot \exp\{j \cdot (\theta 1 + \theta 01)\} \end{aligned} \quad (15)$$

The inter-electrode electromotive force Evc represented by equation (15) which is transformed into complex coordinates becomes an inter-electrode electromotive force which originates from the flow velocity of the fluid to be measured. In equation (15), $rkv \cdot b1 \cdot \exp\{j \cdot (\theta 1 + \theta 01)\}$ is a complex vector having a length $rkv \cdot b1$ and an angle $\theta 1 + \theta 01$ with respect to the real axis.

In addition, the proportion coefficient rkv and $\theta 01$ described above can be transformed into a complex vector kvc to obtain the following equation:

$$\begin{aligned} kvc &= rkv \cdot \cos(\theta 01) + j \cdot rkv \cdot \sin(\theta 01) \\ &= rkv \cdot \exp(j \cdot \theta 01) \end{aligned} \quad (16)$$

In equation (16), rkv is the magnitude of the vector kvc, and $\theta 01$ is the angle of the vector kvc with respect to the real axis. In this case, rkv is equivalent to the value obtained by multiplying the proportional coefficient rk (see equation (10)) described above by the magnitude V of the flow velocity and a proportion coefficient $\gamma$. That is, the following equation holds:

$$rkv = \gamma \cdot rk \cdot V \quad (17)$$

An inter-electrode electromotive force Ea1c as a combination of inter-electrode electromotive force Ec originating from a temporal change in magnetic field and an inter-electrode electromotive force Evc originating from the flow velocity of the fluid is expressed by the following equation upon combining equation (9) and an equation obtained by substituting equation (17) into equation (15).

$$\begin{aligned} Ea1c &= rk \cdot \omega 0 \cdot b1 \cdot \exp\{j \cdot (\pi/2 + \theta 1 + \theta 00)\} + \\ &\quad \gamma \cdot rk \cdot V \cdot b1 \cdot \exp\{j \cdot (\theta 1 + \theta 01)\} \end{aligned} \quad (18)$$

As is obvious from equation (18), an inter-electrode electromotive force Ea1c is written by two complex vectors, i.e., the $\partial A/\partial t$ component $rk \cdot \omega 0 \cdot b1 \cdot \exp\{j \cdot (\pi/2+\theta 1+\theta 00)\}$ and the v×B component $\gamma \cdot rk \cdot V \cdot b1 \cdot \exp\{j \cdot (\theta 1+\theta 01)\}$. The length of the resultant vector obtained by combining the two complex vectors represents the amplitude of the output (the inter-electrode electromotive force Ea1c), and an angle $\phi$ of the resultant vector represents the phase difference (phase delay) of the inter-electrode electromotive force Ea1c with respect to the phase $\omega 0 \cdot t$ of the input (exciting current).

The angle $\theta 00$ is the angle of the vector kc with respect to the real axis, and the angle $\theta 01$ is the angle of the vector kvc with respect to the real axis. These definitions can be rephrased such that $\theta 00$ is the angle of the $\partial A/\partial t$ component with respect to the imaginary axis, and $\theta 01$ is the angle of the v×B component with respect to the real axis. Assume that the inter-electrode electromotive force Ea1c is represented by E10 in a state wherein the relationship between the angles $\theta 00$ and $\theta 01$ is defined as $\theta 01=\theta 00+\Delta\theta 01$. In this case, the inter-electrode electromotive force E10 is represented by the following equation:

$$\begin{aligned} E10 &= rk \cdot \omega 0 \cdot b1 \cdot \exp\{j \cdot (\pi/2 + \theta 1 + \theta 00)\} + \\ &\quad \gamma \cdot rk \cdot V \cdot b1 \cdot \exp\{j \cdot (\theta 1 + \theta 00 + \Delta\theta 01)\} \end{aligned} \quad (19)$$

Assuming that the $\partial A/\partial t$ component in the resultant vector represented by equation (19) is given by a product Va10 obtained by multiplying a constant term $Ka = \text{ext}(j \cdot \pi/2)$ in the $\partial A/\partial t$ component, a term $B1c = b1 \cdot \exp\{j \cdot \theta 1\}$ associated with the magnetic field, a term $C = rk \cdot \exp(j \cdot \theta 00)$ associated with the characteristic or state of the fluid, and the angular frequency $\omega 0$, the first term of the right side of equation (19) is represented by equation (20).

$$Va10 = Ka \cdot B1c \cdot C \cdot \omega 0 \quad (20)$$

Assuming that the v×B component in the resultant vector is given by a product Vb10 obtained by multiplying a constant term $Kb = \gamma \cdot \exp(j \cdot \Delta\theta 01)$ in the v×B component, a term $B1c = b1 \cdot \exp(j \cdot \theta 1)$ associated with the magnetic field, a term $C = rk \cdot \exp(j \cdot \theta 00)$ associated with the characteristic or state of the fluid, and the magnitude V of the flow velocity, the second term of the right side of equation (19) is represented by equation (21).

$$Vb10 = Kb \cdot B1c \cdot C \cdot V \quad (21)$$

Figure 4:
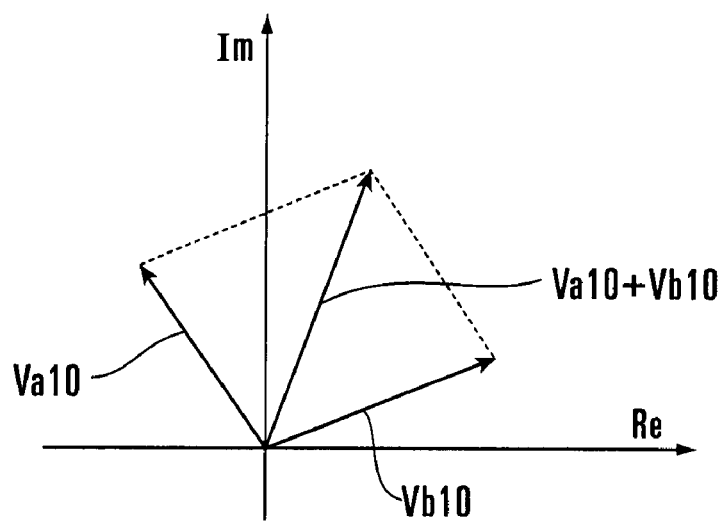
FIG. 4 is a graph showing a ∂A/∂t component vector, a v×B component vector, and a resultant vector in the state detection device shown in FIG. 1.

FIG. 4 is a graph showing the vector Va10, vector Vb10, and resultant vector (flow velocity V) Va10+Vb10. When extracting only Va10 from the resultant vector Va10+Vb10, and extracting the variation factor C dependent on the characteristic or state of the fluid, a change in the characteristic or state of the fluid or the state in the measuring tube can be known independently of the flow velocity. A method of extracting the ∂A/∂t component from the resultant vector will be generally described.

[Second Principle]

Figure 5:
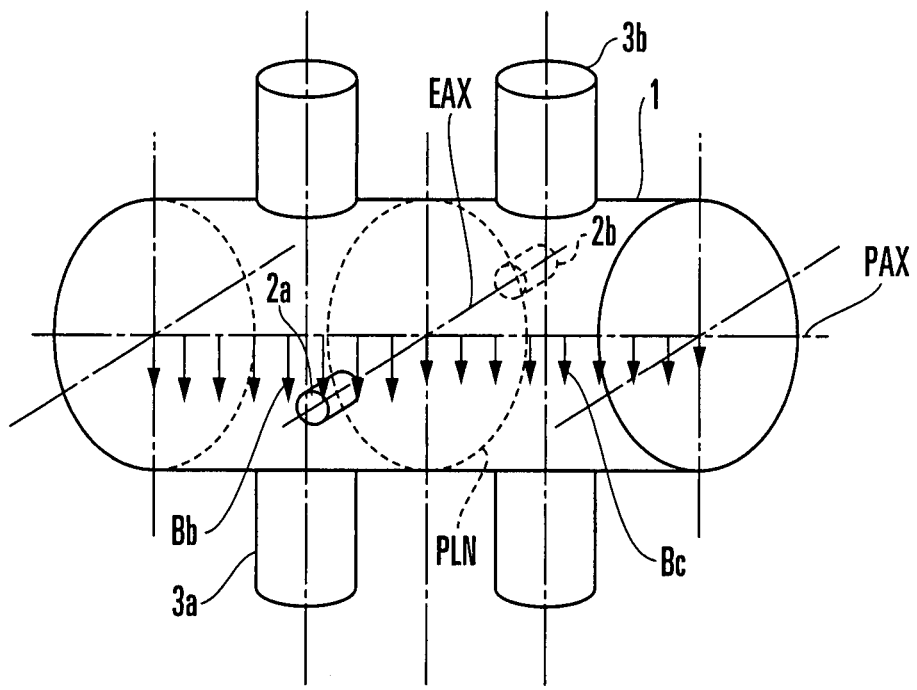
FIG. 5 is a block diagram for explaining the second principle of a state detection device of the present invention.

FIG. 5 is a block diagram for explaining the second principle of a state detection device of the present invention. This state detection device includes a measuring tube 1, electrodes 2a and 2b, and first and second exciting coils 3a and 3b which apply, to a fluid to be measured, time-changing magnetic fields asymmetric on the front and rear sides of the measuring tube 1 which are bordered on a plane PLN which is perpendicular to the direction of a measuring tube axis PAX and includes the electrodes 2a and 2b, when the plane PLN serves as a boundary of the measuring tube 1. The first exciting coil 3a is placed at a position spaced apart from the plane PLN by an offset distance d1 to, for example, the downstream side. The second exciting coil 3b is placed at a position spaced apart from the plane PLN by an offset distance d2 to, for example, the upstream side.

The state detection device shown in FIG. 5 is obtained by adding one exciting coil to the state detection device shown in FIG. 1. If the second exciting coil 3b to be newly added is placed on the same side as the existing first exciting coil 3a, the resultant arrangement is a redundant arrangement of that shown in FIG. 1. Therefore, the second exciting coil 3b needs to be placed on a side different from that of the first exciting coil 3a through the plane PLN including the electrodes 2a an 2b. With this arrangement, if a v×B component originating from a magnetic field Bb generated from the first exciting coil 3a and the flow velocity and a v×B component originating from a magnetic field Bc generated from the second exciting coil 3b and the flow velocity, which are detected by the electrodes 2a and 2b, are directed in the same direction, a ∂A/∂t component originating from a change in the magnetic field Bb generated by the first exciting coil 3a and a ∂A/∂t component originating from a change in the magnetic field Bc generated by the second exciting coil 3b are directed in opposite directions. Using this principle makes it possible to efficiently extract a ∂A/∂t component.

Of the magnetic field Bb generated from the first exciting coil 3a, a magnetic field component (magnetic flux density) B1 orthogonal to both an electrode axis EAX connecting the electrodes 2a and 2b and the measuring tube axis PAX on the electrode axis EAX, and of the magnetic field Bc generated from the second exciting coil 3b, a magnetic field component (magnetic flux density) B2 orthogonal to both the electrode axis EAX and the measuring tube axis PAX on the electrode axis EAX are given by $$B1 = b1 \cdot \cos(\omega 0 \cdot t - \theta 1) \quad (22)$$

$$B2 = b2 \cdot \cos(\omega 0 \cdot t - \theta 2) \quad (23)$$

In equations (22) and (23), b1 and b2 are the amplitudes of the magnetic flux densities B1 and B2, ω0 is an angular frequency, and θ1 and θ2 are phase differences (phase lags) between the magnetic flux densities B1 and B2 and ω0·t. The magnetic flux densities B1 and B2 will be respectively referred to as the magnetic fields B1 and B2 hereinafter.

Since the electromotive force originating from a change in magnetic field depends on a time derivative dB/dt of the magnetic field, the magnetic field B1 generated by the exciting coil 3a and the magnetic field B2 generated by the second exciting coil 3b are differentiated by $$dB1/dt = \qquad (24)$$
$$\omega 0 \cdot \cos(\omega 0 \cdot t) \cdot b1 \cdot \{\sin(\theta 1)\} + \omega 0 \cdot \sin(\omega 0 \cdot t) \cdot b1 \cdot \{-\cos(\theta 1)\}$$

$$dB2/dt = \qquad (25)$$
$$\omega 0 \cdot \cos(\omega 0 \cdot t) \cdot b2 \cdot \{\sin(\theta 2)\} + \omega 0 \cdot \sin(\omega 0 \cdot t) \cdot b2 \cdot \{-\cos(\theta 2)\}$$

Figure 6:
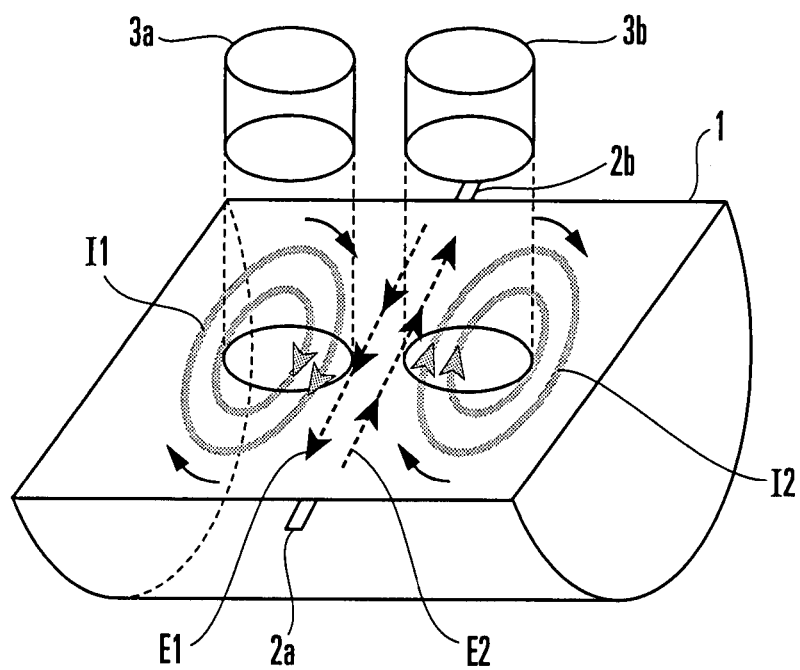
FIG. 6 is a view showing eddy currents and inter-electrode electromotive forces when the flow rate of a fluid to be measured is 0 in the state detection device shown in FIG. 5.

If the flow velocity of the fluid to be measured is 0, a generated eddy current is only a component originating from a change in magnetic field. An eddy current I1 based on the magnetic field Bb and an eddy current I2 based on the magnetic field Bc are directed as shown in FIG. 6. Therefore, an inter-electrode electromotive force E1 which is generated by a change in the magnetic field Bb and is irrelevant to the flow velocity and an inter-electrode electromotive force E2 which is generated by a change in the magnetic field Bc and is irrelevant to the flow velocity are directed opposite to each other as shown in FIG. 6 within a plane including the electrode axis EAX and the measuring tube axis PAX.

At this time, an overall inter-electrode electromotive force E as the sum of the inter-electrode electromotive forces E1 and E2 is the value obtained by multiplying the difference (−dB1/dt+dB2/dt) between time derivatives dB1/dt and dB2/dt of a magnetic field by a proportional coefficient rk and replacing the phase differences θ1 and θ2 with θ1+θ00 and θ2+θ00, respectively (rk and θ00 are associated with a conductivity and permittivity of the fluid to be measured and the structure of the measuring tube 1 including the positions of the electrodes 2a and 2b) according to the following equation:

$$E = rk \cdot \omega 0 \cdot \cos(\omega 0 \cdot t) \cdot \qquad (26)$$
$$\{-b1 \cdot \sin(\theta 1 + \theta 00) + b2 \cdot \sin(\theta 2 + \theta 00)\} +$$
$$rk \cdot \omega 0 \cdot \sin(\omega 0 \cdot t) \cdot$$
$$\{b1 \cdot \cos(\theta 1 + \theta 00) - b2 \cdot \cos(\theta 2 + \theta 00)\}$$

If the magnitude of the flow velocity of the fluid to be measured is V (V≠0), components v×Bb and v×Bc originating from a flow velocity vector v of the fluid to be measured are generated in the generated eddy currents in addition to eddy currents I1 and I2 generated when the flow velocity is 0. For this reason, an eddy current Iv1 originating from the flow velocity vector v and the magnetic field Bb and an eddy current Iv2 originating from the flow velocity vector v and the magnetic field Bc are directed as shown in FIG. 7. Consequently, an inter-electrode electromotive force Ev1 generated by the flow velocity vector v and the magnetic field Bb and an inter-electrode electromotive force Ev2 generated by the flow velocity vector v and the magnetic field Bc are directed in the same direction.

An overall inter-electrode electromotive force Ev obtained by adding the inter-electrode electromotive forces Ev1 and Ev2 is the value obtained by multiplying the sum of the magnetic fields B1 and B2 by a proportional coefficient rkv and replacing the phase differences θ1 and θ2 with θ1+θ01 and θ2+θ01, respectively (rkv and θ01 are associated with the magnitude V of the flow velocity, the conductivity and permittivity of the fluid to be measured, and the structure of the measuring tube 1 including the positions of the electrodes 2a and 2b) according to the following equation:

$$Ev = rkv \cdot \cos(\omega 0 \cdot t) \cdot \qquad (27)$$
$$\{b1 \cdot \cos(\theta 1 + \theta 01) + b2 \cdot \cos(\theta 2 + \theta 01)\} +$$
$$rkv \cdot \sin(\omega 0 \cdot t) \cdot$$
$$\{b1 \cdot \sin(\theta 1 + \theta 01) + b2 \cdot \sin(\theta 2 + \theta 01)\}$$

Considering the directions of the inter-electrode electromotive forces described with reference to FIGS. 6 and 7, of an overall inter-electrode electromotive force obtained by combining the electromotive force obtained by converting the inter-electrode electromotive force originating from a temporal change in magnetic field into a complex vector and the electromotive force obtained by converting the inter-electrode electromotive force originating from the flow velocity of the fluid to be measured into a complex vector, a component Ea2c with an angular frequency ω0 is expressed by applying the equation (17) to the equations (26) and (27).

$$Ea2c = rk \cdot \omega 0 \cdot b1 \cdot \exp\{j \cdot \{\pi/2 + \theta 1 + \theta 00)\} + \qquad (28)$$
$$\gamma \cdot rk \cdot V \cdot b1 \cdot \exp\{j \cdot (\theta 1 + \theta 01)\} +$$
$$rk \cdot \omega 0 \cdot b2 \cdot \exp\{j \cdot \{-\pi/2 + \theta 2 + \theta 00)\} +$$
$$+\gamma \cdot rk \cdot V \cdot b2 \cdot \exp\{j \cdot (\theta 2 + \theta 01)\}$$

Assume that a state wherein θ2=θ1+Δθ2 represents the relationship between a phase lag θ1 of the magnetic field B1 with respect to ω0·t and a phase lag θ2 of the magnetic field B2 with respect to ω0·t, and θ01=θ00+Δθ01 represents the relationship between the angle θ00 of the ∂A/∂t component with respect to the imaginary axis and the angle θ01 of the v×B component with respect to the real axis. Such state is defined as an excitation state ST1. In this case, letting E20 be the inter-electrode electromotive force Ea2c in the excitation state ST1, the inter-electrode electromotive force E20 is given by $$E20 = rk \cdot \exp\{j \cdot \{\theta 1 + \theta 00)\} \cdot \qquad (29)$$
$$\exp(j \cdot \pi/2) \cdot \{b1 - b2 \cdot \exp(j \cdot \Delta\theta 2)\} \cdot \omega 0 +$$
$$rk \cdot \exp\{j \cdot \{\theta 1 + \theta 00)\} \cdot$$
$$\gamma \cdot \exp(j \cdot \Delta\theta 01)\{b1 + b2 \cdot \exp(j \cdot \Delta\theta 2)\} \cdot V$$

Assume that a state (θ2=π+θ1+Δθ2) wherein the phase difference between the magnetic fields B1 and B2 has changed from that in the excitation state ST1 by a constant value π, and θ01=θ00+Δθ01 holds is given as ST2. In this case, letting E20R be the inter-electrode electromotive force Ea2c in the excitation state ST2, the inter-electrode electromotive force E20R is represented by the following equation according to equation (29).

$$E20R = rk \cdot \exp\{j \cdot \{\theta 1 + \theta 00)\} \cdot \qquad (30)$$
$$\exp(j \cdot \pi/2) \cdot \{b1 + b2 \cdot \exp(j \cdot \Delta\theta 2)\} \cdot \omega 0 +$$
$$rk \cdot \exp\{j \cdot \{\theta 1 + \theta 00)\} \cdot$$
$$\gamma \cdot \exp(j \cdot \Delta\theta 01) \cdot \{b1 - b2 \cdot \exp(j \cdot \Delta\theta 2)\} \cdot V$$

The sum of the first term of the right side of equation (29) and the first term of the right side of equation (30) represents the overall ∂A/∂t component obtained by combining a ∂A/∂t component originating from a change in the magnetic field generated from the first exciting coil 3a and a ∂A/∂t component originating from a change in the magnetic field generated from the second exciting coil 3b. The sum of the second term of the right side of equation (29) and the second term of the right side of equation (30) represents the overall v×B component obtained by combining a v×B component originating from the magnetic field generated from the first exciting coil 3a and the flow velocity of the fluid and a v×B component originating from the magnetic field generated from the first exciting coil 3b and the flow velocity of the fluid.

In this case, if the distance d1 from the plane PLN, which is perpendicular to the measuring tube axis PAX and includes the electrodes 2a and 2b, to the first exciting coil 3a is almost equal to the distance d2 from the plane PLN to the second exciting coil 3b (d1≈d2), b1≈b2 and Δθ2≈0. In this case, equations (29) and (30) are rewritten as follows:

$$E20 \approx rk \cdot \exp\{j \cdot (\theta 1 + \theta 00)\} \cdot \{2 \cdot b1 \cdot \gamma \cdot V \cdot \exp(j \cdot \Delta\theta 01)\} \qquad (31)$$

$$E20R \approx rk \cdot \exp\{j \cdot (\theta 1 + \theta 00)\} \cdot \{2 \cdot b1 \cdot \omega 0 \cdot \exp(j \cdot \pi/2)\} \qquad (32)$$

That is, since the inter-electrode electromotive force E20 is almost only the electromotive force based on the v×B component, and the inter-electrode electromotive force E20R is almost only the electromotive force based on the ∂A/∂t component, it is obvious that keeping the phase difference between the magnetic field generated from the first exciting coil 3a and the magnetic field generated from the second exciting coil 3b at almost π makes it possible to efficiently extract a ∂A/∂t component.

Assume that, of the ∂A/∂t component in the resultant vector represented by equation (29), the portion originating from the magnetic field generated from the first exciting coil 3a is represented by a product Va10 of constant term Ka=exp(j·π/2) in the ∂A/∂t component, term B1c=b1·exp(j·θ1) associated with the magnetic field generated from the first exciting coil 3a, term C=rk·exp(j·θ00) associated with a characteristic or state of the fluid, and the angular frequency ω0. In this case, Va10 is represented by equation (33), and the ∂A/∂t component in equation (30) is also represented by Va10.

$$Va10 = Ka \cdot B1c \cdot C \cdot \omega 0 \qquad (33)$$

Assume that, of the v×B component in the resultant vector represented by equation (29), the portion originating from the magnetic field generated from the first exciting coil 3a is represented by a product Vb10 of constant term Kb=γ·exp(j·Δθ01) in the v×B component, term B1c=b1·exp(j·θ1) associated with the magnetic field generated from the first exciting coil 3a, term C=rk·exp(j·θ00) associated with a characteristic or state of the fluid, and the magnitude V of the flow velocity. In this case, Vb10 is represented by equation (34), and the v×B component in equation (30) is also represented by Vb10.

$$Vb10 = Kb \cdot B1c \cdot C \cdot V \qquad (34)$$

FIG. 8 is a graph showing a resultant vector (flow velocity V) Va10+Vb10 of the vector Va10 and the vector Vb10. Referring to FIG. 8, Re is a real axis, and Im is an imaginary axis.

Assume that, of the ∂A/∂t component in the resultant vector represented by equation (29), the portion originating from the magnetic field generated from the second exciting coil 3b is represented by a product Va20 of constant term −Ka=−exp(j·π/2) in the ∂A/∂t component, term B2c=b2·exp{j·(θ1+Δθ2)} associated with the magnetic field generated from the second exciting coil 3b, term C=rk·exp(j·θ00) associated with a characteristic or state of the fluid, and the angular frequency ω0. In this case, Va20 is represented by equation (35).

$$Va20 = -Ka \cdot B2c \cdot C \cdot \omega 0 \qquad (35)$$

Since the excitation state ST2 represented by equation (30) shifts in the phase of the magnetic field from the excitation state ST1 represented by equation (29) by $\pi$, the direction of the magnetic field reverses, and the term associated with the magnetic field generated from the second exciting coil $3b$ becomes $-B2c=-b2\cdot\exp\{j\cdot(\theta1+\Delta\theta2)\}$. If, therefore, the portion originating from the magnetic field generated from the second exciting coil $3b$, of the $\partial A/\partial t$ component in the resultant vector represented by equation (30), is represented by a product Va20R of constant term $-Ka$ in the $\partial A/\partial t$ component, term $-B2c$ associated with the magnetic field generated from the second exciting coil $3b$, term C associated with a characteristic or state of the fluid, and the angular frequency $\omega 0$, Va20R is represented by equation (36).

$$Va20R=-Ka\cdot(-B2c)\cdot C\cdot\omega 0 \quad (36)$$

Assume that, of the v×B component in the resultant vector represented by equation (29), the portion originating from the magnetic field generated from the second exciting coil $3b$ is represented by a product Vb20 of constant term $Kb=\gamma\cdot\exp(j\cdot\Delta\theta 01)$ in the v×B component, term $B2c=b2\cdot\exp\{j\cdot(\theta1+\Delta\theta2)\}$ associated with the magnetic field generated from the second exciting coil $3b$, term $C=rk\cdot\exp(j\cdot\theta 00)$ associated with a characteristic or state of the fluid, and the magnitude V of the flow velocity. In this case, Vb20 is represented by equation (37).

$$Vb20=Kb\cdot B2c\cdot C\cdot V \quad (37)$$

Figure 9:
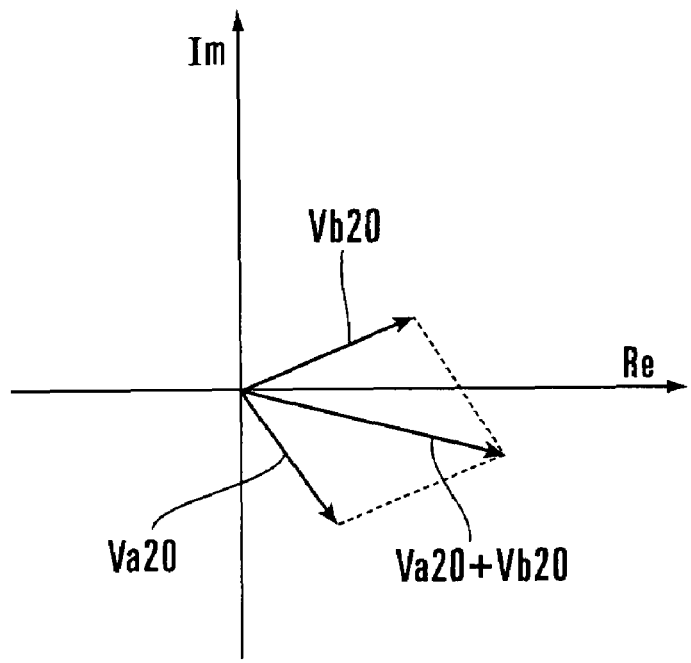
FIG. 9 is a graph showing a ∂A/∂t component vector, a v×B component vector, and a resultant vector obtained when performing excitation by using only the second exciting coil in the first excitation state in the state detection device shown in FIG. 5.
Figure 10:
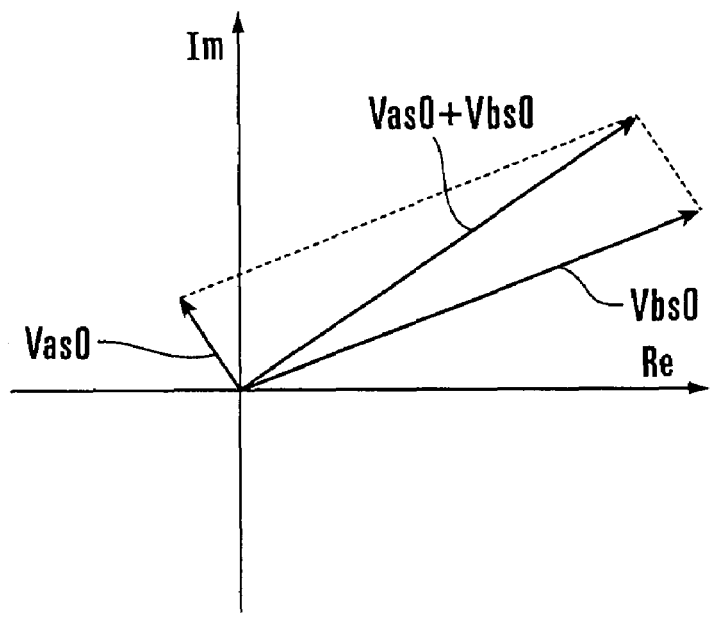
FIG. 10 is a graph showing a ∂A/∂t component vector, a v×B component vector, and a resultant vector obtained when performing excitation by using two exciting coils in the first excitation state in the state detection device shown in FIG. 5.

FIG. 9 is a graph showing a resultant vector (flow velocity V) Va20+Vb20 of the vector Va20 and the vector Vb20. FIG. 10 is a graph showing a resultant vector (flow velocity V) Vas0+Vbs0 of the vector Vas0 and the vector Vbs0. The vector Vas0 represents a $\partial A/\partial t$ component vector Va10+Va20=Ka·(B1c−B2c)·C·ω0 obtained when performing excitation by using the first and second exciting coils $3a$ and $3b$. The vector Vbs0 represents a v×B vector Vb10+Vb20=Kb·(B1c+B2c)·C·V obtained when performing excitation by using the first and second exciting coils $3a$ and $3b$.

Since the excitation state ST2 shifts in the phase of the magnetic field from the excitation state ST1 by $\pi$, a term associated with the magnetic field generated from the second exciting coil $3b$ becomes $-B2c$. If, therefore, the portion originating from the magnetic field generated from the second exciting coil $3b$, of the v×B component in the resultant vector represented by equation (30), is represented by a product Vb20R of constant term Kb in the v×B component, term $-B2c$ associated with the magnetic field generated from the second exciting coil $3b$, term C associated with a characteristic or state of the fluid, and the magnitude V of the flow velocity, Vb20R is represented by equation (38).

$$Vb20R=Kb\cdot(-B2c)\cdot C\cdot V \quad (38)$$

Figure 11:
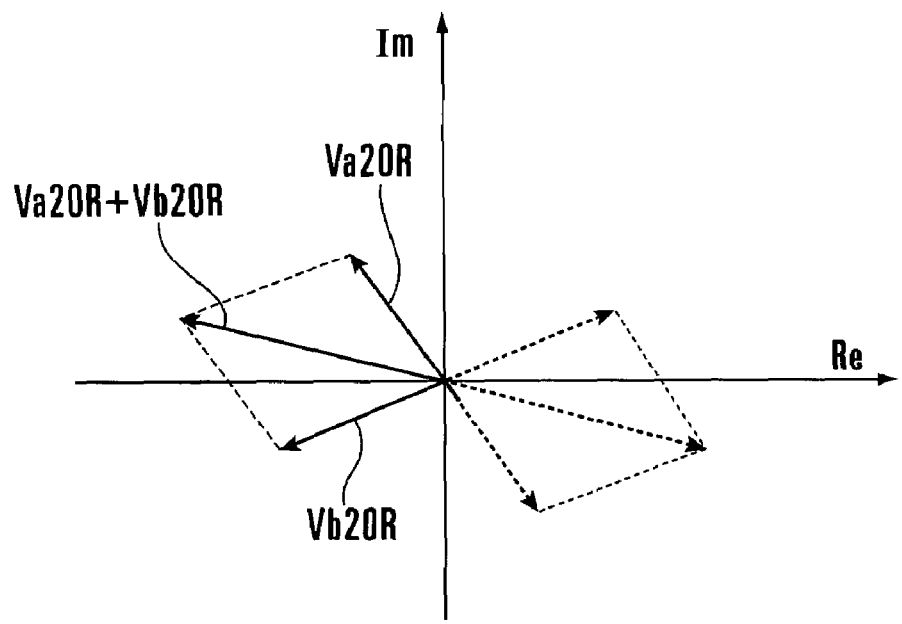
FIG. 11 is a graph showing a ∂A/∂t component vector, a v×B component vector, and a resultant vector obtained when performing excitation by using only the second exciting coil in the second excitation state in the state detection device shown in FIG. 5.
Figure 12:
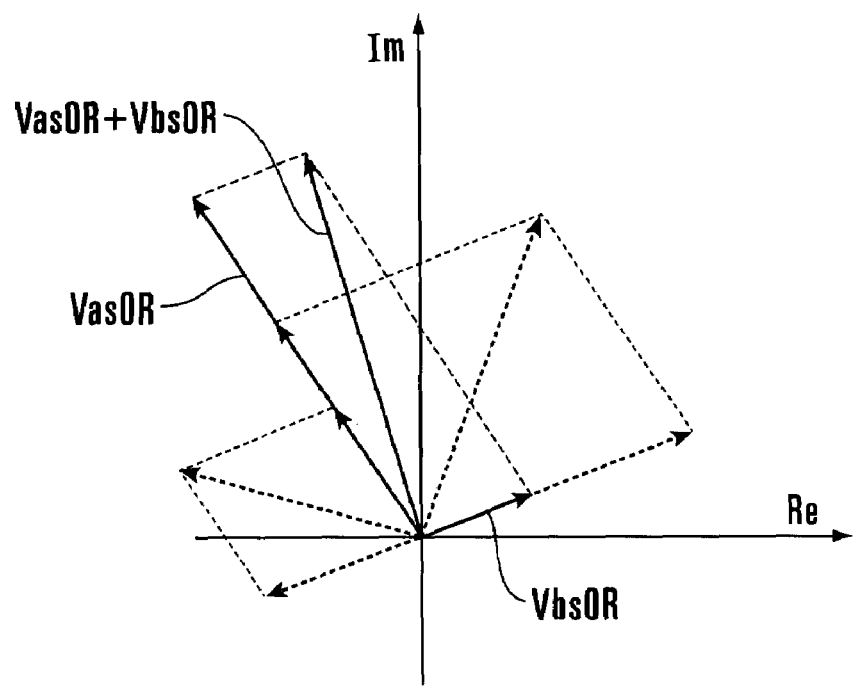
FIG. 12 is a graph showing a ∂A/∂t component vector, a v×B component vector, and a resultant vector obtained when performing excitation by using two exciting coils in the second excitation state in the state detection device shown in FIG. 5.

FIG. 11 is a graph showing a resultant vector (flow velocity V) Va20R+Vb20R of the vector Va20R and the vector Vb20R. FIG. 12 is a graph showing a resultant vector (flow velocity V) Vas0R+Vbs0R of the vector Vas0R and the vector Vbs0R. The vector Vas0R represents a $\partial A/\partial t$ component vector Va10+Va20R=Ka·(B1c+B2c)·C·ω0 obtained when performing excitation by using the first and second exciting coils $3a$ and $3b$. The vector Vbs0R represents a v×B vector Vb10+Vb20R=Kb·(B1c−B2c)·C·V obtained when performing excitation by using the first and second exciting coils $3a$ and $3b$.

According to equations (33), (34), (36), and (38), a $\partial A/\partial t$ component Va10+Va20R (the first term of the right side of equation (30)) and a v×B component Vb10+Vb20R (the second term of the right side of equation (30)) which are detected by the electrodes $2a$ and $2b$ in the excitation state ST2 are given by $$Va10+Va20R=Ka\cdot(B1c+B2c)\cdot C\cdot\omega 0 \quad (39)$$

$$Vb10+Vb20R=Kb\cdot(B1c-B2c)\cdot C\cdot V \quad (40)$$

Extracting only the $\partial A/\partial t$ component Va10+Va20R from the resultant vector E20R (=Va10+Va20R+Vb10+Vb20R) of the $\partial A/\partial t$ component and v×B component and extracting the variation factor C due to a characteristic or state of the fluid make it possible to know a change in the characteristic or state of the fluid or a state in the measuring tube independently of the flow velocity. A method of extracting a $\partial A/\partial t$ component from a resultant vector will be generalized and described later.

[Third Principle]

Figure 13:
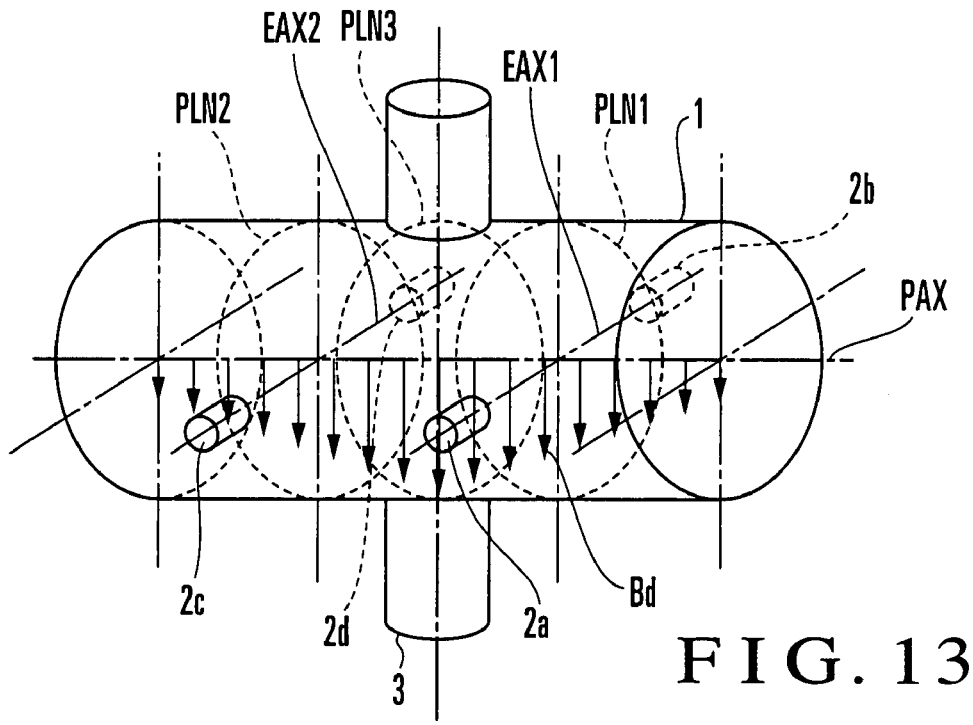
FIG. 13 is a block diagram for explaining the third principle of a state detection device of the present invention.

FIG. 13 is a block diagram for explaining the third principle of the state detection device of the present invention. This state detection device includes a measuring tube 1, first electrodes $2a$ and $2b$ and second electrodes $2c$ and $2d$ which are arranged in the measuring tube 1 to be perpendicular to both a magnetic field applied to a fluid to be measured and a measuring tube axis PAX and face each other so as to be come into contact with the fluid to be measured, and detect the electromotive force generated by the magnetic field and the flow of the fluid to be measured, and an exciting coil 3 which applies, to the fluid to be measured, a time-changing magnetic field which is asymmetric on the front and rear sides of the measuring tube 1 which are bordered on a plane PLN1 and a time-changing magnetic field which is asymmetric on the front and rear sides of the measuring tube 1 which are bordered on a plane PLN2, when a plane which is perpendicular to the measuring tube axis PAX and includes the first electrodes $2a$ and $2b$ serving as the plane PLN1 and a plane which is perpendicular to the measuring tube axis PAX and includes the second electrodes $2c$ and $2d$ serves as the plane PLN2. The first electrodes $2a$ and $2b$ are placed at a position spaced apart from a plane PLN3 which includes the axis of the exciting coil 3 and is perpendicular to the direction of the measuring tube axis PAX by an offset distance d3 to, for example, the upstream side. The second electrodes $2c$ and $2d$ are placed at a position spaced apart from the plane PLN3 by an offset distance d4 to, for example, the downstream side.

The state detection device shown in FIG. 13 is obtained by adding one pair of electrodes to the state detection device shown in FIG. 1. If the second electrodes $2c$ and $2d$ to be newly added are placed on the same side as the first electrodes $2a$ and $2b$, the resultant arrangement is a redundant arrangement of that shown in FIG. 1. Therefore, the second electrodes $2c$ and $2d$ need to be placed on a side different from that of the first electrodes $2a$ and $2b$ through the exciting coil 3. With this arrangement, a v×B component originating from the magnetic field generated from the exciting coil 3 and the flow velocity and detected by the first electrodes $2a$ and $2b$ and a v×B component originating from the magnetic field generated from the exciting coil 3 and the flow velocity and detected by the second electrodes $2c$ and $2d$ are directed in the same direction. In contrast, a $\partial A/\partial t$ component originating from a change in the magnetic field generated from the exciting coil 3, which is detected by the first electrodes $2a$ and $2b$, and a $\partial A/\partial t$ component originating from a change in the magnetic field generated by the exciting coil 3, which is detected by the second electrodes $2c$ and $2d$, are directed in opposite directions. Using this principle makes it possible to efficiently extract a $\partial A/\partial t$ component.

Of a magnetic field Bd generated from the first exciting coil 3, a magnetic field component (magnetic flux density) B3 orthogonal to both an electrode axis EAX1 connecting the electrodes $2a$ and $2b$ and the measuring tube axis PAX on the electrode axis EAX1, and of the magnetic field Bd generated from the exciting coil 3, a magnetic field component (magnetic flux density) B4 orthogonal to both an electrode axis EAX2 and the measuring tube axis PAX on the electrode axis EAX2 are given by $$B3 = b3 \cdot \cos(\omega 0 \cdot t - \theta 3) \quad (41)$$

$$B4 = b4 \cdot \cos(\omega 0 \cdot t - \theta 4) \quad (42)$$

Note, however, that since B3 and B4 are generated from the single exciting coil 3, b3 and b4, and θ3 and θ4 have some relationships with each other and are not independent variables. In equations (41) and (42), b3 and b4 are the amplitudes of the magnetic flux densities B3 and B4, ω0 is an angular frequency, and θ3 and θ4 are phase differences (phase lags) between the magnetic flux densities B3 and B4 and ω0·t. The magnetic flux densities B3 and B4 will be respectively referred to as the magnetic fields B3 and B4 hereinafter.

Since the electromotive force originating from a change in magnetic field depends on a time derivative dB/dt of the magnetic field, the magnetic fields B3 and B4 of the magnetic field Bd generated from the exciting coil 3 are differentiated according to $$dB3/dt = \quad (43)$$
$$\omega 0 \cdot \cos(\omega 0 \cdot t) \cdot b3 \cdot \{\sin(\theta 3)\} + \omega 0 \cdot \sin(\omega 0 \cdot t) \cdot b3 \cdot \{-\cos(\theta 3)\}$$

$$dB4/dt = \quad (44)$$
$$\omega 0 \cdot \cos(\omega 0 \cdot t) \cdot b4 \cdot \{\sin(\theta 4)\} + \omega 0 \cdot \sin(\omega 0 \cdot t) \cdot b4 \cdot \{-\cos(\theta 4)\}$$

Figure 14:
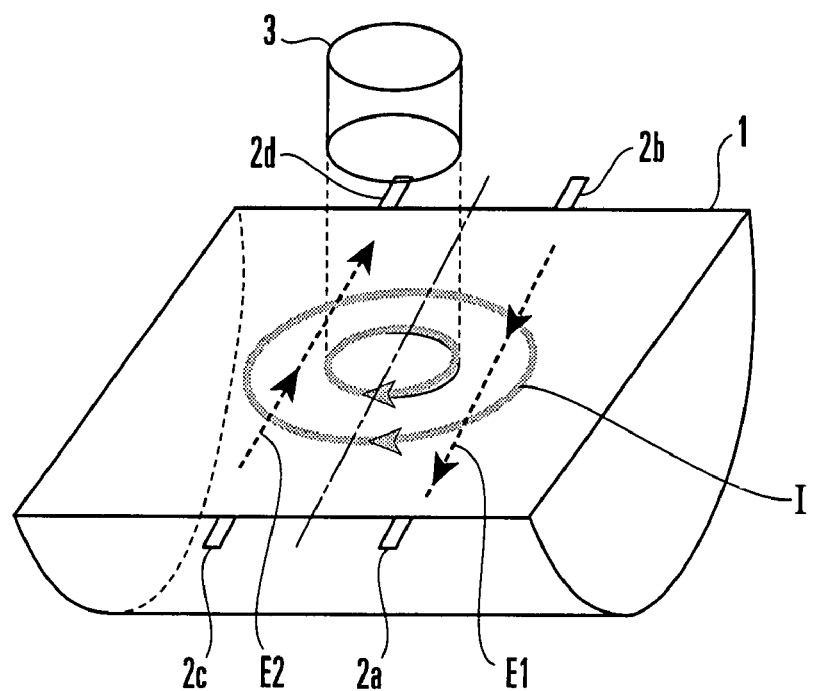
FIG. 14 is a view showing an eddy current and inter-electrode electromotive forces when the flow rate of a fluid to be measured is 0 in the state detection device shown in FIG. 13.

If the flow rate of the fluid to be measured is 0, a generated eddy current is only a component originating from a change in magnetic field. An eddy current I due to a change in the magnetic field Bd is directed as shown in FIG. 14. Therefore, a first inter-electrode electromotive force E1 which is generated between the electrodes 2a and 2b by a change in the magnetic field Bd and is irrelevant to the flow velocity within a plane including the electrode axis EAX1 and the measuring tube axis PAX and a second inter-electrode electromotive force E2 which is generated between the electrodes 2c and 2d by a change in the magnetic field Bd and is irrelevant to the flow velocity within a plane including the electrode axis EAX2 and the measuring tube axis PAX are directed opposite to each other as shown in FIG. 14.

At this time, the first and second inter-electrode electromotive forces E1 and E2 are the values obtained such that time derivatives (−dB3/dt and dB4/dt) of magnetic fields to which the directions of electromotive forces are added are multiplied by a proportional coefficient rk and the phase differences θ3 and θ4 are replaced with θ3+θ00 and θ4+θ00, respectively (rk and θ00 are associated with the conductivity and permittivity of the fluid to be measured and the structure of the measuring tube 1 including the positions of the electrodes 2a, 2b, 2c, and 2d) according to the following equations:

$$E1 = rk \cdot \omega 0 \cdot \cos(\omega 0 \cdot t) \cdot b3 \cdot \{-\sin(\theta 3 + \theta 00)\} + \quad (45)$$
$$rk \cdot \omega 0 \cdot \sin(\omega 0 \cdot t) \cdot b3 \cdot \{\cos(\theta 3 + \theta 00)\}$$

$$E2 = rk \cdot \omega 0 \cdot \cos(\omega 0 \cdot t) \cdot b4 \cdot \{\sin(\theta 4 + \theta 00)\} + \quad (46)$$
$$rk \cdot \omega 0 \cdot \sin(\omega 0 \cdot t) \cdot b4 \cdot \{-\cos(\theta 4 + \theta 00)\}$$

Figure 15:
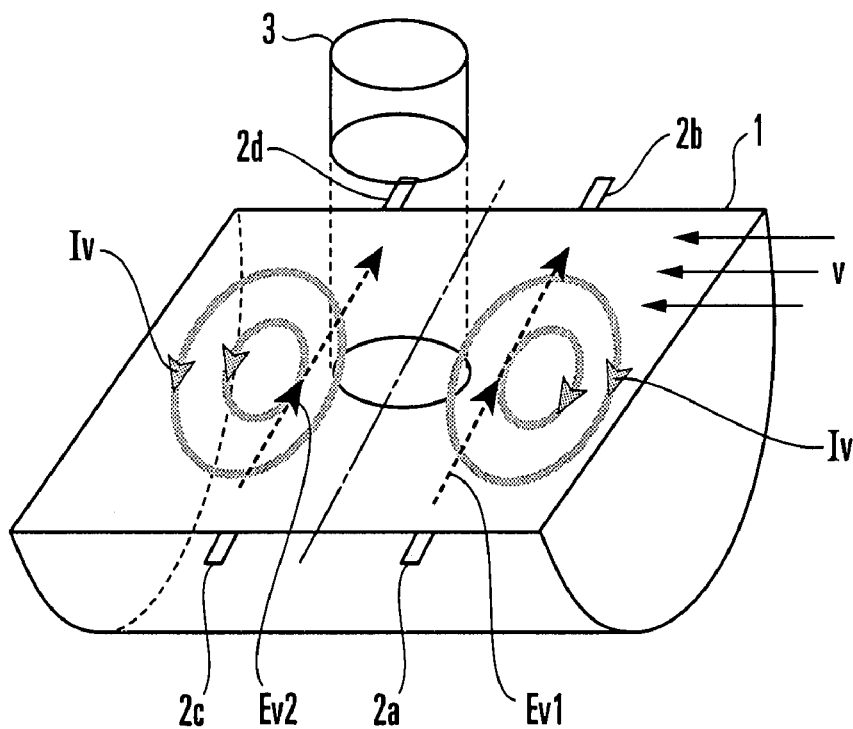
FIG. 15 is a view showing eddy currents and inter-electrode electromotive forces when the flow rate of a fluid to be measured is not 0 in the state detection device shown in FIG. 13.

If the magnitude of the flow velocity of the fluid to be measured is V (V≠0), a component v×Bd originating from a flow velocity vector v of the fluid to be measured is generated in the generated eddy current in addition to an eddy currents I generated when the flow velocity is 0. For this reason, an eddy current Iv originating from the flow velocity vector v and the magnetic field Bd is directed as shown in FIG. 15. Consequently, a first inter-electrode electromotive force Ev1 generated by the flow velocity vector v and the magnetic field Bd and a second inter-electrode electromotive force Ev2 generated by the flow velocity vector v and the magnetic field Bd are directed in the same direction.

At this time, the first and second inter-electrode electromotive forces Ev1 and Ev2 are the values obtained such that magnetic fields (B3 and B4) to which the directions of electromotive forces are added are multiplied by a proportional coefficient rkv and the phase differences θ3 and θ4 are replaced with θ3+θ01 and θ4+θ01, respectively (rkv and θ01 are associated with the magnitude V of the flow velocity, the conductivity and permittivity of the fluid to be measured, and the structure of the measuring tube 1 including the positions of the electrodes 2a, 2b, 2c, and 2d) according to the following equation:

$$Ev1 = \quad (47)$$
$$rkv \cdot \cos(\omega 0 \cdot t) \cdot b3 \cdot \cos(\theta 3 + \theta 01) + rkv \cdot \sin(\omega 0 \cdot t) \cdot b3 \cdot \sin(\theta 3 + \theta 01)$$

$$Ev2 = \quad (48)$$
$$rkv \cdot \cos(\omega 0 \cdot t) \cdot b4 \cdot \cos(\theta 4 + \theta 01) + rkv \cdot \sin(\omega 0 \cdot t) \cdot b4 \cdot \sin(\theta 4 + \theta 01)$$

Considering the directions of the inter-electrode electromotive forces described with reference to FIGS. 14 and 15, a first inter-electrode electromotive force Ea3c between the electrodes 2a and 2b which is obtained by combining the electromotive force obtained by converting the inter-electrode electromotive force originating from a temporal change in magnetic field into a complex vector and the electromotive force obtained by converting the inter-electrode electromotive force originating from the flow velocity of the fluid to be measured into a complex vector is represented by the following equation according to equation (18) using equation (17).

$$Ea3c = rk \cdot \omega 0 \cdot b3 \cdot \exp\{j \cdot (\pi/2 + \theta 3 + \theta 00)\} + \quad (49)$$
$$\gamma \cdot rk \cdot V \cdot b3 \cdot \exp\{j \cdot (\theta 3 + \theta 01)\}$$

In addition, a second inter-electrode electromotive force Ea4c between the electrodes 2c and 2d which is obtained by combining the electromotive force obtained by converting the inter-electrode electromotive force originating from a temporal change in magnetic field into a complex vector and the electromotive force obtained by converting the inter-electrode electromotive force originating from the flow velocity of the fluid to be measured into a complex vector is represented by the following equation according to equation (18) using equation (17).

$$Ea4c = rk \cdot \omega 0 \cdot b4 \cdot \exp\{j \cdot (-\pi/2 + \theta 4 + \theta 00)\} + \quad (50)$$
$$\gamma \cdot rk \cdot V \cdot b4 \cdot \exp\{j \cdot (\theta 4 + \theta 01)\}$$

Assume that θ4=θ3+Δθ4 represents the relationship between a phase lag θ3 of the magnetic field B3 with respect to ω0·t and a phase lag θ4 of the magnetic field B4 with respect to ω0·t, and θ01=θ00+Δθ01 represents the relationship between an angle θ00 of the ∂A/∂t component with respect to the imaginary axis and an angle θ01 of the v×B component with respect to the real axis. If E301 is a value obtained by substituting θ01=θ00+Δθ01 into the first inter-electrode electromotive force Ea3c given by equation (49), and E302 is a value obtained by substituting θ4=θ3+Δθ4 and θ01=θ00+Δθ01 into the second inter-electrode electromotive force Ea4c given by equation (50), the first and second inter-electrode electromotive forces E301 and E302 are represented as follows:

$$E301 = rk \cdot \omega 0 \cdot b3 \cdot \exp\{j \cdot (\pi/2 + \theta 3 + \theta 00)\} + \quad (51)$$
$$\gamma \cdot rk \cdot V \cdot b3 \cdot \exp\{j \cdot (\theta 3 + \theta 01)\}$$

$$E302 = rk \cdot \omega 0 \cdot b4 \cdot \exp\{j \cdot (-\pi/2 + \theta 3 + \Delta\theta 4 + \theta 00)\} + \quad (52)$$
$$\gamma \cdot rk \cdot V \cdot b4 \cdot \exp\{j \cdot (\theta 3 + \Delta\theta 4 + \theta 01)\}$$

A sum E30s and a difference E30d of the first and second inter-electrode electromotive forces E301 and E302 are represented by $$E30s = E301 + E302 \quad (53)$$
$$= rk \cdot \exp\{j \cdot (\theta 3 + \theta 00)\} \cdot$$
$$\exp(j \cdot \pi/2) \cdot \{b3 - b4 \cdot \exp(j \cdot \Delta\theta 4)\} \cdot \omega 0 +$$
$$rk \cdot \exp\{j \cdot (\theta 3 + \theta 00)\} \cdot$$
$$\gamma \cdot \exp(j \cdot \Delta\theta 01) \cdot \{b3 + b4 \cdot \exp(j \cdot \Delta\theta 4)\} \cdot V$$

$$E30d = E301 - E302 \quad (54)$$
$$= rk \cdot \exp\{j \cdot (\theta 3 + \theta 00)\} \cdot$$
$$\exp(j \cdot \pi/2) \cdot \{b3 + b4 \cdot \exp(j \cdot \Delta\theta 4)\} \cdot \omega 0 +$$
$$rk \cdot \exp\{j \cdot (\theta 3 + \theta 00)\} \cdot$$
$$\gamma \cdot \exp(j \cdot \Delta\theta 01) \cdot \{b3 - b4 \cdot \exp(j \cdot \Delta\theta 4)\} \cdot V$$

The first term of the right side of equation (53) represents a ∂A/∂t component in the sum of the electromotive force detected by the first electrodes 2a and 2b and the electromotive force detected by the second electrodes 2c and 2d. The second term of the right side of equation (53) represents a v×B component in the sum of the electromotive force detected by the first electrodes 2a and 2b and the electromotive force detected by the second electrodes 2c and 2d. The first term of the right side of equation (54) represents a ∂A/∂t component in the difference between the electromotive force detected by the first electrodes 2a and 2b and the electromotive force detected by the second electrodes 2c and 2d. The second term of the right side of equation (54) represents a v×B component in the difference between the electromotive force detected by the first electrodes 2a and 2b and the electromotive force detected by the second electrodes 2c and 2d.

In this case, if the distance d3 from the plane PLN3 including the axis of the exciting coil 3 to the electrode axis EAX1 connecting the electrodes 2a and 2b is almost equal to the distance d4 from the plane PLN3 to the electrode axis EAX2 connecting the electrodes 2c and 2d (d3≈d4), then b3≈b4 and Δθ4≈0. In this case, equations (53) and (54) are rewritten as follows:

$$E30s \approx rk \cdot \exp\{j \cdot (\theta 3 + \theta 00)\} \cdot \{(2 \cdot b3 \cdot \gamma \cdot V \exp(j \cdot \Delta\theta 01)\} \quad (55)$$

$$E30d \approx rk \cdot \exp\{j \cdot (\theta 3 + \theta 00)\} \cdot \{2 \cdot b3 \cdot \omega 0 \cdot \exp(j \cdot \pi/2)\} \quad (56)$$

That is, since the sum E30s of first and second inter-electrode electromotive forces is almost only the electromotive force based on the v×B component, and the difference E30d between the first and second inter-electrode electromotive forces is almost only the electromotive force based on the ∂A/∂t component, it is obvious that obtaining the difference between the first and second inter-electrode electromotive forces makes it possible to efficiently extract a ∂A/∂t component.

Assume that a ∂A/∂t component in the resultant vector of the first inter-electrode electromotive force E301 of equation (51) is represented by a product Va30 of constant term Ka=exp(j·π/2) in the ∂A/∂t component, term Bc3=b3·exp(j·θ3) associated with the magnetic field generated from the exciting coil 3, term C=rk·exp(j·θ00) associated with a characteristic or state of the fluid, and the angular frequency ω0. In this case, Va30 is represented by equation (57).

$$Va30=Ka \cdot Bc3 \cdot C \cdot \omega 0 \quad (57)$$

Assume that a v×B component in the resultant vector of the first inter-electrode electromotive force E301 of equation (51) is represented by a product Vb30 of constant term Kb=γ·exp(j·Δθ01) in the v×B component, term Bc3=b3·exp(j·θ3) associated with the magnetic field generated from the exciting coil 3, term C=rk·exp(j·θ00) associated with a characteristic or state of the fluid, and the magnitude V of the flow velocity. In this case, Vb30 is represented by equation (58).

$$Vb30=Kb \cdot Bc3 \cdot C \cdot V \quad (58)$$

Assume that a ∂A/∂t component in the resultant vector of the second inter-electrode electromotive force E302 of equation (52) is represented by a product Va40 of constant term −Ka=−exp(j·π/2) in the ∂A/∂t component, term Bc4=b4·exp{j·(θ3+Δθ4)} associated with the magnetic field generated from the exciting coil 3, term C=rk·exp(j·θ00) associated with the characteristic or state of the fluid, and the angular frequency ω0. In this case, Va40 is represented by equation (59).

$$Va40=-Ka \cdot Bc4 \cdot C \cdot \omega 0 \quad (59)$$

Considering that (E301−E302) when the difference between the first inter-electrode electromotive force E301 and the second inter-electrode electromotive force E302 is to be obtained, the equation obtained by reversing the sign of Va40 of equation (59) is defined as Va40R (Va40R=−Va40) represented by equation (60):

$$Va40R=Ka \cdot Bc4 \cdot C \cdot \omega 0 \quad (60)$$

Assume that a v×B component in the resultant vector of the second inter-electrode electromotive force E302 of equation (52) is represented by a product Vb40 of constant term Kb=γ·exp(j·Δθ01) in the v×B component, term Bc4=b4·exp{j·(θ3+Δθ4)} associated with the magnetic field generated from the exciting coil 3, term C=rk·exp(j·θ00) associated with a characteristic or state of the fluid, and the magnitude V of the flow velocity. In this case, Vb40 is represented by equation (61).

$$Vb40=Kb \cdot Bc4 \cdot C \cdot V \quad (61)$$

Considering that (E301−E302) when the difference between the first inter-electrode electromotive force E301 and the second inter-electrode electromotive force E302 is to be obtained, the equation obtained by reversing the sign of Vb40 of equation (61) is defined as Vb40R (Vb40R=−Vb40) represented by equation (62):

$$Vb40R=-Kb \cdot Bc4 \cdot C \cdot V \quad (62)$$

According to equations (57), (58), (60), and (62), in the electromotive force difference E30d represented, a ∂A/∂t component Va30+Va40R (the first term of the right side of equation (54)) originating from a change in the magnetic field generated from the exciting coil 3 and a v×B component Vb30+Vb40R (the second term of the right side of equation (54)) originating from the magnetic field generated from the exciting coil 3 and the flow velocity are given by $$Va30+Va40R=Ka \cdot (Bc3+Bc4) \cdot C \cdot \omega 0 \quad (63)$$

$$Vb30+Vb40R=Kb \cdot (Bc3-Bc4) \cdot C \cdot V \quad (64)$$

Extracting only the ∂A/∂t component (Va30+Va40R) from the resultant vector E30R (=Va30+Va40R+Vb30+Vb40R) of the ∂A/∂t component and v×B component and extracting the variation factor C due to a characteristic or state of the fluid make it possible to know a change in the characteristic or state of the fluid or the state in the measuring tube independently of the flow velocity.

A method of extracting a ∂A/∂t component from a resultant vector will be described next. A characteristic or state of a target fluid and a state in a measuring tube will be referred to as parameters hereinafter.

[First Extraction Method]

As an extraction method which can be applied to the three arrangements shown in FIGS. 1, 5, and 13, the first extraction method will be described. The first extraction method is a method using the phenomenon that although a ∂A/∂t component varies depending on the frequency, a v×B component does not vary. Note that in the first extraction method, a component C which varies depending on the value of a parameter needs to be associated with only the value of the parameter, and have no frequency characteristic.

First of all, in the arrangement shown in FIG. 1, when an exciting current with the angular frequency ω0 is supplied to the exciting coil 3, the electromotive force detected by the electrodes 2a and 2b corresponds to the resultant vector Va10+Vb10 of the vector Va10 of the ∂A/∂t component and the vector Vb10 of the v×B component according to the following equations.

$$Va10=Ka \cdot B1c \cdot C \cdot \omega 0 \quad (65)$$

$$Vb10=Kb \cdot B1c \cdot C \cdot V \quad (66)$$

In consideration of the fact that a ∂A/∂t component is a vector irrelevant to the magnitude V of the flow velocity and a v×B component is a vector which changes in magnitude in proportion to the magnitude V of the flow velocity, taking the difference between a resultant vector obtained with an exciting angular frequency ω2 different from ω0 and a resultant vector obtained with the exciting angular frequency ω0 cancels out the v×B component. As a consequence, the ∂A/∂t component is left.

A v×B component obtained with the exciting angular frequency ω2 is equal to that in equation (66). A ∂A/∂t component obtained with the exciting angular frequency ω2 is given by the equation obtained by replacing ω0 with ω2 in equation (65) as follows:

$$Va12=Ka \cdot B1c \cdot C \cdot \omega 2 \quad (67)$$

Figure 16:
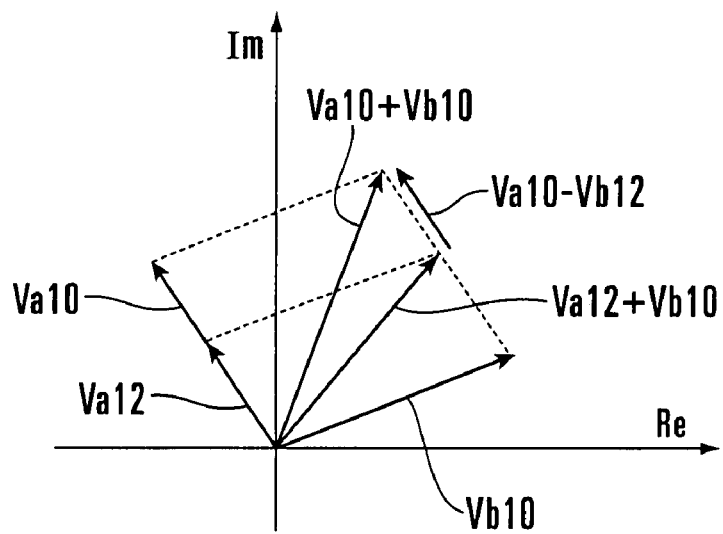
FIG. 16 is a graph showing processing of extracting a ∂A/∂t component vector in the form of a complex vector in the state detection device shown in FIG. 1.

Subtracting the resultant vector Va12+Vb10 obtained with the exciting angular frequency ω2 from the resultant vector Va10+Vb10 obtained with the exciting angular frequency ω0 cancels out the v×B component, and becomes equal to Va10–Va12. The ∂A/∂t component Va10–Va12 irrelevant to the flow velocity can therefore be extracted by using the output difference between different frequency components. FIG. 16 is a graph showing the processing of extracting the ∂A/∂t component Va10–Va12 in the form of a complex vector.

In the arrangement shown in FIG. 5, as described above, keeping the phase difference between the magnetic field generated from the first exciting coil 3a and the magnetic field generated from the second exciting coil 3b at almost π makes it possible to efficiently extract a ∂A/∂t component. Assume that the first exciting current having the angular frequency ω0 is supplied to the first exciting coil 3a, and the second exciting current having the angular frequency ω0 with a phase difference Δθ2+π with respect to the first exciting current is supplied to the second exciting coil 3b. In this case, letting Vas0R be the vector Va10+Va20R of the ∂A/∂t component in equation (39) and Vbs0R be the vector Vb10+Vb20R of the v×B component in equation (40), the electromotive force detected by the electrodes 2a and 2b corresponds to a resultant vector Vas0R+Vbs0R given below:

$$Vas0R=Ka \cdot (B1c+B2c) \cdot C \cdot \omega 0 \quad (68)$$

$$Vbs0R=Kb \cdot (B1c-B2c) \cdot C \cdot V \quad (69)$$

As shown in FIG. 1, a v×B component obtained when the exciting angular frequency is set to ω2 becomes equal to equation (69). In addition, a vector Vas2R of a ∂A/∂t component obtained when the exciting angular frequency is set to ω2 becomes equal to the value obtained by replacing ω0 with ω2 in equation (68) according to the following equation:

$$Vas2R=Ka \cdot (B1c+B2c) \cdot C \cdot \omega 2 \quad (70)$$

Figure 17:
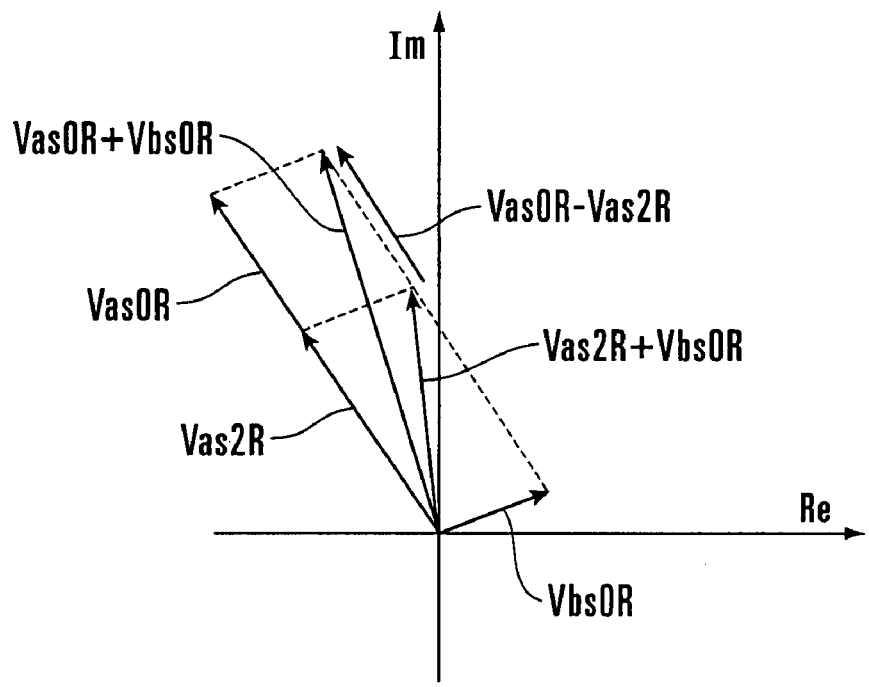
FIG. 17 is a graph showing processing of extracting a ∂A/∂t component vector in the form of a complex vector in the state detection device shown in FIG. 5.

Subtracting the resultant vector Vas2R+Vbs0R obtained with the exciting angular frequency ω2 from the resultant vector Vas0R+Vbs0R obtained with the exciting angular frequency ω0 cancels out the v×B component, and becomes equal to Vas0R–Vas2R. The ∂A/∂t component Vas0R–Vas2R irrelevant to the flow velocity can therefore be extracted by using the output difference between different frequency components. FIG. 17 is a graph showing the processing of extracting the ∂A/∂t component Vas0R–Vas2R in the form of a complex vector.

In the arrangement shown in FIG. 13, the method of extracting a ∂A/∂t component from a resultant vector is the same as that in the arrangement shown in FIG. 5. The extraction method described in the case of the state detection device shown in FIG. 5 may be made to correspond to the state detection device shown in FIG. 13 by replacing the electromotive force originating from the influence of the magnetic field generated from the first exciting coil 3a with the electromotive force detected by the first electrodes 2a and 2b, replacing the electromotive force originating from the influence of the magnetic field generated from the second exciting coil 3b with the electromotive force detected by the second electrodes 2c and 2d, replacing the electromotive force detected in the excitation state ST1 with an electromotive force sum, and replacing the electromotive force detected in the excitation state ST2 with an electromotive force difference.

[Second Extraction Method]

The second extraction method will be described as an extraction method which can be applied to the arrangements shown in FIGS. 5 and 13 of the three arrangements shown in FIGS. 1, 5, and 13. The second extraction method is a method of canceling v×B components by using the phenomenon that v×B components are directed in the same direction on the front and rear sides in the tube axis direction with respect to a plane which includes the exciting coil and is perpendicular to the tube axis direction, but ∂A/∂t components are directed in opposite directions.

In the case of the arrangement shown in FIG. 5, as described above, keeping the phase difference between the magnetic field generated from the first exciting coil 3a and the magnetic field generated from the second exciting coil 3b at almost π makes it possible to efficiently extract a ∂A/∂t component. The ∂A/∂t component vector Vas0R is extracted from the resultant vector Vas0R+Vbs0R in the same manner as in the first extraction method. If Vas0R>>Vbs0R, then Vbs0R≈0, thus approximately extracting the ∂A/∂t component vector Vas0R.

In the initial state (at the time of calibration), if the magnetic field B1 generated from the first exciting coil 3a and the magnetic field B2 generated from the second exciting coil 3b are set to be equal in advance, the differences between the magnetic fields B1 and B2 and those in the initial state decrease. As a consequence, the condition represented by the following expression holds.

$$|b1+b2\cdot\exp(j\cdot\Delta\theta 2)|>>|b1-b2\cdot\exp(j\cdot\Delta\theta 2)| \quad (71)$$

Since ω0>γ·V holds, the following condition holds for the inter-electrode electromotive force E20R given by equation (30) in consideration of the condition represented by equation (71).

$$|\omega 0\cdot\exp(j\cdot\pi/2)\cdot\{b1+b2\cdot\exp(j\cdot\Delta\theta 2)\}|>>|\gamma\cdot V\cdot\exp(j\cdot\Delta\theta 01)\cdot\{b1-b2\cdot\exp(j\cdot\Delta\theta 2)\}| \quad (72)$$

Letting Vas0R′ be the electromotive force obtained by approximating the inter-electrode electromotive force E20R given by equation (30) by using the condition represented by expression (72), the inter-electrode electromotive force Vas0R′ is represented by $$Vas0R' \approx Vas0R + Vbs0R \quad (73)$$

$$Vas0R' = rk\cdot\exp\{j\cdot(\theta 1+\theta 00)\}\cdot \quad (74)$$
$$\omega 0\cdot\exp(j\cdot\pi/2)\cdot\{b1+b2\cdot\exp(j\cdot\Delta\theta 2)\}$$
$$= Vas0R$$

Obviously, therefore, using the phase difference between the magnetic field generated from the first exciting coil 3a and the magnetic field generated from the second exciting coil 3b makes it possible to extract the ∂A/∂t component vector Vas0R in the resultant vector Vas0R+Vbs0R.

In the arrangement shown in FIG. 13, a method of extracting the ∂A/∂t component from the resultant vector is the same as that in the arrangement shown in FIG. 5 as described in the first extraction method. In the arrangement shown in FIG. 13, using the output difference between the first electrodes 2a and 2b and the second electrodes 2c and 2d makes it possible to extract the ∂A/∂t component vector Vas0R from the resultant vector Vas0R+Vbs0R.

A method of extracting the above-described parameter from the extracted ∂A/∂t component will be described next. The parameter in the ∂A/∂t component includes the first parameter whose variation factor is irrelevant to the frequency (i.e., the influence of the frequency can be ignored), and the second parameter whose variation factor is relevant to the frequency.

[First Parameter Extraction Method]

The ∂A/∂t component extracted in the arrangement shown in FIG. 1 by the first extraction method is a vector Va10−Va12. The ∂A/∂t component extracted in the arrangement shown in FIG. 5 is a vector Vas0R−Vas2R. Since the extracted ∂A/∂t component is irrelevant to the flow velocity V, the characteristic or state of the fluid or a state in the measuring tube, other than the flow velocity, can be measured by using the ∂A/∂t component. Since it is possible to extract the first parameter in either of the vectors Va10−Va12 and Vas0R−Vas2R by the same method as described above, a case wherein the first parameter is extracted from the vector Vas0R−Vas2R will be exemplified.

In the vector Vas0R−Vas2R, C=rk·exp(j·θ00) represents the variation factor which changes depending on the target first parameter. A proportional coefficient rk and the angle θ00 of the ∂A/∂t component with respect to an imaginary axis are represented as functions of the first parameter p, i.e., rk[p] and θ00[p], respectively. If the variation factor C is Cp when the first parameter is p, the variation factor Cp is given by $$Cp=rk[p]\cdot\exp(j\cdot\theta 00[p]) \quad (75)$$

According to equations (68) and (70), the vector Vas0R−vas2R is expressed by $$Vas0R-Vas2R=Ka\cdot(B1c+B2c)\cdot Cp\cdot(\omega 0-\omega 2) \quad (76)$$

According to equation (76), the variation factor Cp which changes depending on the target first parameter is expressed by $$Cp=\{Vas0R-Vas2R\}/\{Ka\cdot(B1c+B2c)\cdot(\omega 0-\omega 2)\} \quad (77)$$

In this case, when a magnetic field whose amplitude or phase does not vary is to be generated by using a proper exciting coil, terms B1c and B2c associated with the magnetic field in a ∂A/∂t component become values which can be checked at the time of calibration, and the magnitude of {Vas0R−Vas2R}/{Ka·(B1c+B2c)·(ω0−ω2)} and the angle of {Vas0R−Vas2R}/{Ka·(B1c+B2c)·(ω0−ω2)} with respect to the real axis are respectively represented by rk[p] and θ00[p]. Therefore, storing the relationship between the first parameter p and the proportional coefficient rk[p] or the relationship between the first parameter p and the angle θ00[p] in advance at the time of calibration makes it possible to obtain the first parameter p by calculating the magnitude or phase of {Vas0R−Vas2R}/{Ka·(B1c+B2c)·(ω0−ω2)}. Since the first parameter p does not change depending on the frequency, the first parameter p can be obtained by using an arbitrary frequency.

[Second Parameter Extraction Method]

The ∂A/∂t component extracted in the arrangement shown in FIG. 5 by the second extraction method is a vector Vas0R in equation (68). Since the extracted ∂A/∂t component is irrelevant to the flow velocity V, the characteristic or state of the fluid or a state in the measuring tube, other than the flow velocity, can be measured by using the ∂A/∂t component. In the vector Vas0R in equation (68), C=rk·exp(j·θ00) represents the variation factor which changes depending on the target second parameter. A proportional coefficient rk and the angle θ00 of the ∂A/∂t component with respect to an imaginary axis are represented as functions of the second parameter p and angular frequency ω, i.e., rk[p,ω] and θ00[p,ω], respectively. If the variation factor C is Cp when the second parameter is p, and the angular frequency is ω0, the variation factor Cp0 is given by $$Cp0=rk[p,\omega 0]\cdot\exp(j\cdot\theta 00[p,\omega 0]) \quad (78)$$

According to equation (68), the vector Vas0R is expressed by $$Vas0R=Ka\cdot(B1c+B2c)\cdot Cp0\cdot\omega 0 \quad (79)$$

According to equation (79), the variation factor Cp0 which changes depending on the target second parameter is expressed by $$Cp0=Vas0R/\{Ka\cdot(B1c+B2c)\cdot\omega 0\} \quad (80)$$

In this case, when a magnetic field whose amplitude or phase does not vary is to be generated by using a proper exciting coil, terms B1c and B2c associated with the magnetic field in a ∂A/∂t component become values which can be checked at the time of calibration, and the magnitude of Vas0R/{Ka·(B1c+B2c)·ω0} and the angle of Vas0R/{Ka·(B1c+B2c)·ω0} with respect to the real axis are respectively represented by rk[p,ω0] and θ00[p,ω0]. Therefore, storing the relationship between the second parameter p and the proportional coefficient rk[p,ω0] or the relationship between the second parameter p and the angle θ00[p,ω0] with the exciting angular frequency ω0 in advance at the time of calibration makes it possible to obtain the second parameter p by calculating the magnitude or phase of Vas0R/{Ka·(B1c+B2c)·ω0}.

When the exciting frequency is fixed to one level, a method of obtaining the second parameter is the same as that of the first parameter. Hence, a case wherein the value of the second parameter is output in consideration of variation of the magnetic field will be exemplified as a case wherein the exciting frequency is not fixed to one level. In this case, the variation factor of the magnetic field can be removed, and the value of the second parameter with a small error can be output by obtaining the ∂A/∂t components with a plurality of frequencies.

In the vector Vas2R in equation (70), when the value of the variation factor C with the exciting angular frequency ω2 is Cp2, the variation factor Cp2 and vector Vas2R are expressed by the following equation according to equations (78) and (79).

$$Cp2=rk[p,\omega 2]\cdot\exp(j\cdot\theta 00[p,\omega 2]) \tag{81}$$

$$Vas2R=Ka\cdot(B1c+B2c)\cdot Cp0\cdot\omega 2 \tag{82}$$

According to equation (82), the variation factor Cp2 which changes depending on the target second parameter is expressed by the following equation.

$$Cp2=Vas2R\{Ka\cdot(B1c+B2c)\cdot\omega 2\} \tag{83}$$

When Cp0≠Cp2 holds, and the ratio between the variation factors Cp0 and Cp2 is Cn, the ratio Cn is expressed by the following equation according to equations (78), (80), (81), and (83).

$$\begin{aligned}Cn &= Cp2/Cp0 \\ &= \{rk[p,\omega 2]/rk[p,\omega 0]\}\cdot \\ &\quad \exp\{j\cdot(\theta 00[p,\omega 2]-\theta 00[p,\omega 0])\} \\ &= (Vas2R/Vas0R)\cdot(\omega 0/\omega 2)\end{aligned} \tag{84}$$

According to equation (84), the ratio Cn does not have the variation factor of the magnetic field, and the second parameter p can be obtained by reducing the error factor. At the time of calibration, storing the relationship among the exciting angular frequencies ω0 and ω2, the second parameter p, and {rk[p,ω2]/rk[p,ω0]}, or storing the relationship among the exciting angular frequencies ω0 and ω2, the second parameter p, and (θ00[p,ω2]−θ00[p,ω0]) makes it possible to obtain the second parameter p without the variation factor of the magnetic field (e.g., the shift of the magnetic field) by calculating the magnitude or phase of (Vas2R/Vas0R)·(ω0/ω2).

A case wherein the plurality of second parameter values are obtained will be described next. When the frequency characteristics of the parameters depending on the parameters are different from each other, obtaining the ∂A/∂t components with the plurality of exciting angular frequencies makes it possible to obtain the plurality of second parameter values. In this case, two second parameter values are obtained. Of the two parameters, one is the third parameter, and the other is the fourth parameter.

In the vector Vas0R in equation (68), C=rk·exp(j·θ00) represents the variation factor which changes depending on the target second parameter. A proportional coefficient rk and the angle θ00 of the ∂A/∂t component with respect to an imaginary axis are represented as functions of the third parameter p, the fourth parameter q, and the angular frequency ω, i.e., rk[p,q,ω] and θ00[p,q,ω], respectively. If the variation factor C is Cpq0 when the third parameter is p, the fourth parameter is q, and the angular frequency is ω, the variation factor Cpq0 is given by $$Cpq0=rk[p,q,\omega 0]\cdot\exp(j\cdot\theta 00[p,q,\omega 0]) \tag{85}$$

According to equation (68), the vector Vas0R is expressed by $$Vas0R=Ka\cdot(B1c+B2c)\cdot Cpq0\cdot\omega 0 \tag{86}$$

According to equation (86), the variation factor Cpq0 which changes depending on the target third and fourth parameters is expressed by $$Cpq0=Vas0R/\{Ka\cdot(B1c+B2c)\cdot\omega 0\} \tag{87}$$

If the value of the variation factor C is Cpq2 when the third parameter is p, the fourth partaker is q, and the angular frequency is ω2, the variation factor Cpq2 and the vector Vas2R are expressed by the following equations according to equations (85) and (86).

$$Cpq2=rk[p,q,\omega 2]\cdot\exp(j\cdot\theta 00[p,q,\omega 2]) \tag{88}$$

$$Vas2R=Ka\cdot(B1c+B2c)\cdot Cpq2\cdot\omega 2 \tag{89}$$

According to equation (89), the variation factor Cpq2 which changes depending on the target third and fourth parameters is expressed by following equation.

$$Cpq2=Vas2R/\{Ka\cdot(B1c+B2c)\cdot\omega 2\} \tag{90}$$

When Cpq1≠Cpq2 holds, two variation factors Cpq0 and Cpq2 are obtained.

In this case, when a magnetic field whose amplitude or phase does not vary is to be generated by using a proper exciting coil, terms B1c and B2c associated with the magnetic field in a ∂A/∂t component become values which can be checked at the time of calibration, and the magnitude of Vas0R/{Ka·(B1c+B2c)·ω0} and the angle of Vas0R/{Ka·(B1c+B2c)·ω0} with respect to the real axis are respectively represented by rkg[p,q,ω0] and θ00[p,q,ω0], and the magnitude of Vas2R/{Ka·(B1c+B2c)·ω2} and the angle of Vas2R/{Ka·(B1c+B2c)·ω2} with respect to the real axis are respectively represented by rkg[p,q,ω2] and θ00[p,q,ω2].

Therefore, storing the relationship among the third parameter p, the fourth parameter q, and the proportional coefficient [p,q,ω0] obtained with the exciting angular frequency ω0, and the relationship among the third parameter p, the fourth parameter q, and the proportional coefficient [p,q,ω2] obtained with the exciting angular frequency ω2 make it possible to obtain the third parameter p and the fourth parameter q by calculating the magnitudes of Vas0R/{Ka·(B1c+B2c)·ω0} and Vas2R/{Ka·(B1c+B2c)·ω2}.

Storing the relationship among the third parameter p, the fourth parameter q, and the angle θ00[p,q,ω0] obtained with the exciting angular frequency ω0, and the relationship among the third parameter p, the fourth parameter q, and the angle θ00[p,q,ω2] obtained with the exciting angular frequency ω2 in advance at the time of calibration make it possible to obtain the third and fourth parameters p and q by calculating the phases of Vas0R/{Ka·(B1c+B2c)·ω0} and Vas2R/{Ka·(B1c+B2c)·ω2}.

Points of concern to be raised at the time of implementation will be described next. In order to obtain the value of the parameter p from the proportional coefficient rk[p] and rk[p,ω] obtained from a measured value, it is necessary to generate a table for inversion in advance. The proportional coefficient rk[p] and angle θ00[p] will be representatively expressed by a function f[p], the proportional coefficient rk[p,ω] and angle θ00[p,ω] will be representatively expressed by a function f[p,ω] (when a plurality of parameters are used, a function f[p,q,ω]), and inversion and a table will be described. There are two methods of generating a table for inversion, i.e., a method (to be referred to as the first generating method hereinafter) of generating a table by interpolation from a measurement result at the time of calibration, and a method (to be referred to as the second generating method hereinafter) of directly generating a table from a theoretical formula.

Figure 18:
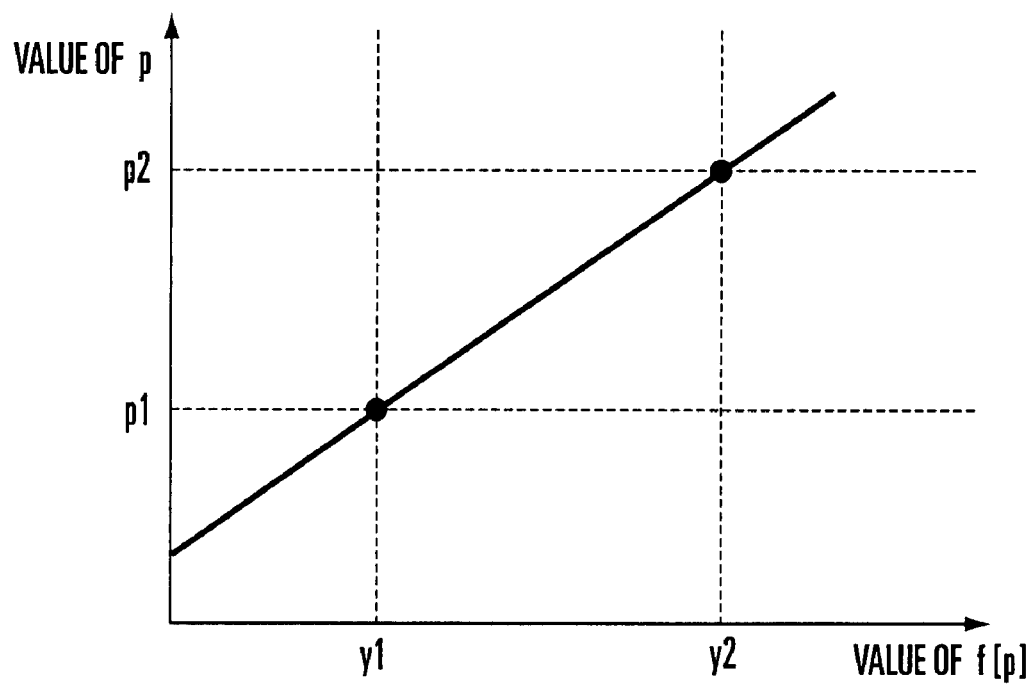
FIG. 18 is a graph for explaining a method of generating the first table in the state detection device of the present invention.

The first generating method for a table (to be referred to as the first table hereinafter) for the extraction of the first parameter will be described first. As shown in FIG. 18, assuming that f[p1]=y1 was obtained as a measurement result when the value of the first parameter was p1 at the time of calibration, and f[p2]=y2 was obtained as a measurement result when the value of the first parameter was p2, the first parameter p is represented by the following equation by linear approximation between two points:

$$p=(p2-p1)/(y2-y1)\cdot(f[p]-y1)+p1 \qquad (91)$$

The first table can be generated by equation (91). Using the first table makes it possible to obtain the first parameter p from the function f[p] (the proportional coefficient rk[p] or angle θ00[p]) obtained at the time of actual measurement after calibration. Although the linear approximation has been exemplified, a polynomial also allows inversion in the same manner as described above.

The second generating method for the first table will be described next. If the relationship between the first parameter p and y=f[p] is obtained as a theoretical formula at the time of design, and there is an inverse function $f^{-1}(y)$, the first parameter p is represented by $$p=f^{-1}(f[p]) \qquad (92)$$

Figure 19:
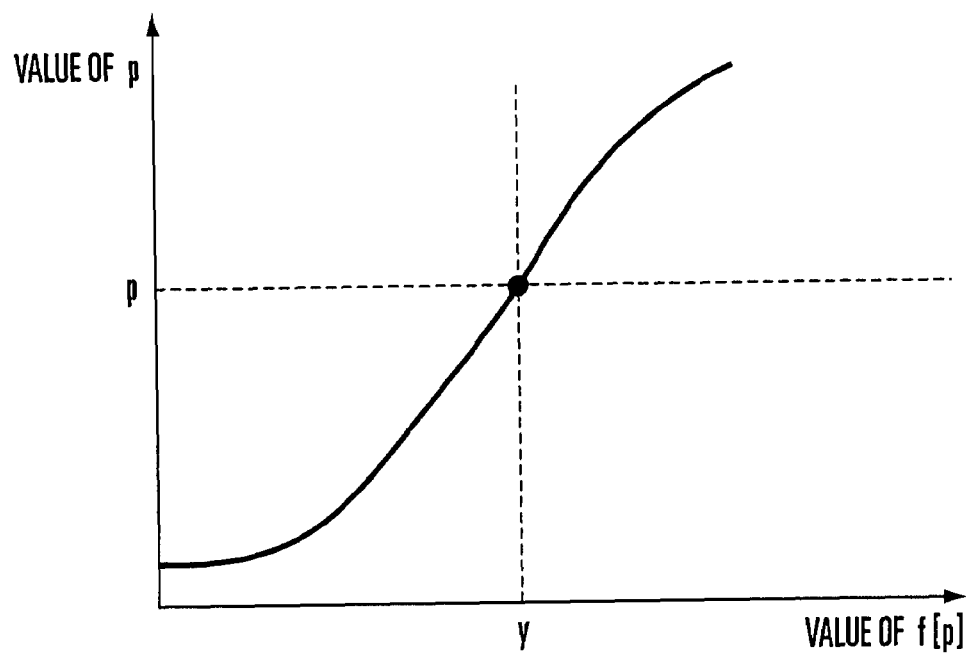
FIG. 19 is a graph for explaining another method of generating the first table in the state detection device of the present invention.

FIG. 19 shows the relationship represented by equation (92). Storing equation (92) as the first table in advance makes it possible to obtain the first parameter p from the function f[p] obtained at the time of actual measurement after calibration.

Figure 20:
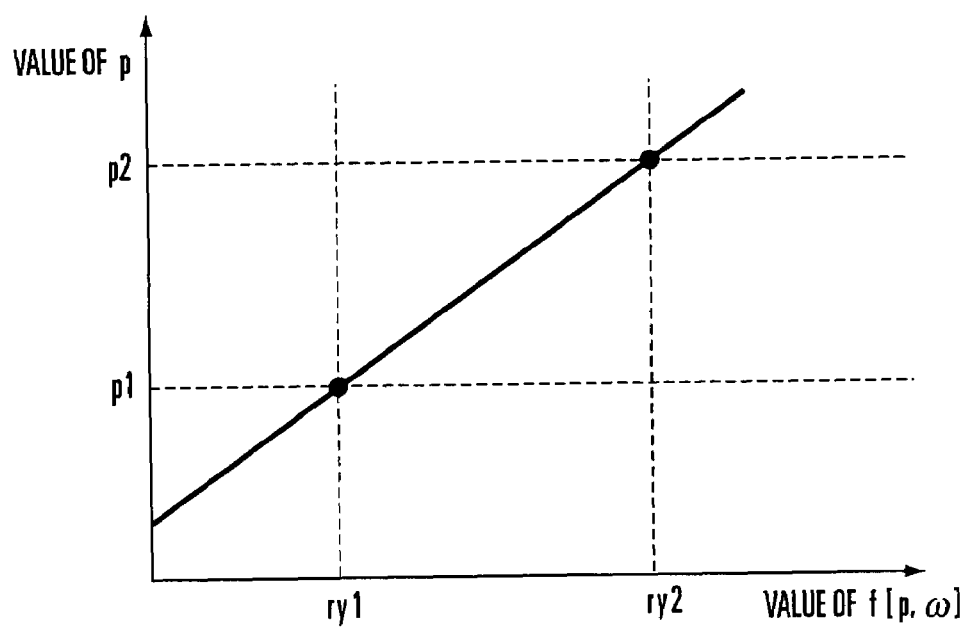
FIG. 20 is a graph for explaining a method of generating the second table in the state detection device of the present invention.

The first generating method for a table (to be referred to as the second table hereinafter) for the extraction of one second parameter will be described next. As shown in FIG. 20, assuming that the ratio ry1 between f[p1,ω0] with the exciting angular frequency ω0 and f[p1,ω2] with the exciting angular frequency ω2 is obtained as a measurement result when the value of the second parameter was p1 at the time of calibration, and the ratio ry2 between f[p2,ω0] with the exciting angular frequency ω0 and f[p2,ω2] with the exciting angular frequency ω2 is obtained as a measurement result when the value of the second parameter was p2, the second parameter p is represented by the following equation by linear approximation between two points:

$$p = (p2 - p1)/(ry2 - ry1)\cdot(f[p,\omega 2]/f[p,\omega 0] - ry1) + p1 \qquad (93)$$

The second table can be generated by equation (93). Using the second table makes it possible to obtain the second parameter p from the ratio f[p,ω2]/f[p,ω0] of the functions obtained at the time of actual measurement after calibration. The function f[p,ω2] means the proportional coefficient rk[p,ω2] or angle θ00[p,ω2], and the function f[p,ω0] means the proportional coefficient rk[p,ω0] or angle θ00[p,ω0]. Although the linear approximation has been exemplified, a polynomial also allows inversion in the same manner as described above.

The second generating method for the second table will be described next. If the relationship between the second parameter p and y=f[p,ω] with the exciting angular frequency G) is obtained as a theoretical formula at the time of design, and the ratio f[p,ω0]/f[p,ω2] of the function is represented by ry=g[p], when there is an inverse function $g^{-1}(p)$, the second parameter p is represented by $$p=g^{-1}(g[p]) \qquad (94)$$

FIG. 21 shows the relationship represented by equation (94). Storing equation (94) as the second table in advance makes it possible to obtain the second parameter p from the ratio f[p,ω2]/f[p,ω0] of the function obtained at the time of actual measurement after calibration.

The first generating method for a table (to be referred to as the third table hereinafter) for the extraction of a plurality of second parameters will be described next. In this case, the values of two second parameters are obtained. Of the two second parameters, one is the third parameter, and the other is the fourth parameter. As shown in FIG. 22, assume that, with the exciting angular frequency ω0 at the time of calibration, f[p1,q1,ω0]=z11 is obtained as a measurement result when the third parameter is p1 and the fourth parameter is q1, f[p1,q2,ω0]=z12 is obtained as a measurement result when the third partaker is p1 and the fourth parameter is q2, f[p2,q1,ω0]=z21 is obtained as a measurement result when the third parameter is p2 and the fourth parameter is q1, and f[p2,q2,ω0]=z22 is obtained as a measurement result when the third parameter is p2 and the fourth parameter is q2. In this case, a plane including arbitrary three points out of the measurement results z11, z12, z21, and z22 is expressed by the following equation.

$$p/a0+q/b0+f[p,q,\omega 0]/c0=1 \qquad (95)$$

In equation (95), a0, b0, and c0 are intercepts on axes p, q, and f[p,q,ω0], respectively.

As shown in FIG. 23, assume that, with the exciting angular frequency ω2 at the time of calibration, f[p1,q1,ω2]=z11' is obtained as a measurement result when the third parameter is p1 and the fourth parameter is q1, f[p1,q2,ω2]=z12' is obtained as a measurement result when the third parameter is p1 and the fourth parameter is q2, f[p2,q1,ω2]=z21' is obtained as a measurement result when the third parameter is p2 and the fourth parameter is q1, and f[p2,q2,ω2]=z22' is obtained as a measurement result when the third parameter is p2 and the fourth parameter is q2. In this case, a plane including arbitrary three points out of the measurement results z11', z12', z21', and z22' is expressed by the following equation.

$$p/a2+q/b2+f[p,q,\omega 2]/c2=1 \qquad (96)$$

In equation (96), a2, b2, and c2 are intercepts on axes p, q, and f[p,q,ω0], respectively.

Storing the equations (95) and (96) of the plane as the third table makes it possible to define the third parameter p and the fourth parameter q as an intersection of the following two lines from the functions f[p,q,ω0]=z and f[p,q,ω2] obtained at the time of actual measurement after calibration.

$$p/a0+q/b0+z0/c0=1 \qquad (97)$$

$$p/a2+q/b2+z2/c2=1 \qquad (98)$$

FIG. 24 shows an example of the lines expressed by equations (97) and (98). For example, the solutions of the third parameter p and the fourth parameter q can be obtained by the Gaussian elimination method using simultaneous equations of equations (97) and (98). Although approximation is performed by using a plane, inverse transformation can also be performed by using a curved plane.

Figure 25:
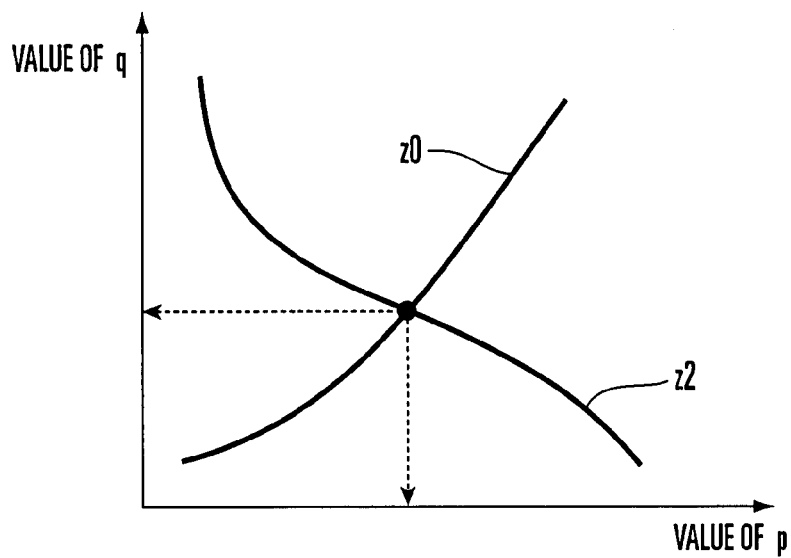
FIG. 25 is a graph for explaining another method of generating the third table in the state detection device of the present invention.

The second generating method for the third table will be described next. When the relationship among the third parameter p, the fourth parameter q, $z0=f[p,q,\omega0]$ with the exciting angular frequency $\omega0$, and $z2=f[p,q,\omega2]$ with the exciting angular frequency $\omega2$ is obtained as a theoretical formula at the time of design, a curved plane equation can be obtained as the third table. Storing the third table makes it possible to obtain two curved line equations from the functions $f[p,q,\omega0]$ and $f[p,q,\omega2]$ obtained at the time of actual measurement after calibration. The third parameter p and the fourth parameter q are obtained as the intersection of the two curved lines. An example of two curved lines is shown in FIG. 25.

FIRST EMBODIMENT

The first embodiment of the present invention will be described in detail next. This embodiment uses the first principle described above. A state detection device according to this embodiment includes one exciting coil and a pair of electrodes, and has the same arrangement as that of the state detection device shown in FIG. 1 except for the signal processing system. The principle of this embodiment will therefore be described by using reference numerals in FIG. 1. This embodiment uses the first extraction method as a method of extracting a $\partial A/\partial t$ component from a resultant vector, and obtains the first parameter irrelevant to an exciting frequency. An example of the first parameter is the level of a fluid or the deposited state of a substance adhering to the inside of a measuring tube.

When an exciting current with an angular frequency $\omega0$ is supplied to an exciting coil 3, and the first parameter is p1, an inter-electrode electromotive force E110 is represented by the following equation according to equations (19), (65), and (75).

$$E110 = rk[p1] \cdot \omega0 \cdot b1 \cdot \exp\{j \cdot (\pi/2 + \theta1 + \theta00[p1])\} + \gamma \cdot rk[p1] \cdot V \cdot b1 \cdot \exp\{j \cdot (\theta1 + \theta00[p1] + \Delta\theta01)\} \quad (99)$$

When an exciting current with an angular frequency $\omega2$ is supplied to the exciting coil 3, and the first parameter is p1, an inter-electrode electromotive force E112 is represented by the following equation according to equations (19), (67), and (75).

$$E112 = rk[p1] \cdot \omega2 \cdot b1 \cdot \exp\{j \cdot (\pi/2 + \theta1 + \theta00[p1])\} + \gamma \cdot rk[p1] \cdot V \cdot b1 \cdot \exp\{j \cdot (\theta1 + \theta00[p1] + \Delta\theta01)\} \quad (100)$$

Letting EdA1 be the difference between the inter-electrode electromotive forces E110 and E112, the electromotive force difference EdA1 is given by $$EdA1 = E110 - E112 \\ = rk[p1] \cdot \exp(j \cdot \theta00[p1]) \cdot b1 \cdot \exp\{j \cdot (\pi/2 + \theta1)\} \cdot (\omega0 - \omega2) \quad (101)$$

According to equation (101), it is obvious that a $\partial A/\partial t$ component in a resultant vector can be extracted by using the output difference between different frequency components. Equation (101) is irrelevant to a magnitude V of the flow velocity, and hence is only the component generated by $\partial A/\partial t$. Using the electromotive force difference EdA1, therefore, makes it possible to measure a state of the fluid or a state in the measuring tube other than the flow velocity.

When a variation factor dependent on the first parameter is Cp1, $Cp1=rk[p1] \cdot \exp(j \cdot \theta00[p1])$ holds, and the remaining portion is a constant which is provided at the time of calibration. The variation factor Cp1 is represented by equation (101).

$$Cp1=EdA1/[b1 \cdot \exp\{j \cdot (\pi/2+\theta1)\} \cdot (\omega0-\omega2)] \quad (102)$$

According to equation (102), a magnitude rk[p1] of the variation factor Cp1 and an angle $\theta00$ [p1] thereof from the real axis are represented by $$rk[p1]=|EdA1|/\{b1 \cdot (\omega0-\omega2)\} \quad (103)$$

$$\theta00[p1]=\angle EdA1-(\pi/2+\theta1) \quad (104)$$

The first parameter p1 can be obtained from the relationship between the first parameter p1 and rk[p1], which is checked in advance by measurement or the like at the time of calibration, or the relationship between the first parameter p1 and the angle $\theta00[p1]$.

Figure 26:
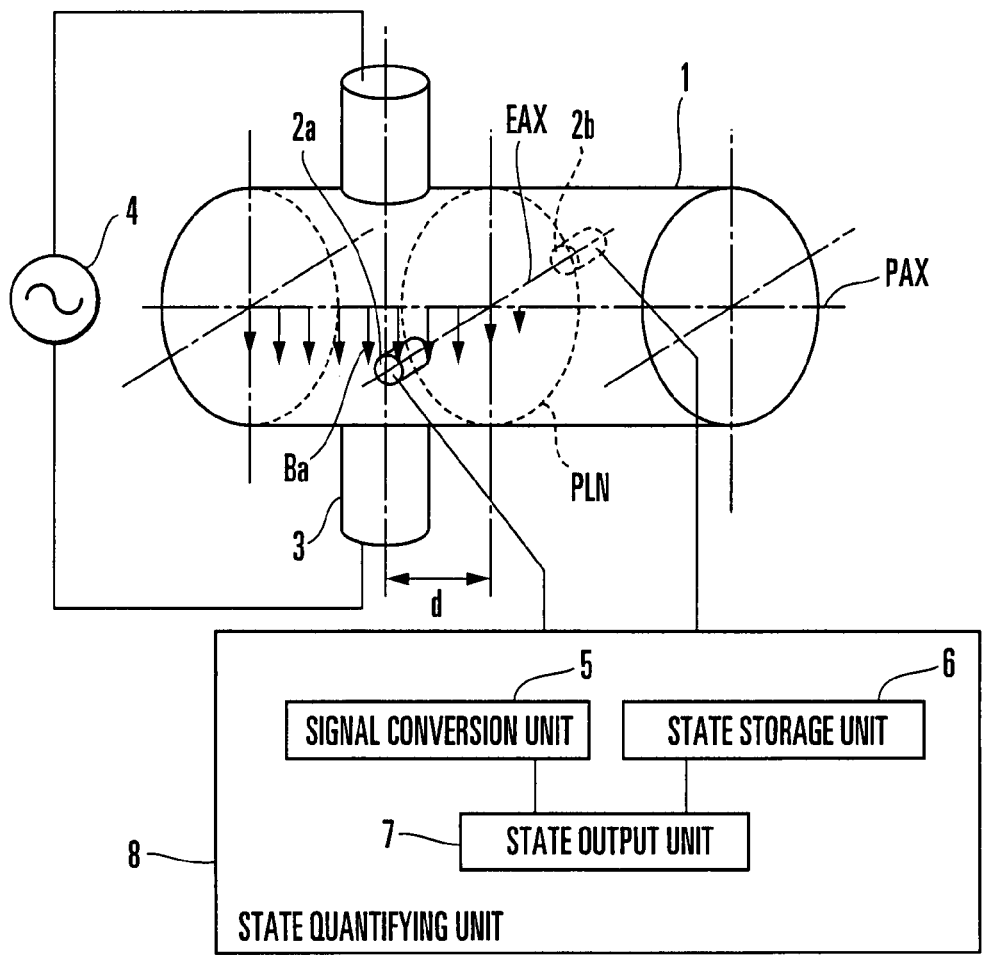
FIG. 26 is a block diagram showing the arrangement of a state detection device according to the first embodiment of the present invention.

The specific arrangement and operation of the state detection device according to this embodiment will be described next. FIG. 26 is a block diagram showing the arrangement of the state detection device according to this embodiment. The same reference numerals as in FIG. 26 denote the same components in FIG. 1. The state detection device of this embodiment includes a measuring tube 1, electrodes 2a and 2b, the exciting coil 3 placed at a position spaced apart by an offset distance d in the axial direction from a plane PLN which includes the electrodes 2a and 2b and is perpendicular to the direction of a measuring tube axis PAX, a power supply unit 4 which supplies an exciting current to the exciting coil 3, and a state quantifying unit 8.

The exciting coil 3 and the power supply unit 4 constitute an exciting unit which applies a time-changing magnetic field asymmetric to the plane PLN to the fluid to be measured.

The state quantifying unit 8 includes a signal conversion unit 5 which obtains the amplitudes and phases of two frequency components with the first and second angular frequencies $\omega0$ and $\omega2$ of the resultant electromotive forces detected by the electrodes 2a and 2b, extracts an electromotive force difference between the two angular frequency components as a $\partial A/\partial t$ components on the basis of the amplitudes and the phases, and extracts, from the $\partial A/\partial t$ components, the magnitude or phase of the variation factor dependent on the first parameter and independent of the frequency, a state storage unit 6 (equivalent to the above-described first table) which stores in advance the relationship between the first parameter and the magnitude or phase of the variation factor dependent on the first parameter, and a state output unit 7 which obtains the first parameter corresponding to the magnitude or phase of the extracted variation factor based on the relationship stored in the state storage unit 6.

The power supply unit 4 repeats, in a T-sec cycle, the operation of continuing the first excitation state for T1 sec in which an exciting current with a first angular frequency $\omega 0$ is supplied to the exciting coil 3 and then continuing the second excitation state for T2 sec in which an exciting current with a second angular frequency $\omega 2$ is supplied to the exciting coil 3. That is, T=T1+T2.

Figure 27:
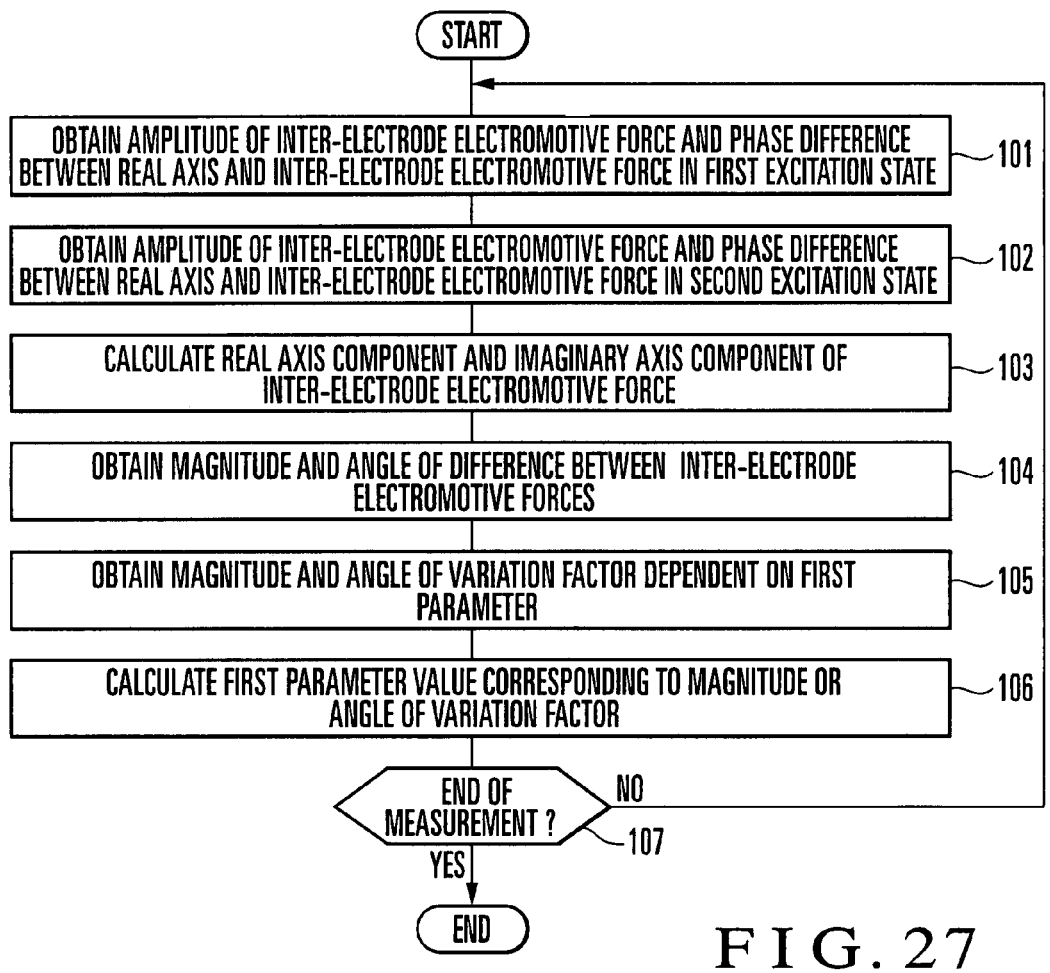
FIG. 27 is a flowchart showing the operation of a state quantifying unit according to the first embodiment of the present invention.

FIG. 27 is a flowchart showing the operations of the state quantifying unit 8. First of all, the signal conversion unit 5 obtains an amplitude r110 of the electromotive force E110 of a component with the angular frequency $\omega 0$ of the electromotive force between the electrodes 2a and 2b, and also obtains a phase difference $\phi 110$ between the real axis and the electromotive force E110 by using a phase detector (not shown) (step 101 in FIG. 27).

Subsequently, in the second excitation state, the signal conversion unit 5 obtains an amplitude r112 of the electromotive force E112 of a component with the angular frequency $\omega 2$ of the electromotive force between the electrodes 2a and 2b, and also obtains a phase difference $\phi 112$ between the real axis and the electromotive force E112 by using the phase detector (step 102).

The signal conversion unit 5 then calculates a real axis component E110x and imaginary axis component E110y of the inter-electrode electromotive force E110, and a real axis component E112x and imaginary axis component E112y of the inter-electrode electromotive force E112 according to the following equations (step 103):

$$E110x = r110 \cdot \cos(\phi 110) \quad (105)$$

$$E110y = r110 \cdot \sin(\phi 110) \quad (106)$$

$$E112x = r112 \cdot \cos(\phi 112) \quad (107)$$

$$E112y = r112 \cdot \sin(\phi 112) \quad (108)$$

After the calculation of equations (105) to (108), the signal conversion unit 5 obtains the magnitude and angle of the electromotive force difference EdA1 between the inter-electrode electromotive forces E110 and E112 (step 104). The processing in step 104 corresponds to the processing of obtaining a $\partial A/\partial t$ component, and is equivalent to the calculation of equation (101). The signal conversion unit 5 calculates a magnitude |EdA1| of the electromotive force difference EdA1 according to the following equation:

$$|EdA1| = \{(E110x - E112x)^2 + (E110y - E112y)^2\}^{1/2} \quad (109)$$

The signal conversion unit 5 then calculates an angle $\angle EdA1$ of the electromotive force difference EdA1 with respect to the real axis according to the following equation:

$$\angle EdA1 = \tan^{-1}\{(E110y - E112y)/(E110x - E112x)\} \quad (110)$$

With the above operation, the processing in step 104 is complete.

The signal conversion unit 5 then calculates the magnitude rk[p1] of the variation factor Cp1 dependent on the first parameter p1 and the angle $\theta 00[p1]$ with respect to the real axis from the electromotive force difference EdA1 according to the following equations (step 105):

$$rk[p1] = |EdA1|/\{b1 \cdot (\omega 0 - \omega 2)\} \quad (111)$$

$$\theta 00[p1] = \angle EdA1 - (\pi/2 + \theta 1) \quad (112)$$

The amplitude b1 of the magnetic field B1 generated from the exciting coil 3 and the phase difference $\theta 1$ between the magnetic field B1 and $\omega 0 \cdot t$ are constants which can be obtained in advance by calibration or the like.

The relationship between the first parameter p1 and the magnitude rk[p1] of the variation factor Cp1 or the relationship between the first parameter p1 and the angle $\theta 00[p1]$ of the variation factor Cp1 is registered in advance in the state storage unit 6 in the form of a mathematical expression or table. In step 106, the state output unit 7 calculates the value of the first parameter p1 corresponding to rk[p1] or $\theta 00[p1]$ by referring to the state storage unit 6 on the basis of the magnitude rk[p1] or angle $\theta 00[p1]$ of the variation factor Cp1 calculated by the signal conversion unit 5 (or acquires it from the state storage unit 6).

The state quantifying unit 8 performs the processing in steps 101 to 106 described above in a cycle T until, for example, the operator designates the end of the measurement (YES in step 107). Note that the processing in steps 102 to 106 is performed in the second excitation state for a duration of T2 sec.

As described above, this embodiment is configured to extract the electromotive force difference EdA1 ($\partial A/\partial t$ component) from the inter-electrode electromotive forces E110 and E112 in the two excitation states with different exciting frequencies, extract the magnitude or phase of the variation factor Cp1 dependent on the characteristic or state of the fluid or a state in the measuring tube (the first parameter p1) from the electromotive force difference EdA1, and obtain the first parameter p1 on the basis of the magnitude or phase of the variation factor Cp1. This makes it possible to accurately detect the characteristic or state of the fluid or the state in the measuring tube regardless of the flow velocity of the fluid.

In this embodiment, the components of the state quantifying unit 8, except for the detecting units of the inter-electrode electromotive forces E110 and E112, can be implemented by a computer comprising a CPU, storage unit, and interface and programs which control the hardware resources. In this embodiment, for example, the v×B component can be extracted by E110−EdA1·$\{(\omega 0 - \omega 2)/\omega 0\}$. There is known a technique of calculating the flow rate of the fluid from the v×B component in the field of a general electromagnetic flowmeter, which can be easily implemented by a computer included in the state quantifying unit 8. Therefore, according to this embodiment, the characteristic or state of the fluid or the state in the measuring tube can be detected by using basically the same hardware arrangement as that of an electromagnetic induction type flowmeter.

In this embodiment, it suffices to extract either the magnitude rk[p1] or angle $\theta 00[p1]$ of the variation factor Cp1 from the electromotive force difference EdA1. However, the first parameter p1 can be obtained by extracting both the magnitude and angle of the component. In this case, it suffices to select either the magnitude rk[p1] or the angle $\theta 00[p1]$ which has a higher sensitivity and obtain the first parameter p1 on the basis of the selected magnitude or angle. This makes it possible to improve the detection sensitivity.

In addition, this embodiment has exemplified the case wherein the exciting frequency is switched to $\omega 0$ or $\omega 2$. However, performing excitation using exciting currents containing components with the angular frequencies $\omega 0$ and $\omega 2$ makes it unnecessary to switch the exciting frequencies. This can calculate the first parameter p1 at higher speed. For example, it suffices to use the magnetic field represented by the following equation instead of equation (3).

$$B1 = b1 \cdot \cos(\omega 0 \cdot t - \theta 1) + b1 \cdot \cos(\omega 2 \cdot t - \theta 1) \quad (113)$$

Figure 28:
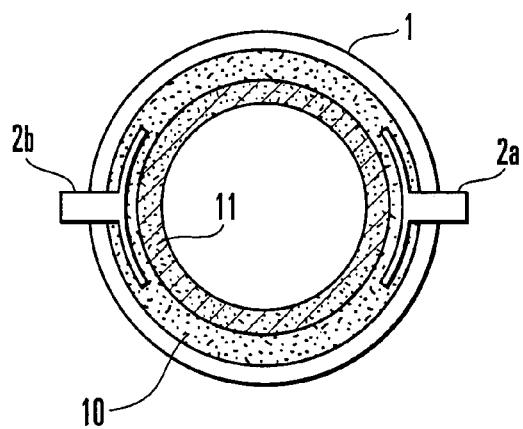
FIG. 28 is a sectional view showing an example of an electrode used in the state detection device according to the first embodiment of the present invention.

The following description will explain a specific example of the state detection device of this embodiment which detects the deposited state (a change in the inner diameter of the measuring tube) of a substance in the measuring tube. As shown in FIG. 28, this example uses capacitive coupling type electrodes which do not come into contact with a fluid to be measured in consideration of the deposition of a substance in the measuring tube 1. When the electrodes 2a and 2b are of the capacitive coupling type, they are coated with a lining 10 made of ceramic, Teflon, or the like formed on the inner wall of the measuring tube 1.

Figure 29:
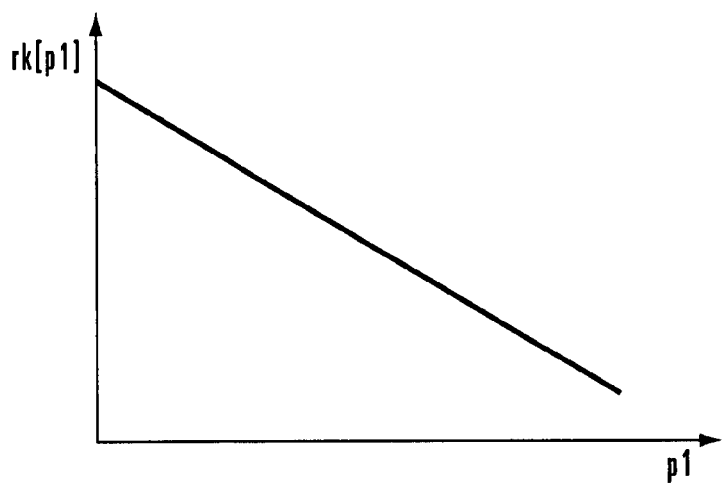
FIG. 29 is a graph showing an example of the relationship between the thickness of a substance adhering to the inside of a measuring tube and the magnitude of a variation factor according to the first embodiment of the present invention.

As shown in FIG. 28, as a substance 11 is deposited on the inner wall of the measuring tube 1, the inner diameter of the measuring tube 1 changes, and the value of the magnitude rk[p1] of the variation factor Cp1 varies. FIG. 29 shows an example of the relationship between the thickness (first parameter p1) of the substance 11 and the magnitude rk[p1] of the variation factor Cp1. Obtaining this relationship by a theoretical formula at the time of design or by measurement at the time of calibration and storing it in the state storage unit 6 in advance can obtain the thickness of the substance 11 in step 106 on the basis of the magnitude rk[p1] of the variation factor Cp1 obtained in step 105 in FIG. 27.

SECOND EMBODIMENT

The second embodiment of the present invention will be described next. This embodiment is the same as the first embodiment except that one exciting coil is added to the state detection device, and uses the above-described second principle. That is, the state detection device of this embodiment includes two exciting coils and a pair of electrodes, and has the same arrangement as that of the state detection device shown in FIG. 5 except for the signal processing system. The principle of this embodiment will therefore be described by using reference numerals in FIG. 5. If the second exciting coil to be newly added is placed on the same side as the first exciting coil, the resultant arrangement is a redundant arrangement of the first embodiment. Therefore, the second exciting coil needs to be placed on a side different from that of the first exciting coil through a plane including the electrodes. This embodiment uses the first extraction method as a method of extracting a $\partial A/\partial t$ component from a resultant vector, and obtains the first parameter irrelevant to the exciting frequency.

Assume that the first exciting current having an angular frequency $\omega 0$ is supplied to a first exciting coil 3a, the second exciting current having the angular frequency $\omega 0$ with a phase difference $\Delta\theta 2+\pi$ with respect to the first exciting current is supplied to a second exciting coil 3b, and the first parameter is p2. In this case, an inter-electrode electromotive force E220 is represented by the following equation according to equations (30), (68), and (75).

$$E220R = rk[p2] \cdot \exp\{j \cdot (\theta 1 + \theta 00[p2])\} \cdot \qquad (114)$$
$$[\exp(j \cdot \pi/2) \cdot [b1 + b2 \cdot \exp(j \cdot \Delta\theta 2)] \cdot \omega 0 +$$
$$\gamma \cdot \exp(j \cdot \Delta\theta 01) \cdot \{b1 - b2 \cdot \exp(j \cdot \Delta\theta 2)\} \cdot V]$$

Assume that the first exciting current having an angular frequency $\omega 2$ is supplied to the first exciting coil 3a, the second exciting current having the angular frequency $\omega 2$ with the phase difference $\Delta\theta 2+\pi$ with respect to the first exciting current is supplied to the second exciting coil 3b, and the first parameter is p2. In this case, an inter-electrode electromotive force E222R is represented by the following equation according to equations (30), (70), and (75).

$$E222R = rk[p2] \cdot \exp\{j \cdot (\theta 1 + \theta 00[p2])\} \cdot \qquad (115)$$
$$[\exp(j \cdot \pi/2) \cdot \{b1 + b2 \cdot \exp(j \cdot \Delta\theta 2)\} \cdot \omega 2 +$$
$$\gamma \cdot \exp(j \cdot \Delta\theta 01) \cdot \{b1 - b2 \cdot \exp(j \cdot \Delta\theta 2)\} \cdot V]$$

In this case, if a distance d1 from a plane PLN, which is perpendicular to a measuring tube axis PAX and includes electrodes 2a and 2b, to the first exciting coil 3a is almost equal to a distance d2 from the plane PLN to a second exciting coil 3b (d1≈d2), then b1≈b2 and $\Delta\theta 2\approx 0$. In this case, equations (114) and (115) are rewritten as follows:

$$E220R = rk[p2] \cdot \exp\{j \cdot (\theta 1 + \theta 00[p2])\} \cdot \exp(j \cdot \pi/2) \cdot \{2 \cdot b1 \cdot \omega 0\} \qquad (116)$$

$$E222R = rk[p2] \cdot \exp\{j \cdot (\theta 1 + \theta 00[p2])\} \cdot \exp(j \cdot \pi/2) \cdot \{2 \cdot b1 \cdot \omega 2\} \qquad (117)$$

That is, since the inter-electrode electromotive forces E220R and E222R are almost only the electromotive forces based on the $\partial A/\partial t$ components, computation errors in the extraction of a $\partial A/\partial t$ component can be reduced. This point is a difference in terms of technical significance between the first and second embodiments. Note, however, that the subsequent theoretical development will be made assuming that b1≠b2 and $\Delta\theta 2\neq 0$.

Letting EdA2 be the difference between the inter-electrode electromotive forces E220R and E222R, the electromotive force difference EdA2 is given by $$EdA2 = (E220R - E222R) \qquad (118)$$
$$= rk[p2] \cdot \exp(j \cdot \theta 00[p2]) \cdot \exp\{j \cdot (\pi/2 + \theta 1)\} \cdot$$
$$\{b1 + b2 \cdot \exp(j \cdot \Delta\theta 2)\} \cdot (\omega 0 - \omega 2)$$

According to equation (118), it is obvious that a $\partial A/\partial t$ component in a resultant vector can be extracted by using the output difference between different frequency components. Equation (118) is irrelevant to a magnitude V of the flow velocity, and hence is only the component generated by $\partial A/\partial t$. Using the electromotive force difference EdA2, therefore, makes it possible to measure a state of the fluid or a state in the measuring tube other than the flow velocity.

When a variation factor dependent on the first parameter is Cp2, Cp2=rk[p2]·exp(j·$\theta 00$[p2]) holds, and the remaining portion is a constant which is provided at the time of calibration. The variation factor Cp2 is represented by the following equation according to equation (118).

$$Cp2 = EdA2 / [\exp\{j \cdot (\pi/2 + \theta 1)\} \cdot \{b1 + b2 \cdot \exp(j \cdot \Delta\theta 2)\} \cdot (\omega 0 - \omega 2)] \qquad (119)$$

Letting m2b and $\theta 2b$ be the magnitude and angle of [exp{j·($\pi/2+\theta 1$)}·{b1+b2·exp(j·$\Delta\theta 2$)}] in equation (119), m2b and $\theta 2b$ are represented by $$m2b = \{b1^2 + b2^2 + b1 \cdot b2 \cdot \cos(\Delta\theta 2)\}^{1/2} \qquad (120)$$

$$\theta 2b = \tan^{-1}[\{b2 \cdot \sin(\Delta\theta 2)\}/\{b1 + b2 \cdot \cos(\Delta\theta 2)\}] - (\pi/2 + \theta 1) \qquad (121)$$

According to equations (119) to (121), the magnitude rk[p2] of the variation factor Cp2 and the angle $\theta 00$[h2] with respect to the real axis are represented by $$rk[p2]=|EdA1|/\{m2b \cdot (\omega 0 - \omega 2)\} \quad (122)$$

$$\theta 00[p2]=\angle EdA1-\theta 2b \quad (123)$$

The first parameter p2 can be obtained from the relationship between the first parameter p2 and rk[p2], which is checked in advance by measurement or the like at the time of calibration, or the relationship between the first parameter p2 and the angle $\theta 00[p2]$.

Figure 30:
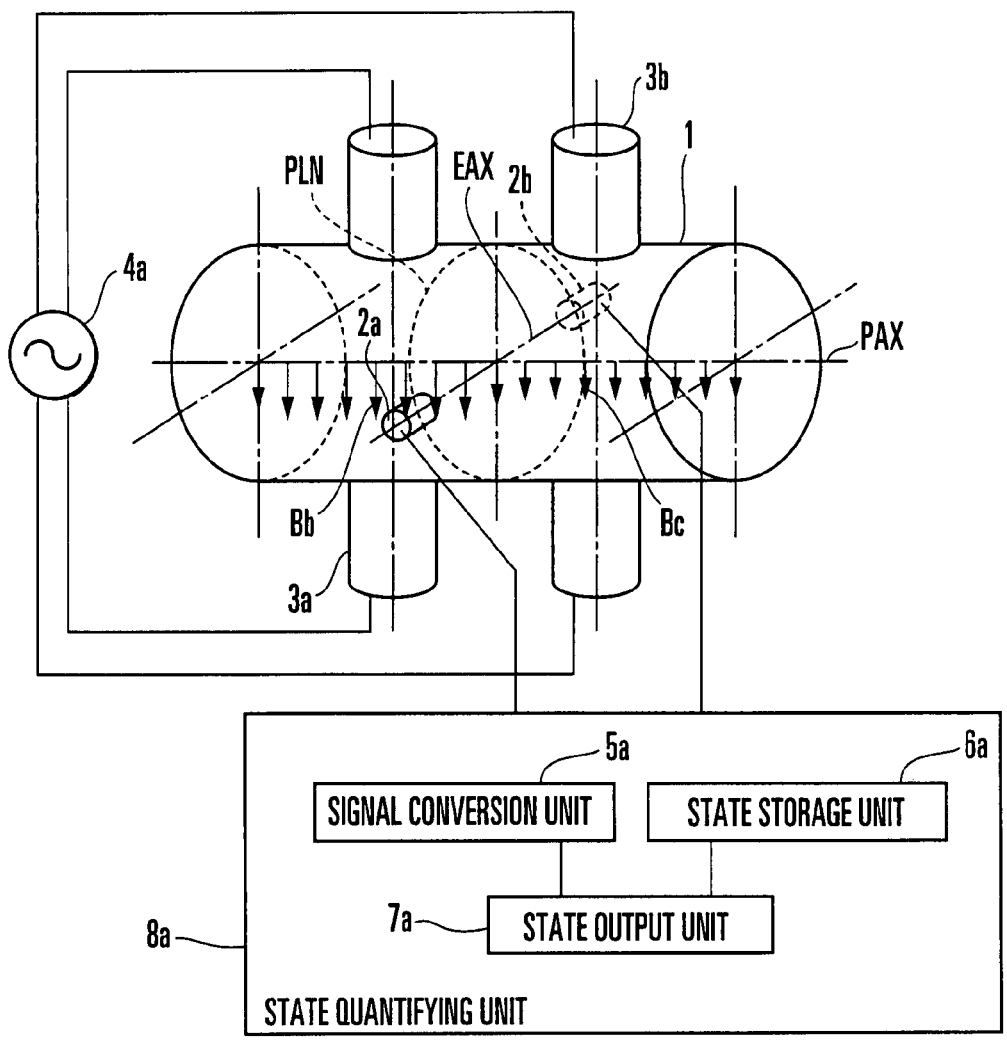
FIG. 30 is a block diagram showing the arrangement of a state detection device according to the second embodiment of the present invention.

The specific arrangement and operation of the state detection device according to this embodiment will be described next. FIG. 30 is a block diagram showing the arrangement of the state detection device according to this embodiment. The same reference numerals as in FIG. 5 denote the same components in FIG. 1. The state detection device of this embodiment includes a measuring tube 1, electrodes 2a and 2b, the first and second exciting coils 3a and 3b, a power supply unit 4 which supplies exciting currents to the first and second exciting coils 3a and 3b, and a state quantifying unit 8a.

The first and second exciting coils 3a and 3b and the power supply unit 4a constitute an exciting unit which applies a time-changing magnetic field asymmetric to a plane PLN to the fluid to be measured.

The state quantifying unit 8a includes a signal conversion unit 5a which obtains the amplitudes and phases of two frequency components with the first and second angular frequencies $\omega 0$ and $\omega 2$ of the resultant electromotive forces detected by the electrodes 2a and 2b, extracts an electromotive force difference between the two angular frequency components as a $\partial A/\partial t$ components on the basis of the amplitudes and the phases, and extracts, from the $\partial A/\partial t$ components, the magnitude or phase of the variation factor dependent on the first parameter and independent of the frequency, a state storage unit 6a (equivalent to the above-described first table) which stores in advance the relationship between the first parameter and the magnitude or phase of the variation factor dependent on the first parameter, and a state output unit 7a which obtains the first parameter corresponding to the magnitude or phase of the extracted variation factor based on the relationship stored in the state storage unit 6a.

In this embodiment, as described above, the distance d1 from the plane PLN to the first exciting coil 3a is almost equal to the distance d2 from the plane PLN to the second exciting coil 3b.

The power supply unit 4a repeats, in a T-sec cycle, the operation of continuing the first excitation state for T1 sec in which the first exciting current with the first angular frequency $\omega 0$ is supplied to the first exciting coil 3a and at the same time the second exciting current with a phase difference $\Delta\theta 2+\pi$ with respect to the first exciting current and the angular frequency $\omega 0$ is supplied to the second exciting coil 3b, and continuing the second excitation state for T2 sec in which the frequencies of the first and second exciting currents have been changed with respect to the first excitation state to the second angular frequency $\omega 2$. That is, T=T1+T2.

Although the operation of the exciting unit is different from that in the first embodiment, the processing of the state quantifying unit 8a is the same as that in the first embodiment, and hence the operation of the state quantifying unit 8a will be described by using the reference numerals in FIG. 27. First of all, the signal conversion unit 5a obtains an amplitude r220R of the electromotive force E220R of a component with the angular frequency $\omega 0$ of the electromotive force between the electrodes 2a and 2b in the first excitation state, and obtains a phase difference $\phi 220R$ between the real axis and the inter-electrode electromotive force E220R by using a phase detector (not shown) (step 101 in FIG. 27).

The signal conversion unit 5a then obtains an amplitude r222R of the electromotive force E222R of a component with the angular frequency $\omega 2$ of the electromotive force between the electrodes 2a and 2b in the second excitation state, and obtains a phase difference $\phi 222R$ between the real axis and the inter-electrode electromotive force E222R by using the phase detector (step 102).

The signal conversion unit 5a then calculates a real axis component E220Rx and imaginary axis component E220Ry of the inter-electrode electromotive force E220R, and a real axis component E222Rx and imaginary axis component E222Ry of the inter-electrode electromotive force E222R according to the following equations (step 103):

$$E220Rx=r220R \cdot \cos(\phi 220R) \quad (124)$$

$$E220Ry=r220R \cdot \sin(\phi 220R) \quad (125)$$

$$E222Rx=r222R \cdot \cos(\phi 222R) \quad (126)$$

$$E222Ry=r222R \cdot \sin(\phi 222R) \quad (127)$$

After the calculation of equations (124) to (127), the signal conversion unit 5a obtains the magnitude and angle of the electromotive force difference EdA2 between the inter-electrode electromotive forces E220R and E222R (step 104). The processing in step 104 corresponds to the processing of obtaining a $\partial A/\partial t$ component, and is equivalent to the calculation of equation (118). The signal conversion unit 5a calculates a magnitude |EdA2| of the electromotive force difference EdA2 according to the following equation:

$$|EdA2| = \{(E220Rx - E222Rx)^2 + (E220Ry - E222Ry)^2\}^{1/2} \quad (128)$$

The signal conversion unit 5a then calculates an angle $\angle EdA2$ of the electromotive force difference EdA2 with respect to the real axis according to the following equation:

$$\angle EdA2 = \tan^{-1}\{(E220Ry - E222Ry)/(E220Rx - E222Rx)\} \quad (129)$$

With the above operation, the processing in step 104 is complete.

The signal conversion unit 5a then calculates the magnitude rk[p2] of the variation factor Cp2 dependent on the first parameter p2 and the angle $\theta 00[p2]$ with respect to the real axis from the electromotive force difference EdA2 according to the following equations (step 105):

$$rk[p2]=|EdA2|/(m2b \cdot \omega 0 - \omega 2) \quad (130)$$

$$\theta 00[p2]=\angle EdA2-\theta 2b \quad (131)$$

Note that m2b and $\theta 2b$ (the amplitude b1 of the magnetic field B1 generated from the first exciting coil 3a, the amplitude b2 of the magnetic field B2 generated from the second exciting coil 3b, the phase difference $\theta 1$ between the magnetic field B1 and $\omega 0 \cdot t$, and $\theta \Delta 2$) are constants which can be obtained in advance by calibration or the like.

The relationship between the first parameter p2 and the magnitude rk[p2] of the variation factor Cp2 or the relationship between the first parameter p2 and the angle $\theta 00[p2]$ of the variation factor Cp2 is registered in advance in the state storage unit 6a in the form of a mathematical expression or table. In step 106, the state output unit 7a calculates the value of the first parameter p2 corresponding to rk[p2] or $\theta 00[p2]$ by referring to the state storage unit 6a on the basis of the magnitude rk[p2] or angle θ00[p2] of the variation factor Cp2 calculated by the signal conversion unit 5a (or acquires it from the state storage unit 6a). The state quantifying unit 8a performs the processing in steps 101 to 106 described above in a cycle T until, for example, the operator designates the end of the measurement (YES in step 107).

As described above, this embodiment is configured to obtain the inter-electrode electromotive force E220R in the first excitation state in which the magnetic field B1 with angular frequency ω0 is applied from the first exciting coil 3a to the fluid to be measured, and the magnetic field B2 having the frequency ω0 with the phase difference Δθ2+π with respect to the magnetic field B1 is applied from the second exciting coil 3b to the fluid to be measured, obtain the inter-electrode electromotive force E222R in the second excitation state in which the exciting frequency with respect to the first excitation state changes to ω2, extract the electromotive force difference EdA2 (∂A/∂t component) from the inter-electrode electromotive forces E220 and E222, extract the magnitude or phase of the variation factor Cp2 dependent on the characteristic or state of the fluid or a state in the measuring tube (the first parameter p2) from the electromotive force difference EdA2, and obtain the first parameter p2 on the basis of the magnitude or phase of the variation factor Cp2. This makes it possible to accurately detect the characteristic or state of the fluid or the state in the measuring tube regardless of the flow velocity of the fluid.

In this embodiment, the components of the state quantifying unit 8a, except for the detecting units of the inter-electrode electromotive forces E220R and E222R, can be implemented by a computer comprising a CPU, storage unit, and interface and programs which control the hardware resources. In this embodiment, for example, the v×B component can be extracted by E220R−EdA2·{(ω0−ω2)/ω0}. There is known a technique of calculating the flow rate of the fluid from the v×B component in the field of a general electromagnetic flowmeter, which can be easily implemented by a computer included in the state quantifying unit 8a. Therefore, according to this embodiment, the characteristic or state of the fluid or the state in the measuring tube can be detected by using basically the same hardware arrangement as that of an electromagnetic induction type flowmeter.

In this embodiment, adjusting the distance d1 from the plane PLN including the electrodes 2a and 2b to the first exciting coil 3a and the distance d2 from the plane PLN to the second exciting coil 3b allows the inter-electrode electromotive forces E220R and E220R to be almost only electromotive forces based on ∂A/∂t components. With this processing, this embodiment can extract a ∂A/∂t component more effectively, and can reduce computation errors more than the first embodiment.

In this embodiment, it suffices to extract either the magnitude rk[p2] or angle θ00[p2] of the variation factor Cp2 from the electromotive force difference EdA2. However, the first parameter p2 can be obtained by extracting both the magnitude and angle of the component. In this case, it suffices to select either the magnitude rk[p2] or the angle θ00[p2] which has a higher sensitivity and obtain the first parameter p2 on the basis of the selected magnitude or angle. This makes it possible to improve the detection sensitivity.

In addition, this embodiment has exemplified the case wherein the exciting angular frequency is switched to ω0 or ω2. However, performing excitation using exciting currents containing components with the angular frequencies ω0 and ω2 makes it unnecessary to switch the exciting frequencies. This can calculate the first parameter p2 at higher speed. For example, it suffices to use the magnetic field represented by the following equation instead of equations (22) and (23).

$$B1 = b1 \cdot \cos(\omega 0 \cdot t - \theta 1) + b1 \cdot \cos(\omega 2 \cdot t - \theta 1) \tag{132}$$

$$B2 = b2 \cdot \cos(\omega 0 \cdot t - \theta 2) + b2 \cdot \cos(\omega 2 \cdot t - \theta 2) \tag{133}$$

Figure 31:
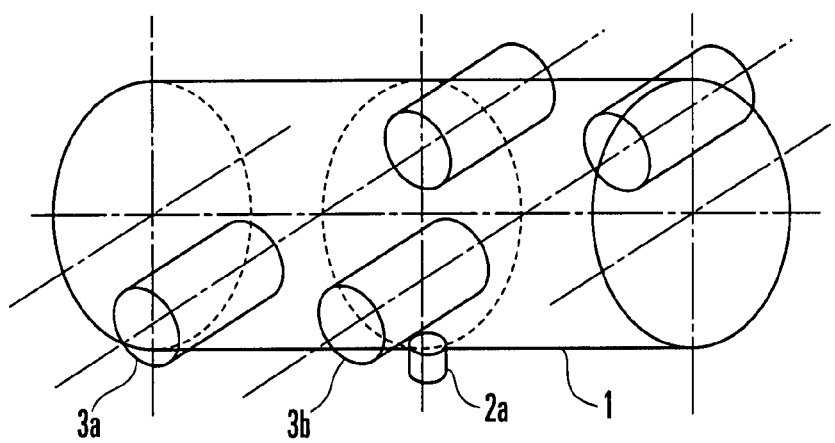
FIG. 31 is a perspective view showing the arrangement of an exciting coil and an electrode used in the state detection device according to the second embodiment of the present invention.
Figure 32:
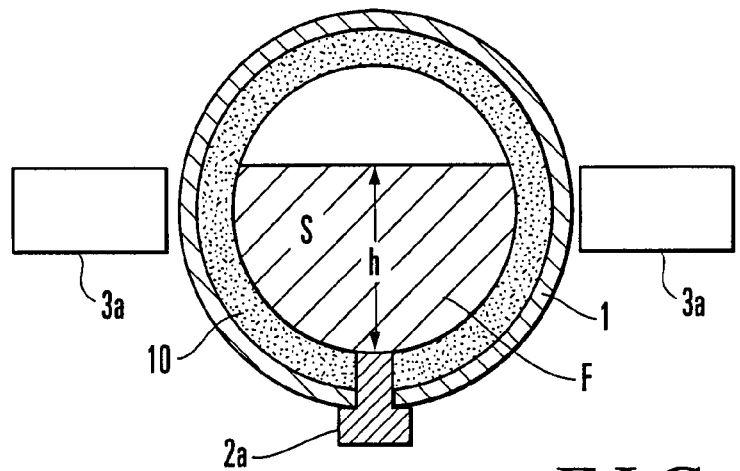
FIG. 32 is a sectional view showing the arrangement of the exciting coil and the electrode used in the state detection device according to the second embodiment of the present invention.

The following description will explain a specific example of the state detection device of this embodiment which detects a level or sectional area of the fluid. In this case, considering that a level h varies, as shown in FIGS. 31 and 32, the first and second exciting coils 3a and 3b are arranged in a direction horizontal to the measuring tube 1, and the electrode 2a is placed under the measuring tube 1. When only one electrode is to be used in this manner, it suffices if an earth ring (not shown) for grounding the potential of the fluid F is provided on the measuring tube 1, and an electromotive force (a potential difference from the ground potential) generated at the electrode 2a is detected by the signal conversion unit 5a.

Figure 33:
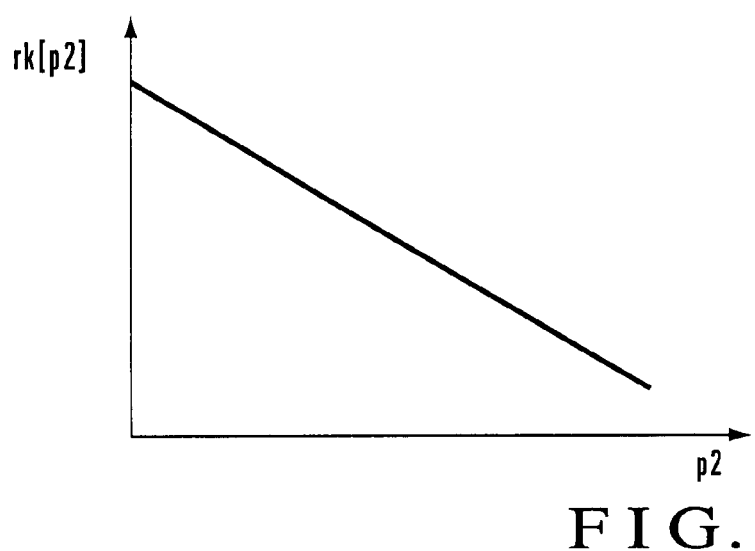
FIG. 33 is a graph showing an example of the relationship between the level or sectional area of a fluid and the magnitude of a variation factor according to the second embodiment of the present invention.

As the level h (sectional area S) of the fluid F varies, the value of the magnitude rk[p2] of the variation factor Cp2 also varies. FIG. 33 shows an example of the relationship between the level h or sectional area S (first parameter p2) of the fluid F and the magnitude rk[p2] of the variation factor Cp2. The relationship shown in FIG. 33 changes depending on the shape or the like of the measuring tube 1. Therefore, obtaining this relationship by a theoretical formula at the time of design or measurement at the time of calibration and storing it in the state storage unit 6a in advance make it possible to obtain the level h or sectional area S of the fluid F in step 106 on the basis of the magnitude rk[p2] of the variation factor Cp2 obtained in step 105 and to obtain the level h or sectional area S of the fluid F in step 106.

THIRD EMBODIMENT

The third embodiment of the present invention will be described next. A state detection device according to this embodiment includes two exciting coils and a pair of electrodes, and has the same arrangement as that of the state detection device shown in FIG. 5 except for the signal processing system. The principle of this embodiment will therefore be described by using reference numerals in FIG. 5. This embodiment uses the second extraction method as a method of extracting a ∂A/∂t component from a resultant vector to obtain the first parameter irrelevant to an exciting frequency.

Assume that the first exciting current having an angular frequency ω0 is supplied to a first exciting coil 3a, the second exciting current having the angular frequency ω0 with a phase difference Δθ2+π with respect to the first exciting current is supplied to a second exciting coil 3b, and the first parameter is p3. In this case, an inter-electrode electromotive force E320R is represented by the following equation according to equations (30), (68), and (75).

$$E320R = rk[p3] \cdot \exp\{j \cdot (\theta 1 + \theta 00[p3])\} \cdot \tag{134}$$
$$[\exp(j \cdot \pi/2) \cdot \{b1 + b2 \cdot \exp(j \cdot \Delta\theta 2)\} \cdot \omega 0 +$$
$$\gamma \cdot \exp(j \cdot \Delta\theta 01) \cdot \{b1 - b2 \cdot \exp(j \cdot \Delta\theta 2)\} \cdot V]$$

From equations (71) and (72), the following approximate expression holds in equation (134):

$$|b1 + b2 \cdot \exp(j \cdot \Delta\theta 2)| \gg |b1 - b2 \cdot \exp(j \cdot \Delta\theta 2)| \tag{135}$$

$$|\omega 0 \cdot \exp(j \cdot \pi/2) \cdot \{b1 + b2 \cdot \exp(j \cdot \Delta\theta 2)\}| \gg |\gamma \cdot V \cdot \exp(j \cdot \Delta\theta 01) \cdot \{b1 - b2 \cdot \exp(j \cdot \Delta\theta 2)\}| \tag{136}$$

The following expressions represent an electromotive force EdA3 which approximates the inter-electrode electromotive force E320R in equation (134) by using the condition of expression (136).

$$EdA3 \approx E320R \tag{137}$$

$$EdA3 = rk[p3] \cdot \exp\{j \cdot \theta 00[p3]\} \cdot \exp\{j \cdot (\pi/2 + \theta 1)\} \cdot \tag{138}$$
$$\{b1 + b2 \cdot \exp(j \cdot \Delta\theta 2)\} \cdot \omega 0$$

In equation (138), the ∂A/∂t component in the resultant vector can be extracted by using the phase difference between the magnetic fields generated from the first and second exciting coils 3a and 3b. Equation (138) is irrelevant to the magnitude V of the flow velocity, and hence is only the component generated by ∂A/∂t. The fluid state except for the flow velocity, and the state in the measuring tube can be measured by using the inter-electrode electromotive force EdA3.

When a variation factor dependent on the first parameter is Cp3, Cp3=rk[p3] exp(j·θ00[p3]) holds, and the remaining portion is a constant which is provided at the time of calibration. The variation factor Cp3 is represented by equation (138).

$$Cp3 = EdA3 / [\exp\{j \cdot (\pi/2 + \theta 1)\} \cdot \{b1 + b2 \cdot \exp(j \cdot \Delta\theta 2)\} \cdot \omega 0] \tag{139}$$

Letting m2b be the magnitude of $[\exp\{j\cdot(\pi/2+\theta 1)\}\cdot\{b1+b2\cdot\exp(j\cdot\Delta\theta 2)\}]$ in equation (139), and letting θ2b be the angle, m2b and θ2b are represented by equations (120) and (121).

Upon applying equations (120) and (121) to equation (139), a magnitude rk[p3] of the variation factor Cp3 and an angle θ00[p3] thereof from the real axis are represented by $$rk[p3]=|EdA3|/(m2b \cdot \omega 0) \tag{140}$$

$$\theta 00[p3]=\angle EdA3-\theta 2b \tag{141}$$

The first parameter p3 can be obtained from the relationship between the first parameter p3 and rk[p3], which is checked in advance by measurement or the like at the time of calibration, or the relationship between the first parameter p3 and the angle θ00[p3].

The specific arrangement and operation of the state detection device according to this embodiment will be described next. The state detection device of this embodiment has the same arrangement as that in the second embodiment, and will therefore be described by using reference numerals in FIG. 30. The state detection device of this embodiment includes a measuring tube 1, electrodes 2a and 2b, the first and second exciting coils 3a and 3b, a power supply unit 4, and a state quantifying unit 8a.

The state quantifying unit 8a includes a signal conversion unit 5a which obtains the amplitudes and phases of the resultant electromotive forces detected by the electrodes 2a and 2b, extracts a ∂A/∂t component, and extracts, from the ∂A/∂t component, the magnitude or phase of the variation factor dependent on the first parameter and independent of the frequency, a state storage unit 6a (equivalent to the above-described first table) which stores in advance the relationship between the first parameter and the magnitude or phase of the variation factor dependent on the first parameter, and a state output unit 7a which obtains the first parameter corresponding to the magnitude or phase of the extracted variation factor based on the relationship stored in the state storage unit 6a.

The power supply unit 4a supplies the first exciting current with the angular frequency ω0 to the first exciting coil 3a, and simultaneously supplies the second exciting current having the angular frequency ω0 with a phase difference Δθ2+π with respect to the first exciting current to the second exciting coil 3b. The phase difference between the magnetic field generated from the first exciting coil 3a and the magnetic field generated from the second exciting coil 3b is made almost π(Δθ02≈0).

Figure 34:
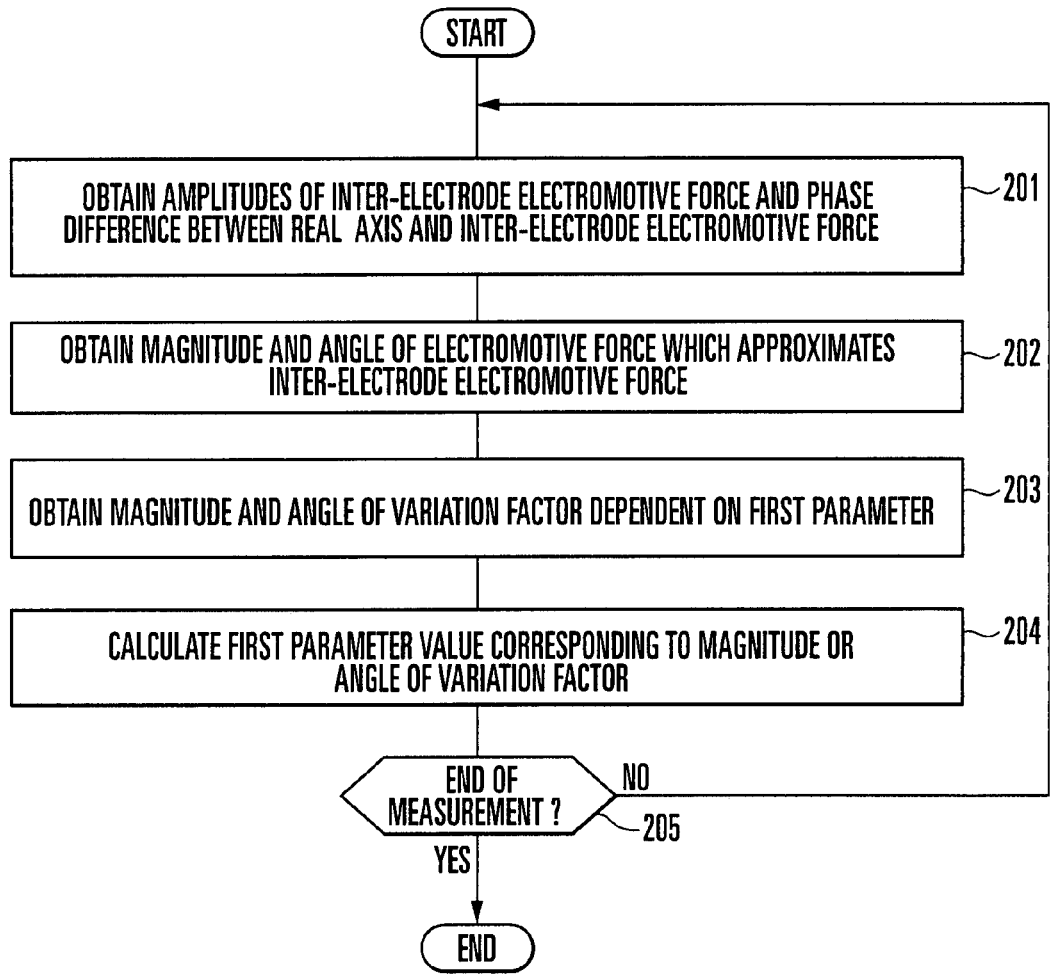
FIG. 34 is a flowchart showing the operation of a state quantifying unit according to the third embodiment of the present invention.

FIG. 34 is a flowchart showing the operations of the state quantifying unit 8a of this embodiment. First of all, the signal conversion unit 5a obtains an amplitude r320R of the electromotive force E320R of a component with the angular frequency ω0 of the electromotive force between the electrodes 2a and 2b, and obtains a phase difference φ320R between the real axis and the inter-electrode electromotive force E320R by using a phase detector (not shown) (step 201 in FIG. 34).

Next, the signal conversion unit 5a obtains the magnitude and angle of the electromotive force EdA3 which approximates the inter-electrode electromotive force E320R (step 202). The processing in step 202 corresponds to the processing of obtaining the ∂A/∂t component, and is equivalent to the calculation of equation (138). The signal conversion unit 5a calculates a magnitude |EdA3| of the electromotive force EdA3 which approximates the inter-electrode electromotive force E320R according to the following equation:

$$|EdA3|=r320R \tag{142}$$

The signal conversion unit 5a then calculates an angle ∠EdA3 of the inter-electrode electromotive force EdA3 with respect to the real axis according to the following equation:

$$\angle EdA3=\phi 320R \tag{143}$$

With the above operation, the processing in step 202 is complete.

The signal conversion unit 5a then calculates the magnitude rk[p3] of the variation factor Cp3 dependent on the first parameter p3 and the angle θ00[p3] with respect to the real axis from the electromotive force difference EdA3 according to the following equations (step 203):

$$rk[p3]=|EvA3|/(m2b \cdot \omega 0) \tag{144}$$

$$\theta 00[p3]=\angle EdA3-\theta 2b \tag{145}$$

Note that m2b and θ2b (the amplitude b1 of the magnetic field B1 generated from the first exciting coil 3a, the amplitude b2 of the magnetic field B2 generated from the second exciting coil 3b, the phase difference θ1 between the magnetic field B1 and ω0·t, and Δθ2) are constants which can be obtained in advance by calibration or the like.

The relationship between the first parameter p3 and the magnitude rk[p3] of the variation factor Cp3 or the relationship between the first parameter p3 and the angle θ00[p3] of the variation factor Cp3 is registered in advance in the state storage unit 6a in the form of a mathematical expression or table. In step 204, the state output unit 7a calculates the value of the first parameter p3 corresponding to rk[p3] or θ00[p3] by referring to the state storage unit 6a on the basis of the magnitude rk[p3] or angle θ00[p3] of the variation factor Cp3 calculated by the signal conversion unit 5a (or acquires it from the state storage unit 6a). The state quantifying unit 8a performs the processing in steps 201 to 204 described above in a predetermined cycle until, for example, the operator designates the end of the measurement (YES in step 205).

As described above, according to this embodiment, note that when the magnitudes of the magnetic fields B1 and B2 are equal to each other in a state wherein the phase difference between the magnetic fields B1 and B2 generated from the first and second exciting coils 3a and 3b is almost π, the inter-electrode electromotive force E320R can be approximately extracted as the ∂A/∂t component. This embodiment is configured to extract the magnitude or phase of the variation factor Cp3 dependent on the characteristic or state of the fluid or a state in the measuring tube (the first parameter p3) from the approximately extracted ∂A/∂t component, and obtain the first parameter p3 based on the magnitude or phase of the variation factor Cp3. Therefore, the characteristic or state of the fluid or the state in the measuring tube can be accurately detected regardless of the flow velocity of the fluid As in the second embodiment, the components of the state quantifying unit 8a of this embodiment, except for the detecting unit of the inter-electrode electromotive force E320R, can be implemented by a computer and program. In this embodiment, assume that the first exciting current having an angular frequency ω0 is supplied to the first exciting coil 3a, the second exciting current having the angular frequency ω0 with the phase difference Δθ2 with respect to the first exciting current is supplied to the second exciting coil 3b, and the first parameter is p3. In this case, an inter-electrode electromotive force E320 is obtained by reversing the sign of b2 in equation (134). As a result, the inter-electrode electromotive force E320 can be handled as the v×B component. Therefore, according to this embodiment, the characteristic or state of the fluid or the state in the measuring tube can be detected by using basically the same hardware arrangement as that of an electromagnetic induction type flowmeter.

In this embodiment, it suffices to extract either the magnitude rk[p3] or angle θ00[p3] of the variation factor Cp3 from the inter-electrode electromotive force EdA3. However, the first parameter p3 can be obtained by extracting both the magnitude and angle of the component. In this case, it suffices to select either the magnitude rk[p3] or the angle θ00[p3] which has a higher sensitivity and obtain the first parameter p3 on the basis of the selected magnitude or angle. This makes it possible to improve the detection sensitivity.

Fourth Embodiment

The fourth embodiment of the present invention will be described next. A state detection device according to this embodiment includes two exciting coils and a pair of electrodes, and has the same arrangement as that of the state detection device shown in FIG. 5 except for the signal processing system. The principle of this embodiment will therefore be described by using reference numerals in FIG. 5. This embodiment uses the second extraction method as a method of extracting a ∂A/∂t component from a resultant vector, and obtains the second parameter for a variation factor having a frequency characteristic. For example, the second parameter is a fluid impedance, and the conductivity and permittivity of the fluid.

Assume that the first exciting current having an angular frequency ω0 is supplied to a first exciting coil 3a, the second exciting current having the angular frequency ω0 with the phase difference Δθ2+π with respect to the first exciting current is supplied to a second exciting coil 3b, and the second parameter is p4. In this case, an inter-electrode electromotive force E420R is represented by the following equation according to equations (30), (78), and (79).

$$E420R = rk[p4, \omega 0] \cdot \exp\{j \cdot (\theta 1 + \theta 00[p4, \omega 0])\} \cdot \quad (146)$$
$$[\exp(j \cdot \pi/2) \cdot \{b1 + b2 \cdot \exp(j \cdot \Delta\theta 2)\} \cdot \omega 0 +$$
$$\gamma \cdot \exp(j \cdot \Delta\theta 01) \cdot \{b1 - b2 \cdot \exp(j \cdot \Delta\theta 2)\} \cdot V]$$

From equations (71) and (72), the following approximate expression holds in equation (146):

$$|b1+b2\cdot\exp(j\cdot\Delta\theta 2)| \gg |b1-b2\cdot\exp(j\cdot\Delta\theta 2)| \quad (147)$$

$$|\omega 0\cdot\exp(j\cdot\pi/2)\cdot\{b1+b2\cdot\exp(j\cdot\Delta\theta 2)\}| \gg |\gamma\cdot V\cdot\exp(j\cdot\Delta\theta 01)\cdot\{b1-b2\cdot\exp(j\cdot\Delta\theta 2)\}| \quad (148)$$

The following expressions represent an electromotive force EdA40 which approximates the inter-electrode electromotive force E420R in equation (146) by using the condition of expression (148).

$$EdA40 \approx E420R \quad (149)$$

$$EdA40 = rk[p4, \omega 0] \cdot \exp\{j \cdot \theta 00[p4, \omega 0]\} \cdot \exp\{j \cdot (\pi/2 + \theta 1)\} \cdot \{b1 + b2 \cdot \exp(j \cdot \Delta\theta 2)\} \cdot \omega 0 \quad (150)$$

Assume that the first exciting current having an angular frequency ω2 is supplied to the first exciting coil 3a, the second exciting current having the angular frequency ω2 with a phase difference Δθ2+π with respect to the first exciting current is supplied to the second exciting coil 3b, and the second parameter is p4. In this case, an inter-electrode electromotive force E422R is represented by the following equation according to equations (30), (81) and (82).

$$E422R = rk[p4, \omega 2] \cdot \exp\{j \cdot (\theta 1 + \theta 00[p4, \omega 2])\} \cdot \quad (151)$$
$$[\exp(j \cdot \pi/2) \cdot \{b1 + b2 \cdot \exp(j \cdot \Delta\theta 2)\} \cdot \omega 2 +$$
$$\gamma \cdot \exp(j \cdot \Delta\theta 01) \cdot \{b1 - b2 \cdot \exp(j \cdot \Delta\theta 2)\} \cdot V]$$

Since ω2>γ·V holds, the following condition holds for the inter-electrode electromotive force E422R given by equation (151) in consideration of the condition represented by equation (147).

$$|\omega 2\cdot\exp(j\cdot\pi/2)\cdot\{b1+b2\cdot\exp(j\cdot\Delta\theta 2)\}| \gg |\gamma\cdot V\cdot\exp(j\cdot\Delta\theta 01)\cdot\{b1-b2\cdot\exp(j\cdot\Delta\theta 2)\}| \quad (152)$$

The following expressions represent the inter-electrode electromotive force EdA42 which approximates the inter-electrode electromotive force E422R in equation (151) by using the condition of expression (152).

$$EdA42 \approx E422R \quad (153)$$

$$EdA42 = rk[p4, \omega 2] \cdot \exp\{j \cdot \theta 00[p4, \omega 2]\} \cdot \quad (154)$$
$$\exp(j \cdot (\pi/2 + \theta 1)) \cdot$$
$$\{b1 + b2 \cdot \exp(j \cdot \Delta\theta 2)\} \cdot \omega 2$$

In equations (150) and (154), the ∂A/∂t component in the resultant vector can be extracted by using the phase difference between the magnetic fields generated from the first and second exciting coils 3a and 3b. Equations (150) and (154) are irrelevant to the magnitude V of the flow velocity, and hence are only the component generated by ∂A/∂t. The fluid state except for the flow velocity, and the state in the measuring tube can be measured by using this electromotive force difference.

When a variation factor dependent on the second parameter is Cp40 in equation (150), Cp40=rk[p4,ω0]·exp(j·θ00[p4,ω0]) holds, and the remaining portion is a constant which is provided at the time of calibration. The variation factor Cp40 is represented by equation (150).

$$Cp40 = EdA40 / [\exp\{j \cdot (\pi/2 + \theta1)\} \cdot \{b1 + b2 \cdot \exp(j \cdot \Delta\theta2)\} \cdot \omega0] \quad (155)$$

When a variation factor dependent on the second parameter is Cp42 in equation (154), Cp42=rk[p4,ω2]·exp(j·θ00[p4,ω2]) holds, and the remaining portion is a constant which is provided at the time of calibration. The variation factor Cp42 is represented by equation (154).

$$Cp42 = EdA42 / [\exp\{j \cdot (\pi/2 + \theta1)\} \cdot \{b1 + b2 \cdot \exp(j \cdot \Delta\theta2)\} \cdot \omega2] \quad (156)$$

Letting m2b and θ2b be the magnitude and angle of [exp{j·(π/2+θ1)}·{b1+b2·exp(j·Δθ2)}] in equations (155) and (156), m2b and θ2b are represented by equations (120) and (121).

Upon applying equations (120) and (121) to equation (155), a magnitude rk[p4,ω0] of the variation factor Cp40 and an angle θ00[p4,ω0] thereof from the real axis are represented by $$rk[p4,\omega0]=|EdA40|/(m2b \cdot \omega0) \quad (157)$$

$$\theta00[p4,\omega0]=\angle EdA40-\theta2b \quad (158)$$

Upon applying equations (120) and (121) to equation (156), a magnitude rk[p4,ω2] of the variation factor Cp42 and an angle θ00[p4,ω2] thereof from the real axis are represented by $$rk[p4,\omega2]=|EdA42|/(m2b \cdot \omega2) \quad (159)$$

$$\theta00[p4,\omega2]=\angle EdA42-\theta2b \quad (160)$$

When the ratio between the variation factors Cp42 and Cp40 is Cn4, the ratio Cn4 is represented by the following equation.

$$Cn4 = Cp42/Cp40 \quad (161)$$
$$= (rk[p4,\omega2]/rk[p4,\omega0]) \cdot$$
$$\exp\{j \cdot (\theta00[p4,\omega2] - \theta00[p4,\omega0])\}$$

In this case, the magnitude (rk[p4,ω2]/rk[p4,ω0]) of the ratio Cn4 and the angle (θ00[p4,ω2]−θ00[p4,ω0]) with respect to the real axis are represented by the following equations.

$$rk[p4,\omega2]/rk[p4,\omega0] = (|EdA42|/|EdA40|) \cdot (\omega0/\omega2) \quad (162)$$

$$\theta00[p4,\omega2]-\theta00[p4,\omega0]=\angle EdA42-\angle EdA40 \quad (163)$$

According to equations (161) to (163), it is obvious that the ratio Cn4 does not include the variation factor of the magnetic field, and the value of the second parameter p4 can be obtained by reducing error factors.

The second parameter p4 can be obtained from the relationship between the second parameter p4 and (rk[p4,ω2]/rk[p4,ω0]), which is checked in advance by measurement or the like at the time of calibration, or the relationship between the second parameter p4 and (θ00[p4,ω2]−θ00[p4,ω0]).

The specific arrangement and operation of the state detection device according to this embodiment will be described next. The state detection device according to this embodiment has the same arrangement as that of the state detection device in the second embodiment. Hence, the same reference numerals as in FIG. 30 denote the same components in this embodiment. The state detection device of this embodiment includes a measuring tube 1, electrodes 2a and 2b, first and second exciting coils 3a and 3b, a power supply unit 4, and a state quantifying unit 8a.

The state quantifying unit 8a includes a signal conversion unit 5a which obtains the amplitudes and phases of two frequency components with the first and second angular frequencies ω0 and ω2 of the resultant electromotive forces detected by the electrodes 2a and 2b, extracts ∂A/∂t components with angular frequencies ω0 and ω2, and extracts, from the ratio between the ∂A/∂t components with angular frequencies ω0 and ω2, the magnitude or phase of the ratio between the variation factors dependent on the second parameter and frequency, a state storage unit 6a (equivalent to the above-described second table) which stores in advance the relationship between the second parameter and the magnitude or phase of the ratio between the variation factors, and a state output unit 7a which obtains the second parameter corresponding to the magnitude or phase of the ratio between the extracted variation factors based on the relationship stored in the state storage unit 6a.

The power supply unit 4a repeats, in a T-sec cycle, the operation of continuing the first excitation state for T1 sec in which the first exciting current having the first angular frequency ω0 is supplied to the first exciting coil 3a and at the same time the second exciting current having the angular frequency ω0 with the phase difference Δθ2+π with respect to the first exciting current is supplied to the second exciting coil 3b, and continuing the second excitation state for T2 sec in which the frequencies of the first and second exciting currents in the first excitation state has been changed to the second angular frequency ω2. That is, T=T1+T2. Assume that the phase difference between the magnetic fields generated from the first and second exciting coils 3a and 3b is almost π(Δθ2≈0) in the first and second excitation states.

Figure 35:
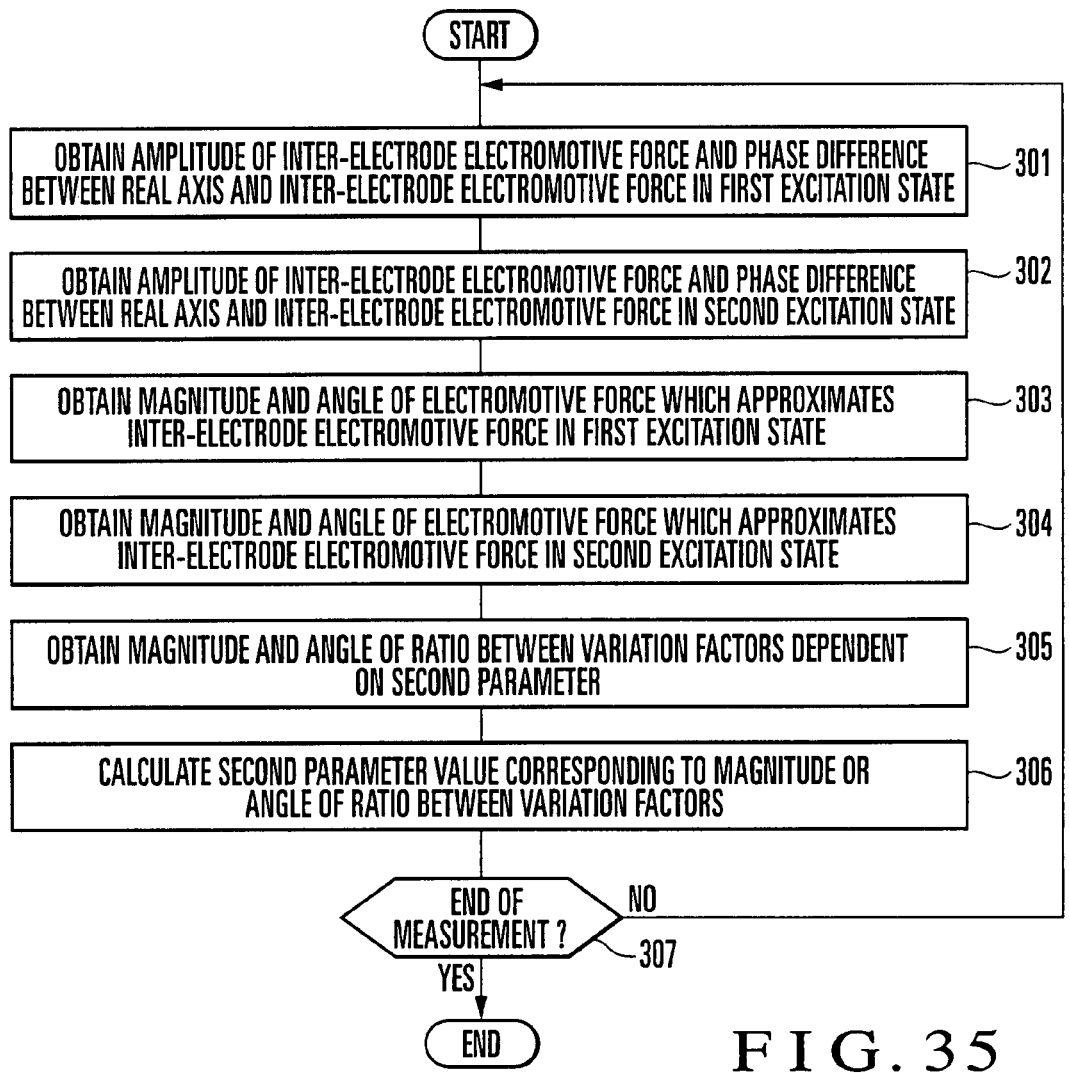
FIG. 35 is a flowchart showing the operation of a state quantifying unit according to the fourth embodiment of the present invention.

FIG. 35 is a flowchart showing the operation of the state quantifying unit 8a according to this embodiment. First of all, the signal conversion unit 5a obtains an amplitude r420R of the electromotive force E420R with the angular frequency ω0 component of the electromotive force between the electrodes 2a and 2b in the first excitation state, and obtains a phase difference φ420R between the real axis and the inter-electrode electromotive force E420R by using a phase detector (not shown) (step 301 in FIG. 35).

Subsequently, the signal conversion unit 5a obtains an amplitude r422R of the electromotive force E422R with the angular frequency $\omega 2$ component of the electromotive force between the electrodes 2a and 2b in the second excitation state, and obtains a phase difference $\phi 422R$ between the real axis and the inter-electrode electromotive force E422R by using the phase detector (step 302).

Next, the signal conversion unit 5a calculates the magnitude |EdA40| and an angle ∠EdA40 with respect to the real axis of the electromotive force EdA40 which approximates the inter-electrode electromotive force E420R (step 303) according to the following equation (step 303):

$$|EdA40|=r420R \quad (164)$$

$$\angle EdA40=\phi 420R \quad (165)$$

The signal conversion unit 5a then calculates the magnitude |EdA42| and an angle ∠EdA42 with respect to the real axis of the electromotive force EdA42 which approximates the inter-electrode electromotive force E422R according to the following equation (step 304):

$$|EdA42|=r422R \quad (166)$$

$$\angle EdA42=\phi 422R \quad (167)$$

The processing in steps 303 and 304 corresponds to the processing of obtaining the $\partial A/\partial t$ component, and is equivalent to the calculation of equations (150) and (154).

The signal conversion unit 5a extracts the variation factor Cp40 dependent on the second parameter p4 from the inter-electrode electromotive force EdA40, extracts the variation factor Cp42 dependent on the second parameter p4 from the inter-electrode electromotive force EdA42, and obtains the magnitude and angle of the ratio Cn4 between the variation factors Cp42 and Cp40 (step 305). The signal conversion unit 5a calculates the magnitude (rk[p4,$\omega 2$]/rk[p4,$\omega 0$]) of the ratio Cn4 as follows:

$$rk[p4, \omega 2]/rk[p4, \omega 0] = (|EdA42|/|EdA40|) \cdot (\omega 0/\omega 2) \quad (168)$$

The signal conversion unit 5a calculates the angle ($\theta 00[p4,\omega 2]-\theta 00[p4,\omega 0]$) with respect to the real axis of the ratio Cn4 as follows:

$$\theta 00[p4,\omega 2]-\theta 00[p4,\omega 0]=\angle EdA42-\angle EdA40 \quad (169)$$

With the above operation, the processing in step 305 is complete.

The relationship between the second parameter p4 and the magnitude (rk[p4,$\omega 2$)]/rk[p4,$\omega 0$]) of the ratio Cn4 or the relationship between the second parameter p4 and the angle ($\theta 00[p4,\omega 2]-\theta 00[p4,\omega 0]$) of the ratio Cn4 is registered in advance in the state storage unit 6a in the form of a mathematical expression or table. In step 306, the state output unit 7a calculates the value of the second parameter p4 corresponding to rk[p4,$\omega 2$]/rk[p4,$\omega 0$]) or ($\theta 00[p4,\omega 2]-\theta 00[p4,\omega 0]$) by referring to the state storage unit 6a on the basis of the magnitude (rk[p4,$\omega 2$]/rk[p4,$\omega 0$]) or angle ($\theta 00[p4,\omega 2]-\theta 00[p4,\omega 0]$) of the ratio Cn4 calculated by the signal conversion unit 5a (or acquires it from the state storage unit 6a).

The state quantifying unit 8a performs the processing in steps 301 to 306 described above in a cycle T until, for example, the operator designates the end of the measurement (YES in step 307). Note that the processing in steps 302 to 306 is performed in the second excitation state for a duration of T2 sec.

As described above, according to this embodiment, note that when the magnitudes of the magnetic fields B1 and B2 are equal to each other in a state wherein the phase difference between the magnetic fields B1 and B2 generated from the first and second exciting coils 3a and 3b is almost $\pi$, the inter-electrode electromotive forces E420R and E422R can be approximately extracted as the $\partial A/\partial t$ components when the exciting angular frequencies are $\omega 0$ and $\omega 2$, respectively. This embodiment is configured to extract the variation factors Cp40 and Cp42 dependent on the characteristic or state of the fluid or a state in the measuring tube (the second parameter p4) from the approximately extracted two $\partial A/\partial t$ components, and obtain the second parameter p4 on the basis of the magnitude or phase of the ratio between the variation factors Cp42 and Cp40. This makes it possible to accurately detect the characteristic or state of the fluid or the state in the measuring tube regardless of the flow velocity of the fluid.

As in the second embodiment, the components of the state quantifying unit 8a of this embodiment, except for the detecting unit of the inter-electrode electromotive forces E420R and E422R, can be implemented by a computer and program. In this embodiment, assume that the first exciting current having an angular frequency $\omega 0$ is supplied to the first exciting coil 3a, the second exciting current having the angular frequency $\omega 0$ with the phase difference $\Delta\theta 2$ with respect to the first exciting current is supplied to the second exciting coil 3b, and the second parameter is p4. In this case, an inter-electrode electromotive force E420 is obtained by reversing the sign of b2 in equation (146). As a result, the inter-electrode electromotive force E420 can be handled as the v×B component. Therefore, according to this embodiment, the characteristic or state of the fluid or the state in the measuring tube can be detected by using basically the same hardware arrangement as that of an electromagnetic induction type flowmeter.

In this embodiment, it suffices to extract either the magnitude (rk[p4,$\omega 2$]/rk[p4,$\omega 0$]) or angle ($\theta 00[p4,\omega 2]-\theta 00[p4,\omega 0]$) of the ratio Cn4 between the variation factors. However, the second parameter p4 can be obtained by extracting both the magnitude and angle of the component. In this case, it suffices to select either the magnitude (rk[p4,$\omega 2$]/rk[p4,$\omega 0$]) or the angle ($\theta 00[p4,\omega 2]-\theta 00[p4,\omega 0]$) which has a higher sensitivity and obtain the second parameter p4 on the basis of the selected magnitude or angle. This makes it possible to improve the detection sensitivity.

In addition, this embodiment has exemplified the case wherein the exciting frequency is switched to $\omega 0$ or $\omega 2$. However, performing excitation using exciting currents containing components with the angular frequencies $\omega 0$ and $\omega 2$ makes it unnecessary to switch the exciting frequencies. This can calculate the second parameter p4 at higher speed. For example, it suffices to use the magnetic field represented by equations (132) and (133) instead of equations (22) and (23).

An operation of detecting the resistance component of a fluid impedance will be described below as the specific example of the state detection device according to this embodiment. Upon performing excitation by using an angular frequency $\omega$, assume that Ee2[$\omega$] represents the electromotive force to be extracted from the electrodes 2a and 2b when the input impedance of the state detection device is Zin (=Rin/(1+j·$\omega$·Rin·Cin)) and the fluid impedance is Zf (=Rf), and Ee1[$\omega$] represents the electromotive force to be extracted when the input impedance is infinite. In this case, the relationship between the electromotive forces Ee2[$\omega$] and Ee1[$\omega$] have the following relation.

$$Ee2[\omega] = Ee1[\omega] \cdot Rin/\{(Rin + Rf) + \quad (170)$$
$$j \cdot \omega \cdot Cin \cdot Rin \cdot Rf\}$$

Figure 36:
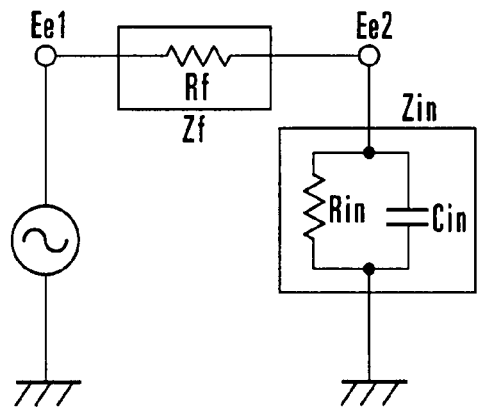
FIG. 36 is a view showing an equivalent circuit when detecting a fluid impedance according to the fourth embodiment of the present invention.
Figure 37:
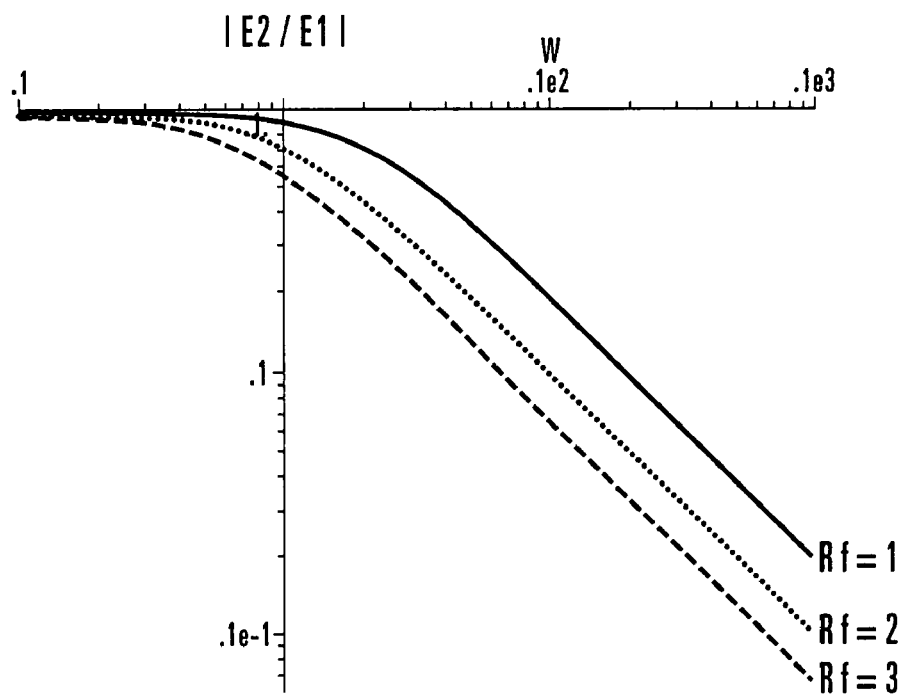
FIG. 37 is a graph showing an example of the relationship between a frequency and the magnitude of the ratio between electromotive forces according to the fourth embodiment of the present invention.

FIG. 36 shows the relationship among the input impedance Zin, fluid impedance Zf, and the electromotive forces Ee2[ω] and Ee1[ω] in the form of an equivalent circuit. When the resistance component Rin is 100 and the capacitive component is 0.5 of the input impedance, the relationship between the magnitude of Ee2[ω]/Ee1[ω] and the frequency is shown in FIG. 37. Upon applying the detection of the fluid impedance to the fourth embodiment, the following equations (171) to (174) hold.

$$Ee2[\omega 0] = E420R \quad (171)$$
$$= rk[p4, \omega 0] \cdot \exp(j \cdot \theta 00[p4, \omega 0]) \cdot$$
$$\exp\{j \cdot (\pi/2 + \theta 1)\} \cdot \{b1 + b2 \cdot \exp(j \cdot \Delta\theta 2)\} \cdot$$
$$\omega 0$$

$$Ee2[\omega 2] = E422R \quad (172)$$
$$= rk[p4, \omega 2] \cdot \exp(j \cdot \theta 00[p4, \omega 2]) \cdot$$
$$\exp\{j \cdot (\pi/2 + \theta 1)\} \cdot \{b1 + b2 \cdot \exp(j \cdot \Delta\theta 2)\} \cdot$$
$$\omega 2$$

$$Ee1[\omega 0] = \exp\{j \cdot (\pi/2 + \theta 1)\} \cdot \quad (173)$$
$$\{b1 + b2 \cdot \exp(j \cdot \Delta\theta 2)\} \cdot \omega 0$$

$$Ee1[\omega 2] = \exp\{j \cdot (\pi/2 + \theta 1)\} \cdot \quad (174)$$
$$\{b1 + b2 \cdot \exp(j \cdot \Delta\theta 2)\} \cdot \omega 2$$

The ratio Ee2[ω2]/Ee2[ω0] between the electromotive forces Ee2[ω2] and Ee2[ω0] is represented by the following equation.

$$Ee2[\omega 2]/Ee2[\omega 0] = \{rk[p4, \omega 2] \cdot \exp(j \cdot \theta 00[p4, \omega 2])\}/ \quad (175)$$
$$\{rk[p4, \omega 0] \cdot \exp(j \cdot \theta 00[p4, \omega 0])\} \cdot$$
$$\omega 2/\omega 1$$

The ratio Ee1[ω2]/Ee1[ω0] between the electromotive forces Ee1[ω2] and Ee1[ω0] is represented by the following equation.

$$Ee1[\omega 2]/Ee1[\omega 0] = \omega 2/\omega 1 \quad (176)$$

The following equation can be obtained from the relational expression $Ee2[\omega] = Ee1[\omega] \cdot Rin/\{(Rin+Rf)+j \cdot \omega \cdot Cin \cdot Rin \cdot Rf\}$.

$$Ee2[\omega 2]/Ee2[\omega 0] = \{rk[Rf, \omega 2] \cdot \exp(j \cdot \theta 00[Rf, \omega 2])\}/ \quad (177)$$
$$\{rk[Rf, \omega 1] \cdot \exp(j \cdot \theta 00[Rf, \omega 1])\}$$
$$= [Rin/\{(Rin + Rf) + j \cdot \omega 2 \cdot Cin \cdot Rin \cdot Rf\}]/$$
$$[Rin/\{(Rin + Rf) + j \cdot \omega 0 \cdot Cin \cdot Rin \cdot Rf\}]$$

Figure 38:
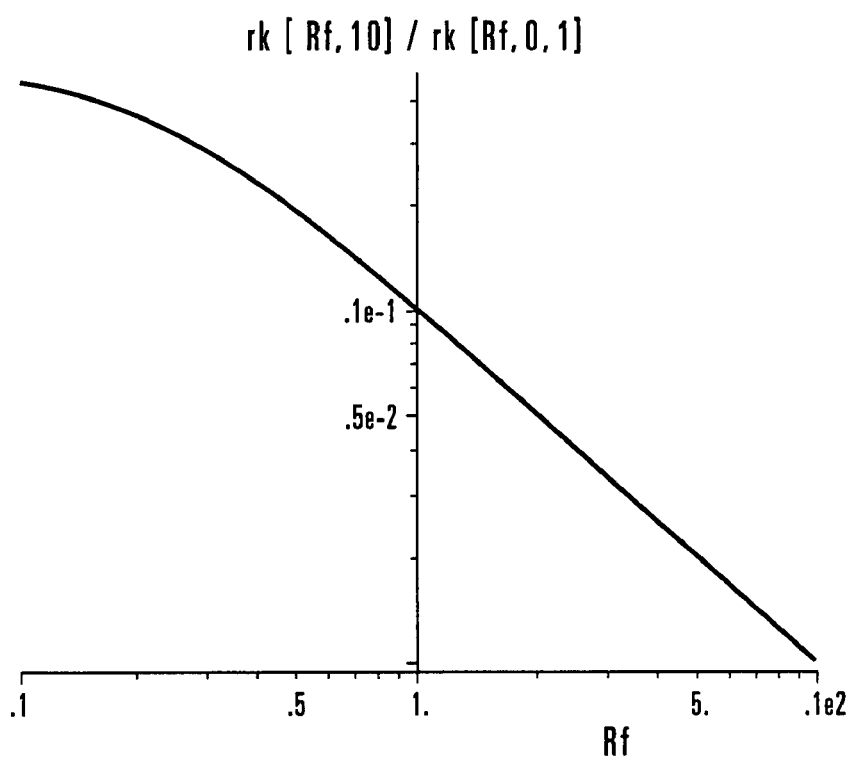
FIG. 38 is a graph showing an example of the relationship between the magnitude of the ratio between variation factors and the resistance component of the fluid impedance according to the fourth embodiment of the present invention.

Assume that the value of the resistance component Rf (second parameter p4) of the fluid impedance is obtained on the basis of the ratio of the magnitudes. FIG. 38 shows the relationship between the resistance component Rf and the magnitude |rk[Rf,ω2]/rk[Rf,ω0]| of the ratio between variation factors when ω0=0.1 and ω2=10. Obtaining this relationship by a theoretical formula at the time of design or measurement at the time of calibration, and storing it in the state storage unit 6a make it possible to obtain the resistance component Rf of the fluid impedance in step 306 on the basis of the magnitude |rk[Rf,ω2]/rk[Rf,ω0]| of the ratio between the variation factors obtained in step 305. For example, when the ratio between the variation factors is 0.009996136860, the value of the resistance component Rf is 1 with reference to FIG. 38.

Fifth Embodiment

The fifth embodiment of the present invention will be described next. A state detection device according to this embodiment includes two exciting coils and a pair of electrodes, and has the same arrangement as that of the state detection device shown in FIG. 5 except for the signal processing system. The principle of this embodiment will therefore be described by using reference numerals in FIG. 5. This embodiment uses the second extraction method as a method of extracting a ∂A/∂t component from a resultant vector, and obtains the second parameter for a variation factor having a frequency characteristic. In this embodiment, two second parameter values are obtained. Of the two second parameters, one is the third parameter, and the other is the fourth parameter.

Assume that the first exciting current having an angular frequency ω0 is supplied to a first exciting coil 3a, the second exciting current having the angular frequency ω0 with the phase difference Δθ2+π with respect to the first exciting current is supplied to a second exciting coil 3b, the third parameter is p5, and the fourth parameter is q5. In this case, an inter-electrode electromotive force E520R is represented by the following equation according to equations (30), (85), and (86).

$$E520R = rk[p5, q5, \omega 0] \cdot \exp\{j \cdot (\theta 1 + \theta 00[p5, q5, \omega 0])\} \cdot \quad (178)$$
$$[\exp(j \cdot \pi/2) \cdot \{b1 + b2 \cdot \exp(j \cdot \Delta\theta 2)\} \cdot \omega 0 +$$
$$\gamma \cdot \exp(j \cdot \Delta\theta 01) \cdot \{b1 - b2 \cdot \exp(j \cdot \Delta\theta 2)\} \cdot V]$$

From equations (71) and (72), equations (147) and (148) hold in equation (178). The following expressions represent an electromotive force EdA50 which approximates the inter-electrode electromotive force E520R in equation (178) by using the condition of expression (148).

$$EdA50 \approx E520R \quad (179)$$

$$EdA50 = rk[p5, q5, \omega 0] \cdot \exp(j \cdot \theta 00[p5, q5, \omega 0]) \cdot \quad (180)$$
$$\exp\{j \cdot (\pi/2 + \theta 1)\} \cdot \{b1 + b2 \cdot \exp(j \cdot \Delta\theta 2)\} \cdot \omega 0$$

Assume that the first exciting current having an angular frequency ω2 is supplied to the first exciting coil 3a, the second exciting current having the angular frequency ω2 with a phase difference Δθ2+π with respect to the first exciting current is supplied to the second exciting coil 3b, the third parameter is p5, and the fourth parameter is q5. In this case, an inter-electrode electromotive force E522R is represented by the following equation according to equations (30), (88) and (89).

$$E522R = rk[p5, q5, \omega2] \cdot \exp\{j \cdot (\theta1 + \theta00[p5, q5, \omega2])\} \cdot \quad (181)$$
$$[\exp(j \cdot \pi/2) \cdot \{b1 + b2 \cdot \exp(j \cdot \Delta\theta2)\} \cdot \omega2 +$$
$$\gamma \cdot \exp(j \cdot \Delta\theta01) \cdot \{b1 - b2 \cdot \exp(j \cdot \Delta\theta2)\} \cdot V]$$

Since $\omega2 > \gamma \cdot V$ holds, equation (152) holds for the inter-electrode electromotive force E522R given by equation (181) in consideration of the condition represented by equation (147). The following expressions represent the inter-electrode electromotive force EdA52 which approximates the inter-electrode electromotive force E522R in equation (181) by using the condition of expression (152).

$$EdA52 \approx E522R \quad (182)$$

$$EdA52 = rk[p5, q5, \omega2] \cdot \exp\{j \cdot \theta00[p5, q5, \omega2]\} \cdot \quad (183)$$
$$\exp(j \cdot (\pi/2 + \theta1)) \cdot \{b1 + b2 \cdot \exp(j \cdot \Delta\theta2)\} \cdot \omega2$$

In equations (180) and (183), the $\partial A/\partial t$ component in the resultant vector can be extracted by using the phase difference between the magnetic fields generated from the first and second exciting coils 3a and 3b. Equations (180) and (183) are irrelevant to the magnitude V of the flow velocity, and hence are only the component generated by $\partial A/\partial t$. The fluid state except for the flow velocity, and the state in the measuring tube can be measured by using this electromotive force difference.

When a variation factor dependent on the third and fourth parameters is Cpq50 in equation (180), Cpq50=rk[p5,q5,$\omega$0]$\cdot$exp(j$\cdot\theta$00[p5,q5,$\omega$0]) holds, and the remaining portion is a constant which is provided at the time of calibration. The variation factor Cpq50 is represented by equation (180).

$$Cpq50 = EdA50/[\exp\{j \cdot (\pi/2 + \theta1)\} \cdot \{b1 + b2 \cdot \exp(j \cdot \Delta\theta2)\} \cdot \omega0] \quad (184)$$

When a variation factor dependent on the third and fourth parameters is Cpq52 in equation (183), Cpq52=rk[p5,q5,$\omega$2]$\cdot$exp(j$\cdot\theta$00[p5,q5,$\omega$2]) holds, and the remaining portion is a constant which is provided at the time of calibration. The variation factor Cpq52 is represented by equation (183).

$$Cpq52 = EdA52/[\exp\{j \cdot (\pi/2 + \theta1)\} \cdot \{b1 + b2 \cdot \exp(j \cdot \Delta\theta2)\} \cdot \omega2] \quad (185)$$

Letting m2b and $\theta$2b be the magnitude and angle of [exp{j$\cdot$($\pi$/2+$\theta$1)}$\cdot$\{b1+b2$\cdot$exp(j$\cdot\Delta\theta$2)\}] in equations (184) and (185), m2b and $\theta$2b are represented by equations (120) and (121).

Upon applying equations (120) and (121) to equation (184), a magnitude rk[p5,q5,$\omega$0] of the variation factor Cpq50 and an angle $\theta$00[p5,q5,$\omega$0] thereof from the real axis are represented by $$rk[p5,q5,\omega0]=|EdA50|/(m2b \cdot \omega0) \quad (186)$$

$$\theta00[p5,q5,\omega0]=\angle EdA50-\theta2b \quad (187)$$

Upon applying equations (120) and (121) to equation (185), a magnitude rk[p5,q5,$\omega$2] of the variation factor Cpq52 and an angle $\theta$00[p5,q5,$\omega$2] thereof from the real axis are represented by $$rk[p5,q5,\omega2]=|EdA52|/(m2b \cdot \omega2) \quad (188)$$

$$\theta00[p5,q5,\omega2]=\angle EdA52-\theta2b \quad (189)$$

The parameters p5 and q5 can be obtained from the relationship between the parameters p5 and q5 and rk[p5,q5,$\omega$0] and rk[p5,q5,$\omega$2], which is checked in advance by measurement or the like at the time of calibration, or the relationship between the parameters p5 and q5 and $\theta$00[p5,q5,$\omega$0] and $\theta$00[p5,q5,$\omega$2].

The specific arrangement and operation of the state detection device according to this embodiment will be described next. The state detection device according to this embodiment has the same arrangement as that of the state detection device in the second embodiment. Hence, the same reference numerals as in FIG. 30 denote the same components in this embodiment. The state detection device of this embodiment includes a measuring tube 1, electrodes 2a and 2b, first and second exciting coils 3a and 3b, a power supply unit 4, and a state quantifying unit 8a.

The state quantifying unit 8a includes a signal conversion unit 5a which obtains the amplitudes and phases of a plurality of frequency components of the resultant electromotive forces detected by the electrodes 2a and 2b, extracts $\partial A/\partial t$ components with the plurality of frequency components, and extracts, from the extracted $\partial A/\partial t$ components, the magnitudes or phases of the variation factors dependent on the plurality of second parameters and frequencies, a state storage unit 6a (equivalent to the above-described third table) which stores in advance the relationship between the plurality of second parameters and the magnitudes or phases of the variation factors with the plurality of frequency components, and a state output unit 7a which obtains the plurality of second parameters corresponding to the magnitudes or phases of the extracted variation factors based on the relationship stored in the state storage unit 6a.

Figure 39:
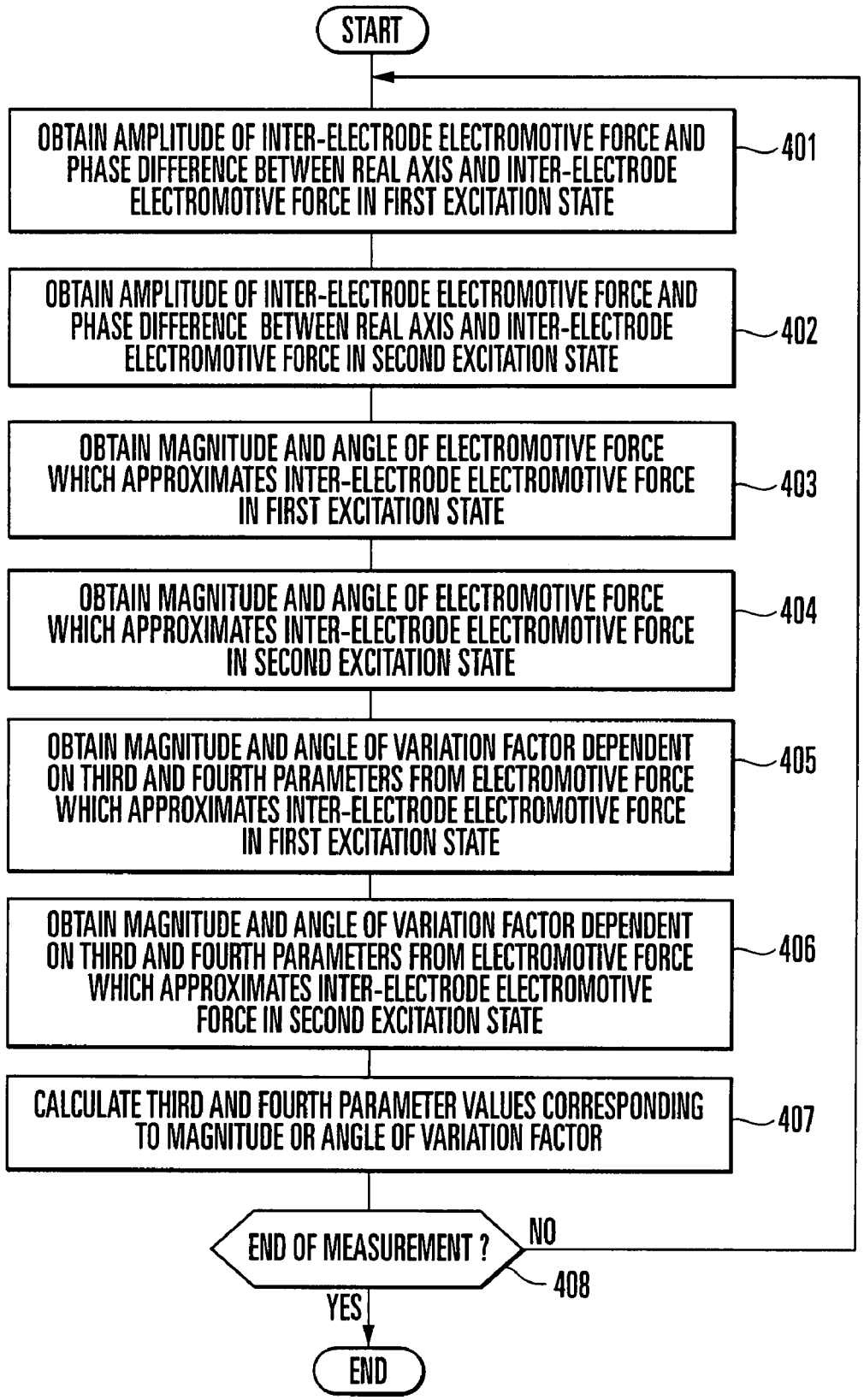
FIG. 39 is a flowchart showing the operation of a state quantifying unit according to the fifth embodiment of the present invention.

The operation of the power supply unit 4a is the same as that in the fourth embodiment. FIG. 39 is a flowchart showing the operation of the state quantifying unit 8a according to this embodiment. First of all, the signal conversion unit 5a obtains an amplitude r520R of the electromotive force E520R with the angular frequency $\omega$0 component of the electromotive force between the electrodes 2a and 2b in the first excitation state in which the exciting angular frequency is $\omega$0, and obtains a phase difference $\phi$520R between the real axis and the inter-electrode electromotive force E520R by using a phase detector (not shown) (step 401 in FIG. 39).

Subsequently, the signal conversion unit 5a obtains an amplitude r522R of the electromotive force E522R with the angular frequency $\omega$2 component of the electromotive force between the electrodes 2a and 2b in the second excitation state in which the exciting angular frequency is $\omega$2, and obtains a phase difference $\phi$522R between the real axis and the inter-electrode electromotive force E522R by using the phase detector (step 402).

Next, the signal conversion unit 5a calculates the magnitude |EdA50| and an angle $\angle$EdA50 with respect to the real axis of the electromotive force EdA50 which approximates the inter-electrode electromotive force E520R according to the following equation (step 403):

$$|EdA50|=r520R \quad (190)$$

$$\angle EdA50=\phi520R \quad (191)$$

The signal conversion unit 5a then calculates the magnitude |EdA52| and an angle $\angle$EdA52 with respect to the real axis of the electromotive force EdA52 which approximates the inter-electrode electromotive force E522R according to the following equation (step 404):

$$|EdA52|=r522R \quad (192)$$

$$\angle EdA52=\phi522R \quad (193)$$

The processing in steps 403 and 404 corresponds to the processing of obtaining the ∂A/∂t component, and is equivalent to the calculation of equations (180) and (183).

The signal conversion unit 5a calculates, from the inter-electrode electromotive force EdA50, the magnitude rk[p5,q5,ω0] of the variation factor Cpq50 dependent on the third and fourth parameters p5 and q5 and the angle θ00[p5,q5,ω0] with respect to the real axis as follows (step 405):

$$rk[p5,q5,\omega 0]=|EdA50|/(m2b\cdot\omega 0) \quad (194)$$

$$\theta 00[p5,q5,\omega 0]=\angle EdA50-\theta 2b \quad (195)$$

The signal conversion unit 5a also calculates, from the inter-electrode electromotive force EdA52, the magnitude rk[p5,q5,ω2] of the variation factor Cpq52 dependent on the third and fourth parameters p5 and q5 and the angle θ00[p5,q5,ω2] with respect to the real axis as follows (step 406):

$$rk[p5,q5,\omega 2]=|EdA52|/(m2b\cdot\omega 2) \quad (196)$$

$$\theta 00[p5,q5,\omega 2]=\angle EdA52-\theta 2b \quad (197)$$

Note that m2b and θ2b (the amplitude b1 of the magnetic field B1 generated from the first exciting coil 3a, the amplitude b2 of the magnetic field B2 generated from the second exciting coil 3b, the phase difference θ1 between the magnetic field B1 and ω0·t, and Δθ2) are constants which can be obtained in advance by calibration or the like.

The relationship between the third and fourth parameters p5 and q5 and the magnitudes rk[p5,q5,ω0] and rk[p5,q5,ω2] of the variation factors Cpq50 and Cpq52 or the relationship between the parameters p5 and q5 and the angles θ00[p5,q5,ω0] and θ00[p5,q5,ω2] of the variation factors Cpq50 and Cpq52 is registered in advance in the state storage unit 6a in the form of a mathematical expression or table.

The state output unit 7a calculates the values of the third and fourth parameters p5 and q5 corresponding to the magnitudes rk[p5,q5,ω2] and rk[p5,q5,ω0]) or angles θ00[p5,q5,ω0] and θ00[p5,q5,ω2] by referring to the state storage unit 6a on the basis of the magnitudes rk[p5,q5,ω0] and rk[p5,q5,ω2]) or angles θ00[p5,q5,ω0] and θ00[p5,q5,ω2]) of the variation factors Cpq50 and Cpq52 calculated by the signal conversion unit 5a (step 407).

The state quantifying unit 8a performs the processing in steps 401 to 407 described above in a cycle T until, for example, the operator designates the end of the measurement (YES in step 408). Note that the processing in steps 402 to 407 is performed in the second excitation state for a duration of T2 sec.

As described above, according to this embodiment, note that when the magnitudes of the magnetic fields B1 and B2 are equal to each other in a state wherein the phase difference between the magnetic fields B1 and B2 generated from the first and second exciting coils 3a and 3b is almost π, the inter-electrode electromotive forces E520R and E522R can be approximately extracted as the ∂A/∂t components when the exciting angular frequencies are (ω0 and ω2, respectively. This embodiment is configured to extract the variation factors Cp50 and Cp52 dependent on the characteristic or state of the fluid or a state in the measuring tube (the third and fourth parameters p5 and q5) from the approximately extracted two ∂A/∂t components, and obtain the third and fourth parameters p5 and q5 on the basis of the magnitude or phase of the variation factors Cp52 and Cp50. This makes it possible to accurately detect the characteristic or state of the fluid or the state in the measuring tube regardless of the flow velocity of the fluid.

As in the second embodiment, the components of the state quantifying unit 8a of this embodiment, except for the detecting unit of the inter-electrode electromotive forces E520R and E522R, can be implemented by a computer and program. In this embodiment, assume that the first exciting current having an angular frequency ω0 is supplied to the first exciting coil 3a, the second exciting current having the angular frequency ω0 with the phase difference Δθ2 with respect to the first exciting current is supplied to the second exciting coil 3b, the third parameter is p5, and the fourth parameter is q5. In this case, an inter-electrode electromotive force E520 is obtained by reversing the sign of b2 in equation (178). As a result, the inter-electrode electromotive force E520 can be handled as the v×B component. Therefore, according to this embodiment, the characteristic or state of the fluid or the state in the measuring tube can be detected by using basically the same hardware arrangement as that of an electromagnetic induction type flowmeter.

In this embodiment, it suffices to extract either the magnitudes rk[p5,q5,ω0] and rk[p5,q5,ω2]) or angles θ00[p5,q5,ω0] and θ00[p5,q5,ω2] of the variation factors Cpq50 and Cpq52. However, the third and fourth parameters p5 and q5 can be obtained by extracting both the magnitude and angle of the component. In this case, it suffices to select either the magnitudes rk[p5,q5,ω0] and rk[p5,q5,ω2] or the angles θ00[p5,q5,ω0] and θ00[p5,q5,ω2] which has a higher sensitivity and obtain the third and fourth parameters p5 and q5 on the basis of the selected magnitude or angle. This makes it possible to improve the detection sensitivity.

In addition, this embodiment has exemplified the case wherein the exciting frequency is switched to ω0 or ω2. However, performing excitation using exciting currents containing components with the angular frequencies ω0 and ω2 makes it unnecessary to switch the exciting frequencies. This can calculate the parameters p5 and q5 at higher speed. For example, it suffices to use the magnetic field represented by equations (132) and (133) instead of equations (22) and (23).

An operation of detecting the resistance component and capacitive component of a fluid impedance will be described below as the specific example of the state detection device according to this embodiment. Upon performing excitation by using an angular frequency ω, assume that Ee2[ω] represents the electromotive force to be extracted from the electrodes 2a and 2b when the input impedance of the state detection device is Zin (=Rin/(1+j·ω·Rin·Cin)) and the fluid impedance is Zf (=Rf/(1+j·ω·Rf·Cf)), and Ee1[ω] represents the potential to be extracted when the input impedance is infinite. In this case, the relationship between the electromotive forces Ed2[ω] and Ee1[ω] is represented by the following equation.

$$Ee2[\omega]=Ee1[\omega]\cdot Zf[\omega]/(Zin[\omega]+Zf[\omega]) \quad (198)$$

Figure 40:
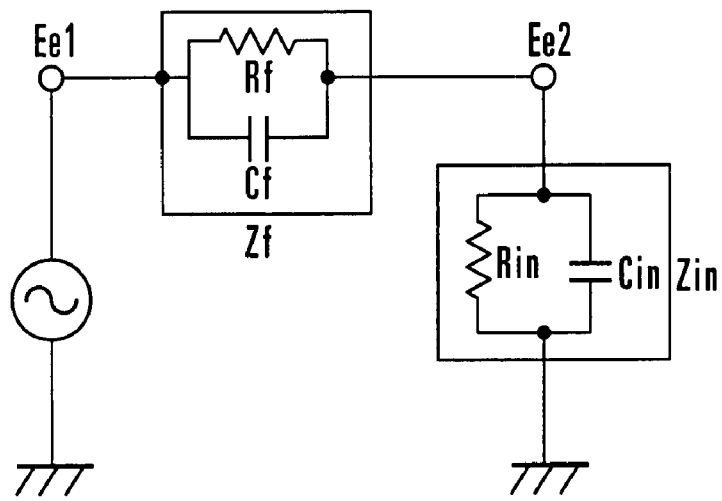
FIG. 40 is a view showing an equivalent circuit when detecting a fluid impedance according to the fifth embodiment of the present invention.
Figure 41:
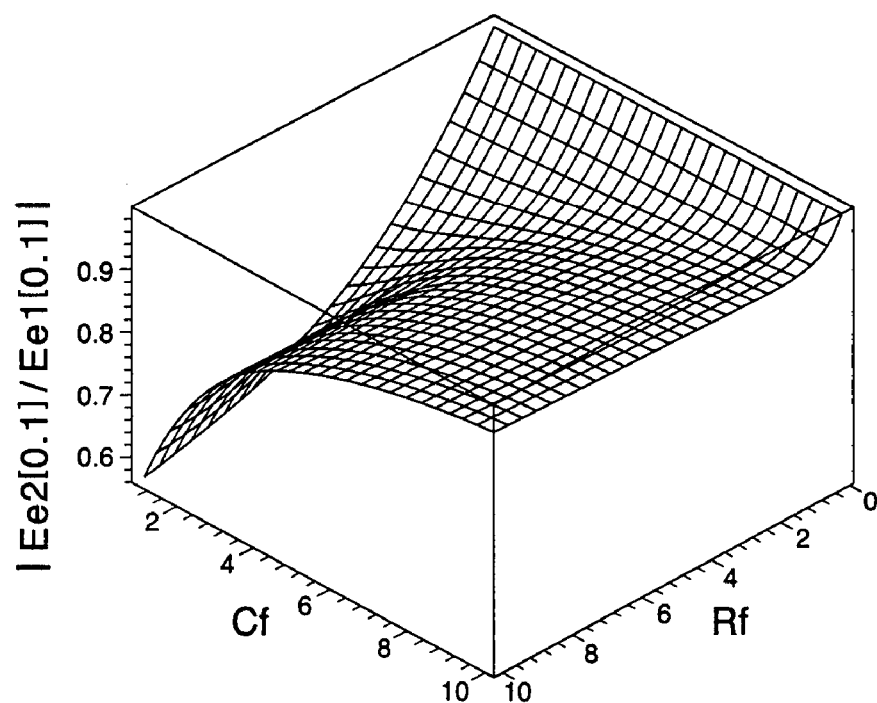
FIG. 41 is a graph showing an example of the relationship between the magnitude of the ratio between variation factors and the resistance component of the fluid impedance according to the fifth embodiment of the present invention.

FIG. 40 is a view showing the relationship among the input impedance Zin, fluid impedance Zf, and the electromotive forces Ed2[ω] and Ee1[ω] in the form of an equivalent circuit. When the resistance component Rin=10 and the capacitive component=0.5 in the input impedance, and ω=0.1, the relationship between the magnitude of Ee2[0.1]/Ee1[0.1] and the resistance component Rf and capacitive component Cf of the fluid impedance is shown in FIG. 41. Similarly, when Rin=10, Cin=0.5, and ω2=0.01, the relationship between the magnitude of Ee2[0.01]/Ee1[0.01] and the resistance component Rf and capacitive component Cf of the fluid impedance is shown in FIG. 42. Upon applying the detection of the fluid impedance to the fifth embodiment, the following equations (199) to (202) hold.

$$Ee2[\omega 0] = E520R \qquad (199)$$
$$= rk[p5, q5, \omega 0] \cdot \exp(j \cdot \theta 00[p5, q5, \omega 0]) \cdot$$
$$\exp\{j \cdot (\pi/2 + \theta 1)\} \cdot \{b1 + b2 \cdot \exp(j \cdot \Delta\theta 2)\} \cdot \omega 0$$

$$Ee2[\omega 2] = E522R \qquad (200)$$
$$= rk[p5, q5, \omega 2] \cdot \exp(j \cdot \theta 00[p5, q5, \omega 2]) \cdot$$
$$\exp\{j \cdot (\pi/2 + \theta 1)\} \cdot \{b1 + b2 \cdot \exp(j \cdot \Delta\theta 2)\} \cdot \omega 2$$

$$Ee1[\omega 0] = \exp\{j \cdot (\pi/2 + \theta 1)\} \cdot \{b1 + b2 \cdot \exp(j \cdot \Delta\theta 2)\} \cdot \omega 0 \qquad (201)$$

$$Ee1[\omega 2] = \exp\{j \cdot (\pi/2 + \theta 1)\} \cdot \{b1 + b2 \cdot \exp(j \cdot \Delta\theta 2)\} \cdot \omega 2 \qquad (202)$$

As a result, the magnitudes $rk[p5,q5,\omega 0]$ and $rk[p5,q5,\omega 2]$ and the angles $\theta 00[p5,q5,\omega 0]$ and $\theta 00[p5,q5,\omega 2]$ of the variation factors Cpq50 and Cpq52 can be obtained according to equations (194) to (197). The following equations can be obtained from the relation $Ee2[\omega]/Ee1[\omega] = Zf/(Zin+Zf)$.

$$rk[Rf, Cf, \omega 0] \cdot \exp(j \cdot \theta 00[Rf, Cf, \omega 0]) = \qquad (203)$$
$$\{Rin/(1 + j \cdot \omega 0 \cdot Cin \cdot Rin)\}/[\{Rin/(1 + j \cdot \omega 0 \cdot Cin \cdot Rin)\} +$$
$$\{Rf/(1 + j \cdot \omega 0 \cdot Cf \cdot Rf)\}]$$

$$rk[Rf, Cf, \omega 2] \cdot \exp(j \cdot \theta 00[Rf, Cf, \omega 2]) = \qquad (204)$$
$$\{Rin/(1 + j \cdot \omega 2 \cdot Cin \cdot Rin)\}/[\{Rin/(1 + j \cdot \omega 2 \cdot Cin \cdot Rin)\} +$$
$$\{Rf/(1 + j \cdot \omega 2 \cdot Cf \cdot Rf)\}]$$

Assume that the values of the resistance component Rf (third parameter p5) and capacitive component Cf (fourth parameter q5) of the fluid impedance are obtained based on the magnitude rk. In this case, if $rk[Rf,Cf,\omega 0]=Ee2[0.1]/Ee1[0.1]=0.8595658805$ when Rin=10, Cin=0.5, and $\omega 0=0.1$, the solutions Rfα and Cfα of Rf and Cf can be obtained as the intersections of the curved plane shown in FIG. 41 and a plane $Ee2[0.1]/Ee1[0.1]=0.8595658805$ (FIG. 43).

If $rk[Rf,Cf,\omega 2]=Ee2[0.01]/Ee1[0.01]=0.6759189546$ when Rin=10, Cin=0.5, and $\omega 2=0.01$, the solutions Rfβ and Cfβ of Rf and Cf can be obtained as the intersections of the curved plane shown in FIG. 42 and a plane $Ee2[0.01]/Ee1[0.01]=0.6759189546$ (FIG. 44). Referring to FIGS. 43 and 44, Rf=5 and Cf=5 can hold as the solutions which satisfy both the exciting frequency $\omega 0$ and $\omega 2$.

Obtaining the relationship shown in FIGS. 41 and 42 by a theoretical formula at the time of design or by measurement at the time of calibration and storing it in the state storage unit 6a in advance make it possible to obtain the resistance component Rf and capacitive component Cf of the fluid impedance in step 407 on the basis of the magnitude $rk[p5,q5,\omega 0]$ of the variation factor Cpq50 obtained in step 405 and the magnitude $rk[p5,q5,\omega 2]$ of the variation factor Cpq52 obtained in step 406.

Note that candidates of solutions of the parameters p5 and q5 are actually obtained as curved lines on the basis of the value of the magnitude $rk[p5,q5,\omega 0]$ of the variation factor Cpq50 with the exciting angular frequency $\omega 0$, and the curved plane shown in FIG. 41 stored in the state storage unit 6a. Furthermore, candidates of solutions of the parameters p5 and q5 are obtained as curved lines on the basis of the value of the magnitude $rk[p5,q5,\omega 2]$ of the variation factor Cpq52 with the exciting angular frequency $\omega 2$, and the curved plane shown in FIG. 42 stored in the state storage unit 6a. Hence, the intersections between the candidates of the solutions obtained from equations of the curved planes shown in FIGS. 41 and 42 are solutions of the parameters p5 and q5.

More specifically, the curved line is subdivided, and equations of the two straight lines hold in the neighborhood of the solutions as represented by equations (95) and (96).

$$p5/a0+q5/b0+z0/c0=1 \qquad (205)$$

$$p5/a2+q5/b2+z2/c2=1 \qquad (206)$$

FIG. 45 shows an example of the straight line obtained from equations (205) and (206). Selecting a section having an intersection of two subdivided lines, and solving two simultaneous equations by, e.g., the program of the Gaussian elimination method make it possible to obtain the solutions of the parameters p5 and q5. Even when two or more second parameters are used, the solutions can be obtained using the same scheme. This calculation can be easily implemented by a computer.

Sixth Embodiment

The sixth embodiment of the present invention will be described next. A state detection device of this embodiment is obtained by adding one electrode to that in the first embodiment, using the above-described third principle. The state detection device according to this embodiment includes one exciting coils and two pairs of electrodes, and has the same arrangement as that of the state detection device shown in FIG. 13 except for the signal processing system. The principle of this embodiment will therefore be described by using reference numerals in FIG. 13. If the second electrode to be newly added is placed on the same side as the existing first electrode, the resultant arrangement is a redundant arrangement of that shown in the first embodiment. Therefore, the second electrode needs to be placed on a side different from that of the first electrode through the exciting coil. This embodiment uses the first extraction method as a method of extracting a $\partial A/\partial t$ component from a resultant vector, and obtains the first parameter irrelevant to the exciting frequency.

Assume that the exciting current having an angular frequency $\omega 0$ is supplied to an exciting coil 3, and the first parameter is p6. In this case, the difference E630d between the first inter-electrode electromotive force between electrodes 2a and 2b and the second inter-electrode electromotive force between electrodes 2c and 2d is represented by the following equation according to equations (54), (68), and (75).

$$E630d = rk[p6] \cdot \exp\{j \cdot (\theta 3 + \theta 00[p6])\} \cdot \qquad (207)$$
$$\exp(j \cdot \pi/2) \cdot \{b3 + b4 \cdot \exp(j \cdot \Delta\theta 4)\} \cdot \omega 0 +$$
$$\gamma \cdot \exp(j \cdot \Delta\theta 01) \cdot \{b3 - b4 \cdot \exp(j \cdot \Delta\theta 4)\} \cdot V]$$

Assume that the exciting current having an angular frequency θ2 is supplied to the exciting coil 3, and the first parameter is p6. In this case, the difference E632d between the first inter-electrode electromotive force between the electrodes 2a and 2b and the second inter-electrode electromotive force between the electrodes 2c and 2d is represented by the following equation according to equations (54), (70) and (75).

$$E632d = rk[p6] \cdot \exp\{j \cdot (\theta 3 + \theta 00[p6])\} \cdot \qquad (208)$$
$$[\exp(j \cdot \pi/2) \cdot \{b3 + b4 \cdot \exp(j \cdot \Delta\theta 4)\} \cdot \omega 2 +$$
$$\gamma \cdot \exp(j \cdot \Delta\theta 01) \cdot \{b3 - b4 \cdot \exp(j \cdot \Delta\theta 4)\} \cdot V]$$

In this case, if a distance d3 from a plane PLN3 including the axis of the exciting coil 3 to the electrode axis EAX1 connecting the electrodes 2a and 2b is almost equal to a distance d4 from the plane PLN3 to the electrode axis EAX2 connecting the electrodes 2c and 2d (d3≈d4), then b3≈b4 and Δθ4≈0. In this case, equations (207) and (208) are rewritten as follows:

$$E630d = rk[p6] \cdot \exp\{j \cdot (\theta 3 + \theta 00[p6])\} \cdot \{\exp(j \cdot \pi/2) \cdot 2 \cdot b3 \cdot \omega 0\} \quad (209)$$

$$E632d = rk[p6] \cdot \exp\{j \cdot (\theta 3 + \theta 00[p6])\} \cdot \{\exp(j \cdot \pi/2) \cdot 2 \cdot b3 \cdot \omega 2\} \quad (210)$$

That is, since the electromotive force differences E630d and E632d are almost only the electromotive forces based on the ∂A/∂t components, computation errors in the extraction of the ∂A/∂t component can be reduced. This point is a difference in terms of technical significance between the first and sixth embodiments. Note, however, that the subsequent theoretical development will be made assuming that b3≠b4 and Δθ4 ≠0.

Letting EdA6 be the difference between the electromotive force differences E630d and E632d, the difference EdA6 is given by $$\begin{aligned}EdA6 &= (E630d - E632d) \\ &= rk[p6] \cdot \exp(j \cdot \theta 00[p6]) \cdot \exp\{j \cdot (\pi/2 + \theta 3)\} \cdot \\ &\quad \{b3 + b4 \cdot \exp(j \cdot \Delta\theta 4)\} \cdot (\omega 0 - \omega 2)\end{aligned} \quad (211)$$

In equation (211), the ∂A/∂t component in the resultant vector can be extracted by using the output difference between different frequency components. Equation (211) is irrelevant to the magnitude V of the flow velocity, and hence is only the component generated by ∂A/∂t. The fluid state except for the flow velocity, and the state in the measuring tube can be measured by using the difference EdA6.

When a variation factor dependent on the first parameter is Cp6, Cp6=rk[p6]·exp(j·θ00[p6]) holds, and the remaining portion is a constant which is provided at the time of calibration. The variation factor Cp6 is represented by equation (211).

$$Cp6 = EdA6 / [\exp\{j \cdot (\pi/2 + \theta 3)\} \cdot \{b3 + b4 \cdot \exp(j \cdot \Delta\theta 4)\} \cdot (\omega 0 - \omega 2)] \quad (212)$$

Letting m3b and θ3b be the magnitude and angle of [exp{j·(π/2+θ3)}·{b3+b4·exp(j·Δθ4)}] in equation (212), m3b and θ3b are represented by the following equation.

$$m3b = \{b3^2 + b4^2 + b3 \cdot b4 \cdot \cos(\Delta\theta 4)\}^{1/2} \quad (213)$$

$$\theta 3b = \tan^{-1}[\{b4 \cdot \sin(\Delta\theta 4)\}/\{b3 + b4 \cdot \cos(\Delta\theta 4)\}] - (\pi/2 + \theta 3) \quad (214)$$

According to equations (212) to (214), the magnitude rk[p6] of the variation component Cp6 and the angle θ00[p6] with respect to the real axis are represented by $$rk[p6] = |EdA1|/(m3b \cdot (\omega 0 - \omega 2)) \quad (215)$$

$$\theta 00[p6] = \angle EdA1 - \theta 3b \quad (216)$$

The first parameter p6 can be obtained from the relationship between the first parameter p6 and rk[p6], which is checked in advance by measurement or the like at the time of calibration, or the relationship between the first parameter p6 and the angle θ00[p6].

Figure 46:
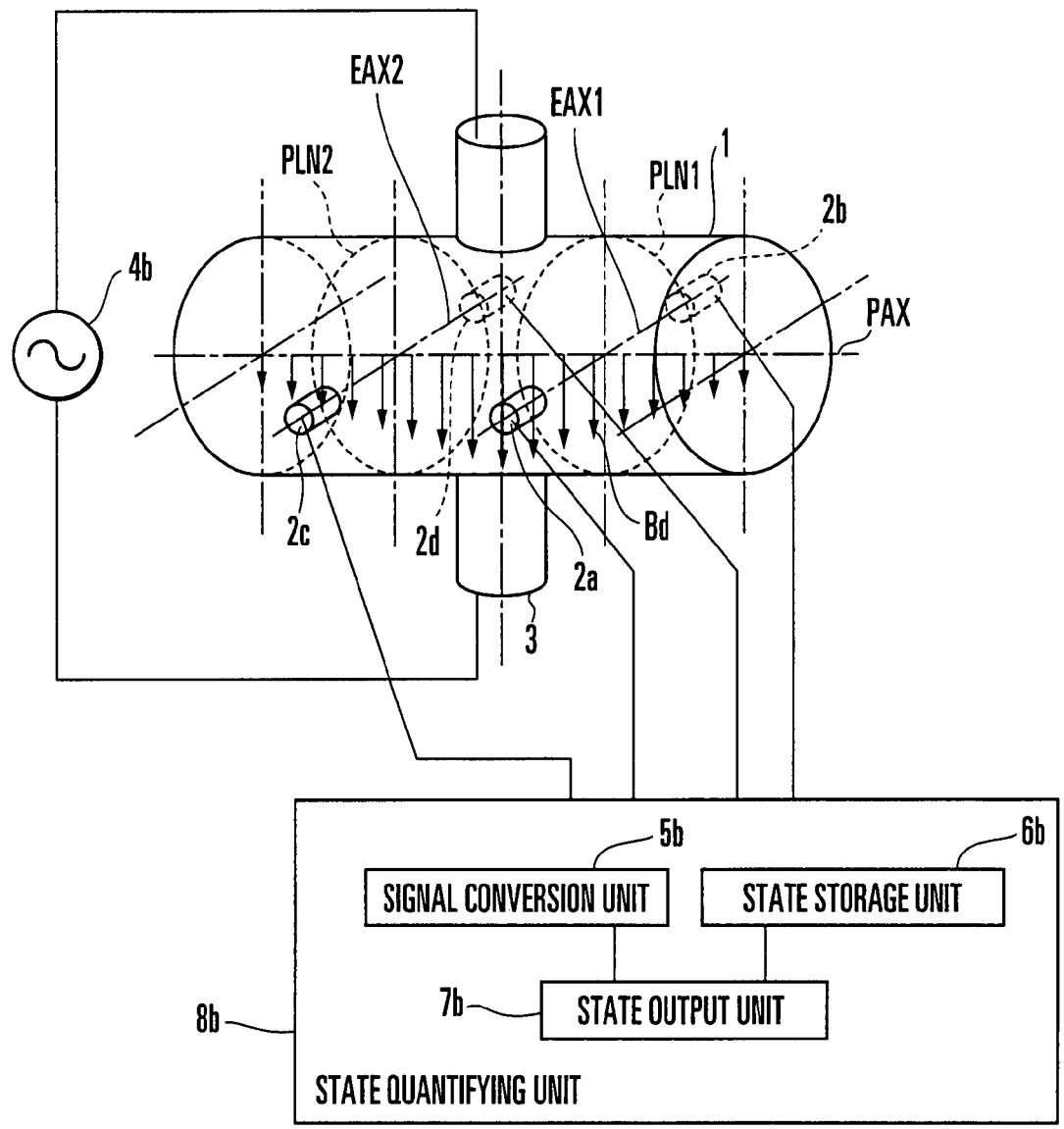
FIG. 46 is a block diagram showing the arrangement of a state detection device according to the sixth embodiment of the present invention.

The specific arrangement and operation of the state detection device according to this embodiment will be described next. FIG. 46 is a block diagram showing the arrangement of the state detection device according to this embodiment. The same reference numerals as in FIG. 13 denote the same components in this embodiment. The state detection device of this embodiment includes a measuring tube 1, first electrodes 2a and 2b, second electrodes 2c and 2d, an exciting coil 3, a power supply unit 4b, and a state quantifying unit 8b.

The state quantifying unit 8b includes a signal conversion unit 5b which obtains the amplitudes and phases of the first resultant electromotive forces detected by the first electrodes 2a and 2b and the second resultant electromotive forces detected by the electrodes 2c and 2d, obtains the electromotive force differences having the same frequency component of the first and second resultant electromotive forces with the first and second angular frequencies ω0 and ω2, extracts the difference between the electromotive force differences with the first and second angular frequencies ω0 and ω2 as a ∂A/∂t component, and extracts, from the ∂A/∂t component, the magnitude or phase of the variation factor dependent on the first parameter but independent of the frequency, a state storage unit 6b (equivalent to the above-described first table) which stores in advance the relationship between the first parameter and the magnitude or phase of the variation factors dependent on the first parameter, and a state output unit 7b which obtains the first parameter corresponding to the magnitudes or phases of the extracted variation factors based on the relationship stored in the state storage unit 6b.

The power supply unit 4b repeats, in a T-sec cycle, the operation of continuing the first excitation state for T1 sec in which the exciting current having the first angular frequency ω0 is supplied to the exciting coil 3, and continuing the second excitation state for T2 sec in which the exciting current having the second angular frequency ω2 is supplied to the exciting coil 3. That is, T=T1+T2.

Figure 47:
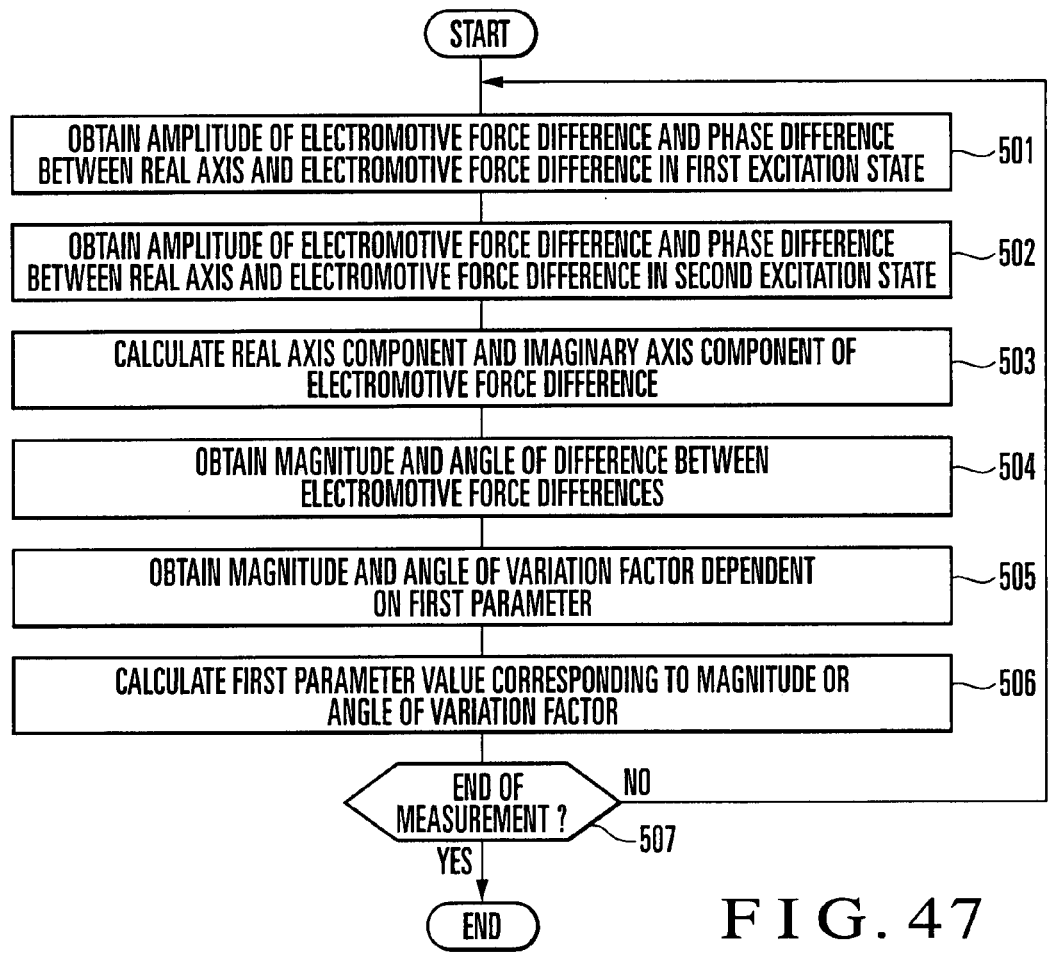
FIG. 47 is a flowchart showing the operation of a state quantifying unit according to the sixth embodiment of the present invention.

FIG. 47 is a flowchart showing the operation of the state quantifying unit 8b. First of all, the signal conversion unit 5b obtains an amplitude r630d of the difference E630d between the electromotive force of a component with the angular frequency ω0 of the first inter-electrode electromotive force between the electrodes 2a and 2b and the electromotive force with the angular frequency of a component with the angular frequency ω0 of the second inter-electrode electromotive force between the electrodes 2c and 2d, and obtains a phase difference φ630d between the real axis and the electromotive force difference E630d by using a phase detector (not shown) (step 501 in FIG. 47).

Subsequently, the signal conversion unit 5b obtains an amplitude r632d of the difference E632d between the electromotive force with the angular frequency ω2 component of the first inter-electrode electromotive force and the electromotive force with the angular frequency ω0 component of the second inter-electrode electromotive force, and obtains a phase difference φ632d between the real axis and the electromotive force difference E632d by using the phase detector (step 502).

The signal conversion unit 5b then calculates a real axis component E630dx and imaginary axis component E630dy of the electromotive force difference E630d, and a real axis component E632dx and imaginary axis component E632dy of the electromotive force difference E632d according to the following equations (step 503):

$$E630dx = r630d \cdot \cos(\phi 630d) \quad (217)$$

$$E630dy = r630d \cdot \sin(\phi 630d) \quad (218)$$

$$E632dx = r632d \cdot \cos(\phi 632d) \quad (219)$$

$$E632dy = r632d \cdot \sin(\phi 632d) \quad (220)$$

After the calculation of equations (217) to (220), the signal conversion-unit 5b obtains the magnitude and angle of the difference EdA6 between the electromotive force differences E630d and E632d (step 504). The processing in step 504 corresponds to the processing of obtaining a ∂A/∂t component, and is equivalent to the calculation of equation (211). The signal conversion unit 5b calculates a magnitude |EdA6| of the difference EdA6 according to the following equation:

$$|EdA6| = \{(E630dx - E632dx)^2 + (E630dy - E632dy)^2\}^{1/2} \quad (221)$$

The signal conversion unit 5b then calculates an angle ∠EdA6 of the difference EdA6 with respect to the real axis according to the following equation:

$$\angle EdA6 = \tan^{-1}\{(E630dy - E632dy)/(E630dx - E632dx)\} \quad (222)$$

With the above operation, the processing in step 504 is complete.

The signal conversion unit 5b then calculates the magnitude rk[p6] of the variation component Cp6 dependent on the first parameter p6 and the angle θ00[p6] with respect to the real axis from the difference EdA6 according to the following equations (step 505):

$$rk[p6] = |EdA6|/\{m3b \cdot (\omega 0 - \omega 2)\} \quad (223)$$

$$\theta 00[p6] = \angle EdA6 - \theta 3b \quad (224)$$

Note that m3b and θ3b (the amplitudes b3 and b4 of the magnetic fields B3 and B4 generated from the first exciting coil 3, and the phase differences θ3 and θ4 between the magnetic field B3 and ω0·t, and θΔ4) are constants which can be obtained in advance by calibration or the like.

The relationship between the first parameter p6 and the magnitude rk[p6] of the variation factor Cp6 or the relationship between the first parameter p6 and the angle θ00[p6] of the variation factor Cp6 is registered in advance in the state storage unit 6b in the form of a mathematical expression or table. In step 506, the state output unit 7b calculates the value of the first parameter p6 corresponding to rk[p6] or θ00[p6] by referring to the state storage unit 6b on the basis of the magnitude rk[p6] or angle θ00[p6] of the variation factor Cp6 calculated by the signal conversion unit 5b (or acquires it from the state storage unit 6b).

The state quantifying unit 8b performs the processing in steps 501 to 506 described above in a cycle T until, for example, the operator designates the end of the measurement (YES in step 507). Note that the processing in steps 502 to 506 is performed in the second excitation state for a duration of T2 sec.

As described above, according to this embodiment, note that this embodiment is configured to obtain the difference E630d between the angular frequency ω0 component of the first inter-electrode electromotive force and the angular frequency ω0 component of the second inter-electrode electromotive force, obtain the difference E632d between the angular frequency ω2 component of the first inter-electrode electromotive force and the angular frequency ω2 component of the second inter-electrode electromotive force, extract the difference EdA6 (∂A/∂t component) between the electromotive force differences E630d and E632d, extract the magnitude or phase of the variation factor Cp6 dependent on the characteristic or state of the fluid or a state in the measuring tube (the first parameter p6) from the electromotive force difference EdA6, and obtain the first parameter p6 on the basis of the magnitude or phase of the variation factor Cp6. This makes it possible to accurately detect the characteristic or state of the fluid or the state in the measuring tube regardless of the flow velocity of the fluid.

In this embodiment, the components of the state quantifying unit 8b, except for the detecting units of the electromotive force differences E630d and E632d, can be implemented by a computer comprising a CPU, storage unit, and interface and programs which control the hardware resources. In this embodiment, for example, the v×B component can be extracted by E630d−EdA6·{(ω0−ω2)/ω0}. There is known a technique of calculating the flow rate of the fluid from the v×B component in the field of a general electromagnetic flowmeter, which can be easily implemented by a computer included in the state quantifying unit 8b. Therefore, according to this embodiment, the characteristic or state of the fluid or the state in the measuring tube can be detected by using basically the same hardware arrangement as that of an electromagnetic induction type flowmeter.

In this embodiment, adjusting the distance d3 from the plane PLN3 including the axis of the exciting coil 3 to the first electrodes 2a and 2b and the distance d4 from the plane PLN3 to the second electrodes 2c and 2d allows the electromotive force differences E630d and E632d to be almost only electromotive forces based on ∂A/∂t components. With this processing, this embodiment can extract a ∂A/∂t component more effectively, and can reduce computation errors more than the first embodiment.

In this embodiment, it suffices to extract either the magnitude rk[p6] or angle θ00[p6] of the variation factor Cp6 from the difference EdA6. However, the first parameter p6 can be obtained by extracting both the magnitude and angle of the component. In this case, it suffices to select either the magnitude rk[p6] or the angle θ00[p6] which has a higher sensitivity and obtain the first parameter p6 on the basis of the selected magnitude or angle. This makes it possible to improve the detection sensitivity.

In addition, this embodiment has exemplified the case wherein the exciting frequency is switched to ω0 or ω2. However, performing excitation using exciting currents containing components with the angular frequencies ω0 and ω2 makes it unnecessary to switch the exciting frequencies. This can calculate the first parameter p6 at higher speed. For example, it suffices to use the magnetic field represented by following equations instead of equations (41) and (42).

$$B3 = b3 \cdot \cos(\omega 0 \cdot t - \theta 3) + b3 \cdot \cos(\omega 2 \cdot t - \theta 3) \quad (225)$$

$$B4 = b4 \cdot \cos(\omega 0 \cdot t - \theta 4) + b4 \cdot \cos(\omega 2 \cdot t - \theta 4) \quad (226)$$

In this embodiment, the electromotive force differences E630d and E632d are extracted from the first and second inter-electrode electromotive forces, and the difference between the electromotive force differences E630d and E632d is extracted as the ∂A/∂t component. However, the present invention is not limited to this. the electromotive force sum of the first and second inter-electrode electromotive forces may be extracted for each of the exciting angular frequencies ω0 and ω2, and the difference between the two electromotive force sums may be extracted as the ∂A/∂t components.

Figure 48:
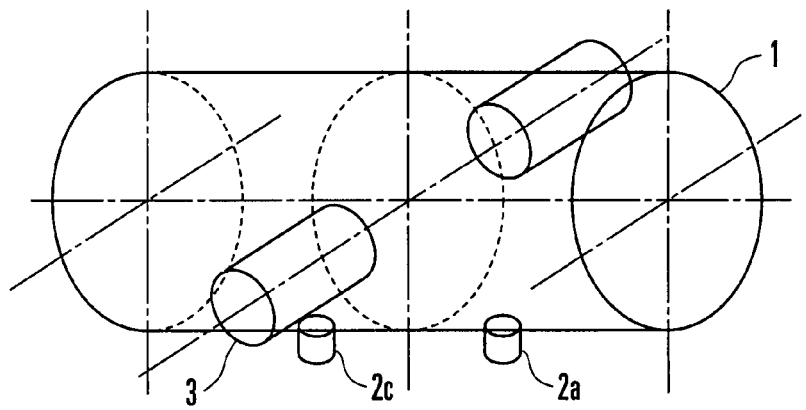
FIG. 48 is a perspective view showing the arrangement of an exciting coil and an electrode used in the state detection device according to the sixth embodiment of the present invention.
Figure 49:
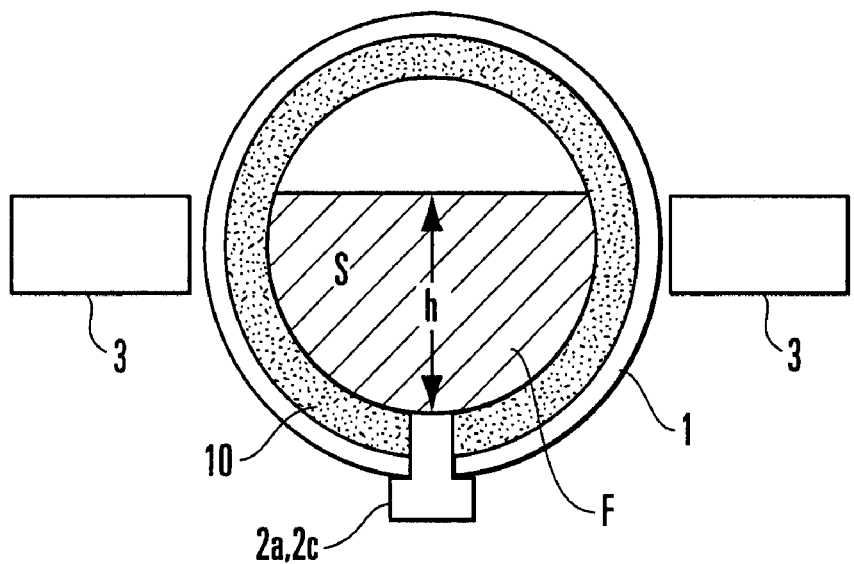
FIG. 49 is a sectional view showing the arrangement of the exciting coil and the electrode used in the state detection device according to the sixth embodiment of the present invention.

The following description will explain a specific example of the state detection device of this embodiment which detects a level or sectional area of the fluid. In this case, considering that a level h varies, as shown in FIGS. 48 and 49, the exciting coil is arranged in a direction horizontal to the measuring tube 1, and the electrodes 2a and 2c are placed under the measuring tube 1. When one first electrode and one second electrode are to be used in this manner, it suffices if an earth ring (not shown) for grounding the potential of the fluid F is provided on the measuring tube 1, the potential difference between the electrode 2a and the ground potential is set to the first inter-electrode electromotive force, and the signal conversion unit 5a detects the potential difference between the electrode 2c and the ground potential as the second inter-electrode electromotive force.

$$E730d = rk[p7] \cdot \exp\{j \cdot (\theta 3 + \theta 00[p7])\} \cdot [\exp(j \cdot \pi/2) \cdot \quad (227)$$
$$\{b3 + b4 \cdot \exp(j \cdot \Delta\theta 4)\} \cdot \omega 0 +$$
$$\gamma \cdot \exp(j \cdot \Delta\theta 01) \cdot \{b3 - b4 \cdot \exp(j \cdot \Delta\theta 4)\} \cdot V]$$

If the magnetic fields B3 and B4 generated from the exciting coil 3 are set to be equal to each other in the initial state (at the time of calibration), the difference between the magnetic fields B3 and B4 decreases afterward. The following condition holds in the following equation:

$$|b3+b4 \cdot \exp(j \cdot \Delta\theta 4)| >> |b3-b4 \cdot \exp(j \cdot \Delta\theta 4)| \quad (228)$$

Since ω0>γ·V holds, the following condition holds for the electromotive force difference E730d given by equation (227) in consideration of the condition represented by equation (228).

$$|\omega 0 \cdot \exp(j \cdot \pi/2) \cdot \{b3+b4 \cdot \exp(j \cdot \Delta\theta 4)\}| >> |\gamma \cdot V \cdot \exp$$
$$(j \cdot \Delta\theta 01) \cdot \{b3-b4 \cdot \exp(j \cdot \Delta\theta 4)\}| \quad (229)$$

The following expressions represent the electromotive force difference EdA7 which approximates the electromotive force difference E730d in equation (227) by using the condition of expression (229).

$$EdA7 \approx E730d \quad (230)$$

$$EdA7 = rk[p7] \cdot \exp\{j \cdot \theta 00[p7]\} \cdot \exp\{j \cdot (\pi/2 + \theta 3)\} \cdot \{b3 + b4 \cdot \exp(j \cdot \Delta\theta 4)\} \cdot \omega 0 \quad (231)$$

Figure 50:
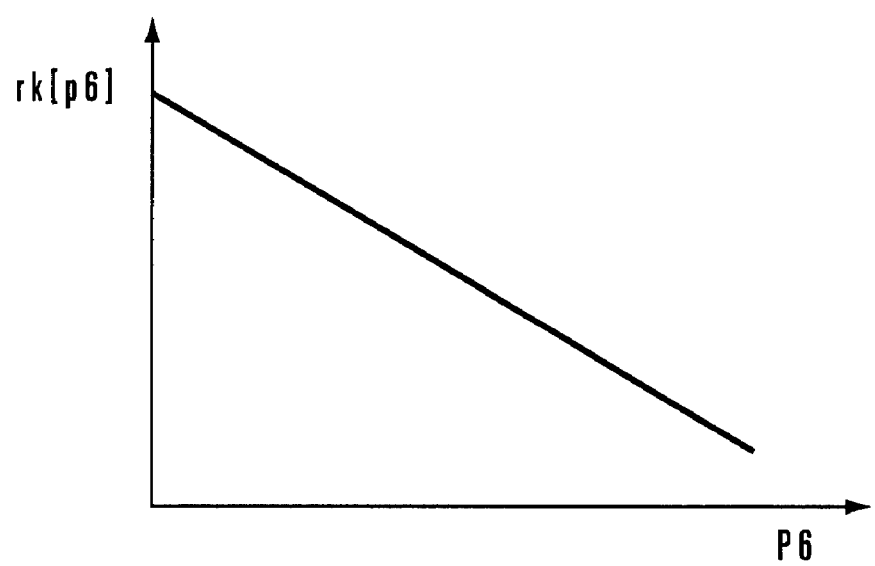
FIG. 50 is a graph showing an example of the relationship between the level or sectional area of a fluid and the magnitude of a variation factor according to the sixth embodiment of the present invention.

As the level h (sectional area S) of the fluid F varies, the value of the magnitude rk[p6] of the variation component Cp6 also varies. FIG. 50 is a graph showing an example of the relationship between the level h or sectional area S (first parameter p6) of the fluid F and the magnitude rk[p6] of the variation factor Cp6. The relationship shown in FIG. 50 changes depending on the shape or the like of the measuring tube 1. Therefore, obtaining this relationship by a theoretical formula at the time of design or measurement at the time of calibration and storing it in the state storage unit 6b in advance make it possible to obtain the level h or sectional area S of the fluid F in step 506 on the basis of the magnitude rk[p6] of the variation factor Cp6 obtained in step 505.

Seventh Embodiment

The seventh embodiment of the present invention will be described next. A state detection device according to this embodiment includes one exciting coils and two pairs of electrodes, and has the same arrangement as that of the state detection device shown in FIG. 13 except for the signal processing system. The principle of this embodiment will therefore be described by using reference numerals in FIG. 13. This embodiment uses the second extraction method as a method of extracting a ∂A/∂t component from a resultant vector, and obtains the first parameter irrelevant to an exciting frequency.

Assume that the exciting current having an angular frequency ω0 is supplied to an exciting coil 3, and the first parameter is p7. In this case, a difference between the first inter-electrode electromotive force between electrodes 2a and 2b and the second inter-electrode electromotive force between electrodes 2c and 2d is represented by the following equation according to equations (54), (68), and (75).

In equation (231), the ∂A/∂t component in the resultant vector can be extracted by using the difference between the inter-electrode electromotive forces. Equation (231) is irrelevant to the magnitude V of the flow velocity, and hence is only the component generated by ∂A/∂t. The fluid state except for the flow velocity, and the state in the measuring tube can be measured by using the electromotive force difference EdA7.

When a variation factor dependent on the first parameter is Cp7, Cp7=rk[p7]·exp(j·θ00[p7]) holds, and the remaining portion is a constant which is provided at the time of calibration. The variation factor Cp7 is represented by equation (231).

$$Cp7 = EdA7 / [\exp\{j \cdot (\pi/2 + \theta 3)\} \cdot \{b3 + b4 \cdot \exp(j \cdot \Delta\theta 4)\} \cdot \omega 0] \quad (232)$$

Letting m3b and θ3b be the magnitude and angle of [exp{j·(π/2+θ3)}·{b3+b4·exp(j·Δθ4)}] in equation (232), m3b and θ3b are represented by equations (213) and (214). Upon applying equations (213) and (214) to equation (232), a magnitude rk[p7] of the variation factor Cp7 and an angle θ00[p7] thereof from the real axis are represented by $$rk[p7] = |EdA7|/(m3b \cdot \omega 0) \quad (233)$$

$$\theta 00[p7] = \angle EdA7 - \theta 3b \quad (234)$$

The first parameter p7 can be obtained from the relationship between the first parameter p7 and rk[p7], which is checked in advance by measurement or the like at the time of calibration, or the relationship between the first parameter p7 and angle θ00[p7].

The specific arrangement and operation of the state detection device according to this embodiment will be described next. The state detection device according to this embodiment has the same arrangement as that of the state detection device in the sixth embodiment. Hence, the same reference numerals as in FIG. 46 denote the same components in this embodiment. The state detection device of this embodiment includes a measuring tube 1, first electrodes 2a and 2b, second electrodes 2c and 2d, an exciting coil 3, a power supply unit 4, and a state quantifying unit 8a.

The state quantifying unit 8b includes a signal conversion unit 5b which obtains the amplitudes and phases of the first resultant electromotive force detected by the first electrodes 2a and 2b and the second resultant electromotive force detected by the second electrodes 2c and 2d, extracts a ∂A/∂t component from the electromotive force difference between the first and second resultant electromotive forces on the basis of the amplitudes and phases, and extracts, from the ∂A/∂t component, the magnitudes or phases of the variation factors dependent on the first parameter but independent of the frequency, a state storage unit 6b (equivalent to the above-described first table) which stores in advance the relationship between the first parameter and the magnitude or phase of the variation factor dependent on the first parameter, and a state output unit 7b which obtains the first parameter corresponding to the magnitude or phase of the extracted variation factor based on the relationship stored in the state storage unit 6b.

Figure 51:
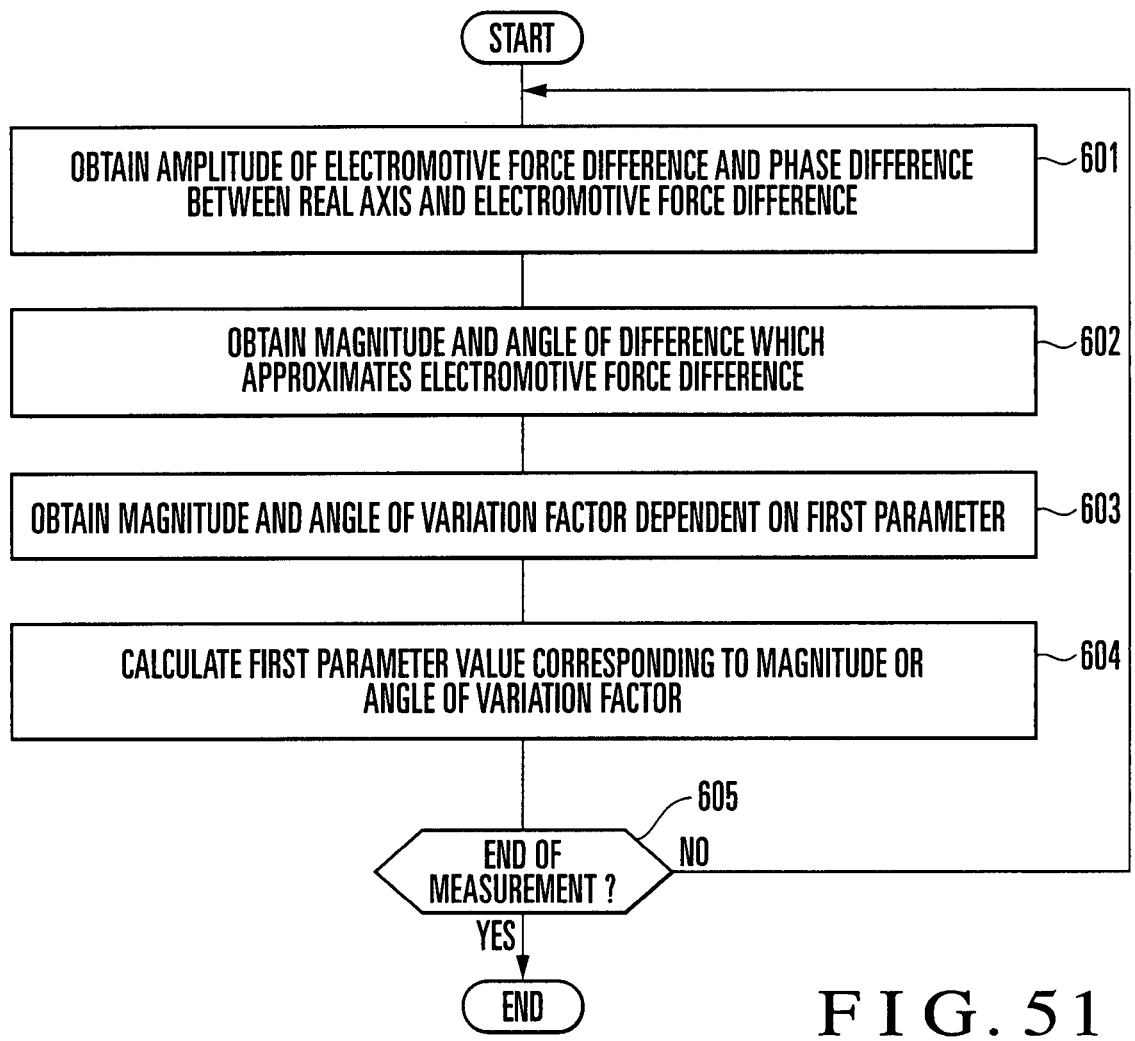
FIG. 51 is a flowchart showing the operation of a state quantifying unit according to the seventh embodiment of the present invention.

The power supply unit 4b supplies the exciting current having the angular frequency ω0 to the exciting coil 3. FIG. 51 is a flowchart showing the operation of the state quantifying unit 8b according to this embodiment. First of all, the signal conversion unit 5b obtains an amplitude r730d of the difference E730d between the electromotive force with the angular frequency ω0 component of the first inter-electrode electromotive force between the electrodes 2a and 2b and the electromotive force with the angular frequency ω0 component of the second inter-electrode electromotive force between the electrodes 2c and 2d, and obtains a phase difference ϕ730d between the real axis and the electromotive force difference E730d by using a phase detector (not shown) (step 601 in FIG. 51).

Subsequently, the signal conversion unit 5b obtains the magnitude and angle of the electromotive force difference EdA7 which approximates the electromotive force difference E730d (step 602). The processing in step 602 corresponds to the processing of obtaining the ∂A/∂t component, and is equivalent to the calculation of equation (231). The signal conversion unit 5b calculates a magnitude |EdA7| of the electromotive force difference EdA7 according to the following equation:

$$|EdA7| = r730d \quad (235)$$

The signal conversion unit 5b then calculates an angle ∠EdA7 with respect to the real axis of the electromotive force difference EdA7 according to the following equation:

$$\angle EdA7 = \phi 730d \quad (236)$$

With the above operation, the processing in step 602 is complete.

The signal conversion unit 5b calculates, from the electromotive force difference EdA7, the magnitude rk[p7] of the variation factor Cp7 dependent on the first parameter p7 and the angle θ00[p7] with respect to the real axis as follows (step 603):

$$rk[p7] = |EdA7|/(m3b \cdot \omega 0) \quad (237)$$

$$\theta 00[p7] = \angle EdA7 - \theta 3b \quad (238)$$

Note that m3b and θ3b (the amplitudes b3 and b4 generated from the exciting coil 3, the phase difference θ3 and θ4 between the magnetic field B3 and ω0·t, and Δθ4) are constants which can be obtained in advance by calibration or the like.

The relationship between the first parameter p7 and the magnitude rk[p7] of the variation factor Cp7 or the relationship between the first parameter p7 and the angle θ00[p7] of the variation factor Cp7 is registered in advance in the state storage unit 6b in the form of a mathematical expression or table. In step 604, the state output unit 7b calculates the value of the first parameter p7 corresponding to rk[p7] or θ00[p7] by referring to the state storage unit 6b on the basis of the magnitude rk[p7] or angle θ00[p7] of the variation factor Cp7 calculated by the signal conversion unit 5b (or acquires it from the state storage unit 6b). The state quantifying unit 8b performs the processing in steps 601 to 604 described above in a predetermined cycle until, for example, the operator designates the end of the measurement (YES in step 605).

As described above, according to this embodiment, note that when the magnitudes of the magnetic fields B3 and B4 generated from the exciting coil 3 are equal to each other, the electromotive force difference E730d can be approximately extracted as the ∂A/∂t components. This embodiment is configured to extract the magnitude or phase of the variation factor Cp7 dependent on the characteristic or state of the fluid or a state in the measuring tube (the first parameter p7) from the approximately extracted ∂A/∂t component, and obtain the first parameter p7 on the basis of the magnitude or phase of the variation factor Cp7. This makes it possible to accurately detect the characteristic or state of the fluid or the state in the measuring tube regardless of the flow velocity of the fluid.

As in the sixth embodiment, the components of the state quantifying unit 8b of this embodiment, except for the detecting unit of the electromotive force difference E730d, can be implemented by a computer and program. In this embodiment, assume that the exciting current having an angular frequency ω0 is supplied to the exciting coil 3, and E730s represents a sum of the first inter-electrode electromotive force between electrodes 2a and 2b and the second inter-electrode electromotive force between electrodes 2c and 2d. In this case, an inter-electrode electromotive force E730s is obtained by reversing the sign of b4 in equation (227). As a result, the inter-electrode electromotive force E730s can be handled as the v×B component. Therefore, according to this embodiment, the characteristic or state of the fluid or the state in the measuring tube can be detected by using basically the same hardware arrangement as that of an electromagnetic induction type flowmeter.

In this embodiment, it suffices to extract either the magnitude rk[p7] or angle θ00[p7] of the variation factor from the electromotive force difference EdA7. However, the first parameter p7 can be obtained by extracting both the magnitude and angle of the component. In this case, it suffices to select either the magnitude rk[p7] or the angle θ00[p7] which has a higher sensitivity and obtain the first parameter p7 on the basis of the selected magnitude or angle. This makes it possible to improve the detection sensitivity.

Eighth Embodiment

The eighth embodiment of the present invention will be described next. A state detection device according to this embodiment includes one exciting coils and two pairs of electrodes, and has the same arrangement as that of the state detection device shown in FIG. 13 except for the signal processing system. The principle of this embodiment will therefore be described by using reference numerals in FIG. 13. This embodiment uses the second extraction method as a method of extracting a ∂A/∂t component from a resultant vector, and obtains the second parameter for a variation factor having a frequency characteristic.

Assume that the exciting current having an angular frequency ω0 is supplied to an exciting coil 3, and the first parameter is p8. In this case, a difference E830d between the first inter-electrode electromotive force between electrodes 2a and 2b and the second inter-electrode electromotive force between electrodes 2c and 2d is represented by the following equation according to equations (54), (78), and (79).

$$E830d = rk[p8, \omega 0] \cdot \exp\{j \cdot (\theta 3 + \theta 00[p8, \omega 0])\} \cdot [\exp(j \cdot \pi/2) \cdot \{b3 + b4 \cdot \exp(j \cdot \Delta\theta 4)\} \cdot \omega 0 + \gamma \cdot \exp(j \cdot \Delta\theta 01) \cdot \{b3 - b4 \cdot \exp(j \cdot \Delta\theta 4)\} \cdot V] \quad (239)$$

From equations (228) and (229), the following approximate expression holds in equation (239):

$$|b3+b4\cdot\exp(j\cdot\Delta\theta 4)|>>|b3-b4\cdot\exp(j\cdot\Delta\theta 4)| \quad (240)$$

$$|\omega 0 \cdot \exp(j\cdot\pi/2)\cdot\{b3+b4\cdot\exp(j\cdot\Delta\theta 4)\}|>>|\gamma\cdot V\cdot\exp(j\cdot\Delta\theta 01)\cdot\{b3-b4\cdot\exp(j\cdot\Delta\theta 4)\}| \quad (241)$$

The following expressions represent an electromotive force difference EdA80 which approximates the electromotive force difference E830d in equation (239) by using the condition of expression (241).

$$EdA80 \approx E830d \quad (242)$$

$$EdA80 = rk[p8, \omega 0] \cdot \exp\{j \cdot \theta 00[p8, \omega 0]\} \cdot \exp\{j \cdot (\pi/2 + \theta 3)\} \cdot \{b3 + b4 \cdot \exp(j \cdot \Delta\theta 4)\} \cdot \omega 0 \quad (243)$$

Assume that the exciting current having an angular frequency ω2 is supplied to the exciting coil 3, and the first parameter is p8. In this case, the difference between the first inter-electrode electromotive force between the electrodes 2a and 2b and the second inter-electrode electromotive force between electrodes 2c and 2d is represented by the following equation according to equations (54), (81) and (82).

$$E832d = rk[p8, \omega 2] \cdot \exp\{j \cdot (\theta 3 + \theta 00[p8, \omega 2])\} \cdot [\exp(j \cdot \pi/2) \cdot \{b3 + b4 \cdot \exp(j \cdot \Delta\theta 4)\} \cdot \omega 2 + \gamma \cdot \exp(j \cdot \Delta\theta 01) \cdot \{b3 - b4 \cdot \exp(j \cdot \Delta\theta 4)\} \cdot V] \quad (244)$$

Since ω2>γ·V holds, the following condition holds for the electromotive force difference E832d given by equation (244) in consideration of the condition represented by equation (240).

$$|\omega 2 \cdot \exp(j\cdot\pi/2)\cdot\{b3+b4\cdot\exp(j\cdot\Delta\theta 4)\}|>>|\gamma\cdot V\cdot\exp(j\cdot\Delta\theta 01)\cdot\{b3-b4\cdot\exp(j\cdot\Delta\theta 4)\}| \quad (245)$$

The following expressions represent the electromotive force difference EdA82 which approximates the electromotive force difference E832d in equation (244) by using the condition of expression (245).

$$EdA82 \approx E832d \quad (246)$$

$$EdA82 = rk[p8, \omega 2] \cdot \exp\{j \cdot \theta 00[p8, \omega 2]\} \cdot \exp\{j \cdot (\pi/2 + \theta 3)\} \cdot \{b3 + b4 \cdot \exp(j \cdot \Delta\theta 4)\} \cdot \omega 2 \quad (247)$$

In equations (243) and (247), the ∂A/∂t component in the resultant vector can be extracted by using the difference between the inter-electrode electromotive forces. Equations (243) and (247) are irrelevant to the magnitude V of the flow velocity, and hence are only the component generated by ∂A/∂t. The fluid state except for the flow velocity, and the state in the measuring tube can be measured by using this electromotive force difference.

When a variation factor dependent on the second parameter is Cp80 in equation (243), Cp80=rk[p8,ω0]·exp(j·θ00[p8, ω0]) holds, and the remaining portion is a constant which is provided at the time of calibration. The variation factor Cp80 is represented by equation (243).

$$Cp80 = EdA80/[\exp\{j\cdot(\pi/2 + \theta 3)\}\cdot\{b3 + b4 \cdot \exp(j \cdot \Delta\theta 4)\}\cdot\omega 0] \quad (248)$$

When a variation factor dependent on the second parameter is Cp82 in equation (247), Cp82=rk[p8,ω2]·exp(j·θ00[p8, ω2]) holds, and the remaining portion is a constant which is provided at the time of calibration. The variation factor Cp82 is represented by equation (247).

$$Cp82 = EdA82/[\exp\{j\cdot(\pi/2 + \theta 3)\}\cdot\{b3 + b4 \cdot \exp(j \cdot \Delta\theta 4)\}\cdot\omega 2] \quad (249)$$

Letting m3b and θ3b be the magnitude and angle of [exp{j·(π/2+θ3)}·{b3+b4·exp(j·Δθ4)}] in equations (248) and (249), m3b and θ3b are represented by equations (213) and (214). Upon applying equations (213) and (214) to equation (248), a magnitude rk[p8,ω0] of the variation factor Cp80 and an angle θ00[p8,ω0] thereof from the real axis are represented by $$rk[p8,\omega 0]=|EdA80|/(m3b\cdot\omega 0) \quad (250)$$

$$\theta 00[p8,\omega 0]=\angle EdA80-\theta 3b \quad (251)$$

Upon applying equations (213) and (214) to equation (249), a magnitude rk[p8,ω2] of the variation factor Cp82 and an angle θ00[p8,ω2] thereof from the real axis are represented by $$rk[p8,\omega 2]=|EdA82|/(m3b\cdot\omega 2) \quad (252)$$

$$\theta 00[p8,\omega 2]=\angle EdA82-\theta 3b \quad (253)$$

When the ratio between the variation factors Cp82 and Cp80 is Cn8, the ratio Cn8 is represented by the following equation.

$$Cn8 = Cp82/Cp80 \quad (254)$$
$$= (rk[p8, \omega 2]/rk[p8, \omega 0]) \cdot \exp\{j\cdot(\theta 00[p8, \omega 2] - \theta 00[p8, \omega 0])\}$$

In this case, the magnitude (rk[p8,ω2]/rk[p8,ω0]) of the ratio Cn8 and the angle (θ00[p8,ω2]−θ00[p8,ω0]) with respect to the real axis are represented by the following equations.

$$rk[p8,\omega 2]/rk[p8,\omega 0]=(|EdA82|/|EdA80|)\cdot(\omega 0/\omega 2) \quad (255)$$

$$\theta 00[p8,\omega 2]-\theta 00[p8,\omega 0]=\angle EdA82-\angle EdA80 \quad (256)$$

According to equations (254) to (256), it is obvious that the ratio Cn8 does not include the variation factor of the magnetic field, and the value of the second parameter p8 can be obtained by reducing error factors.

The second parameter p8 can be obtained from the relationship between the second parameter p8 and (rk[p8,ω2]/rk[p8,ω0]), which is checked in advance by measurement or the like at the time of calibration, or the relationship between the second parameter p8 and (θ00[p8,ω2]−θ00[p8,ω0]).

The specific arrangement and operation of the state detection device according to this embodiment will be described next. The state detection device according to this embodiment has the same arrangement as that of the state detection device in the sixth embodiment. Hence, the same reference numerals as in FIG. 46 denote the same components in this embodiment. The state detection device of this embodiment includes a measuring tube 1, first electrodes 2a and 2b, second electrodes 2c and 2d, exciting coil 3, a power supply unit 4, and a state quantifying unit 8a.

The state quantifying unit 8b includes a signal conversion unit 5b which obtains the amplitudes and phases of the first resultant electromotive forces detected by the first electrodes 2a and 2b and the second resultant electromotive forces detected by the electrodes 2c and 2d, obtains the electromotive force differences having the same frequency component of the first and second resultant electromotive forces with the first and second angular frequencies ω0 and ω2, extracts, from the electromotive force differences, the ∂A/∂t components with the first and second angular frequencies ω0 and ω2, and extracts the magnitude or phase of the ratio between the variation factors dependent on the second parameter and frequency from the ratio between the ∂A/∂t components with the first and second angular frequencies ω0 and ω2, a state storage unit 6b (equivalent to the above-described second table) which stores in advance the relationship between the second parameter and the magnitude or phase of the ratio between the variation factors, and a state output unit 7b which obtains the second parameter corresponding to the magnitude or phase of the ratio between the extracted variation factors based on the relationship stored in the state storage unit 6b.

The power supply unit 4b repeats, in a T-sec cycle, the operation of continuing the first excitation state for T1 sec in which the exciting current having the first angular frequency ω0 is supplied to the exciting coil 3, and continuing the second excitation state for T2 sec in which the exciting current having the second angular frequency ω2 is supplied to the exciting coil 3. That is, T=T1+T2.

Figure 52:
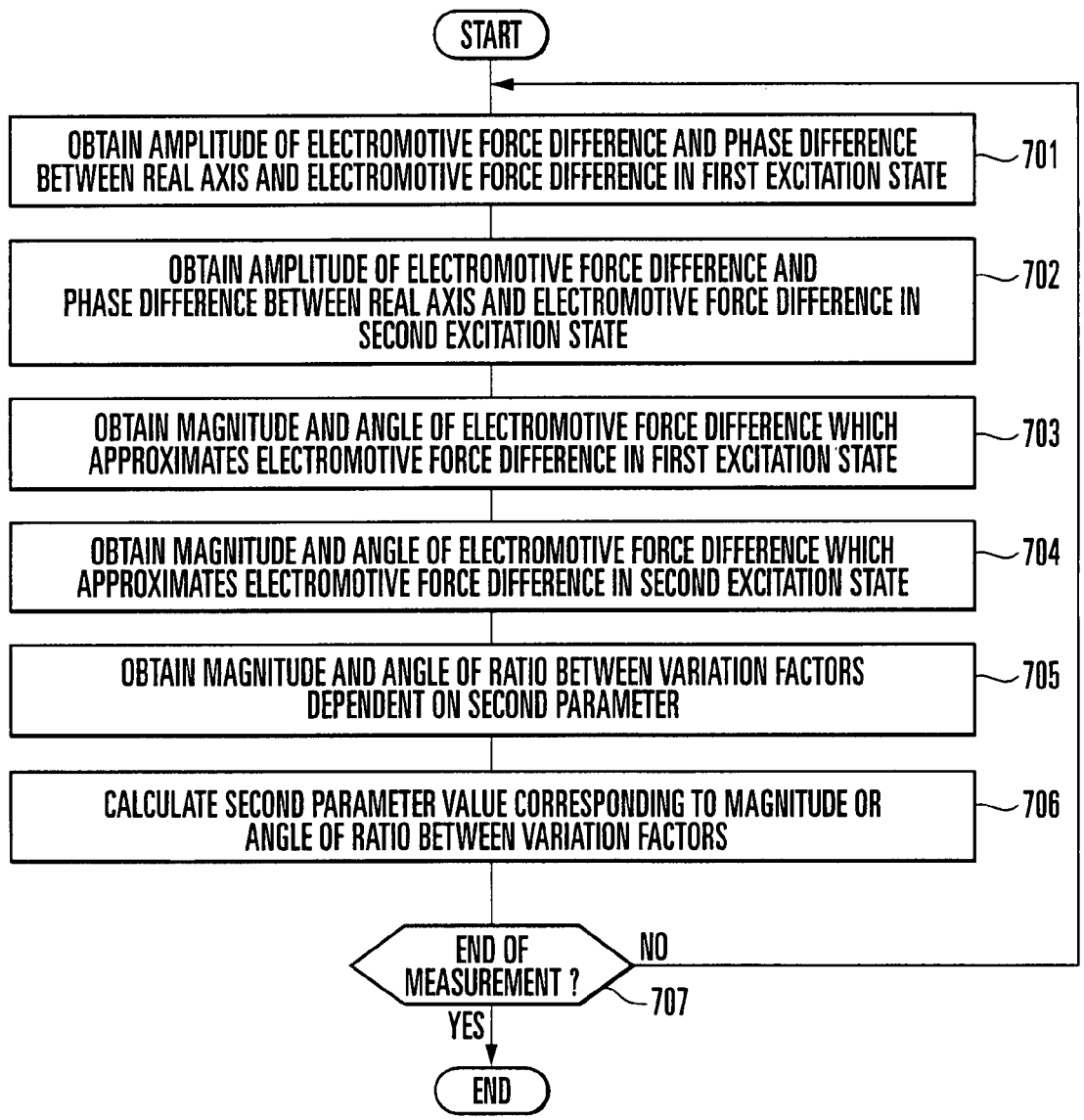
FIG. 52 is a flowchart showing the operation of a state quantifying unit according to the eighth embodiment of the present invention.

FIG. 52 is a flowchart showing the operation of the state quantifying unit 8b according to this embodiment. First of all, the signal conversion unit 5b obtains an amplitude r830d of the difference E830d between the electromotive force with the angular frequency ω0 component of the first inter-electrode electromotive force between the electrodes 2a and 2b and the electromotive force with the angular frequency ω0 component of the second inter-electrode electromotive force between the electrodes 2c and 2d in the first excitation state, and obtains a phase difference φ830d between the real axis and the electromotive force difference E830d by using a phase detector (not shown) (step 701 in FIG. 52).

Subsequently, the signal conversion unit 5b obtains an amplitude r832d of the difference E832d between the electromotive force with the angular frequency ω2 component of the first inter-electrode electromotive force and the electromotive force with the angular frequency ω2 component of the second inter-electrode electromotive force, and obtains a phase difference φ832d between the real axis and the electromotive force difference E832d by using the phase detector (step 702).

Next, the signal conversion unit 5b calculates the magnitude |EdA80| and an angle ∠EdA80 with respect to the real axis of the electromotive force EdA80 which approximates the electromotive force difference E830d according to the following equation (step 703):

$$|EdA80|=r830d \quad (257)$$

$$\angle EdA80=\phi830d \quad (258)$$

The signal conversion unit 5b then calculates the magnitude |EdA82| and an angle ∠EdA82 with respect to the real axis of the electromotive force difference EdA82 which approximates the electromotive force difference E832d according to the following equation (step 704):

$$|EdA82|=r832d \quad (259)$$

$$\angle EdA82=\phi832d \quad (260)$$

The processing in steps 703 and 704 corresponds to the processing of obtaining the ∂A/∂t component, and is equivalent to the calculation of equations (243) and (247).

The signal conversion unit 5b extracts the variation factor Cp80 dependent on the second parameter p8 from the electromotive force difference EdA80, extracts the variation factor Cp82 dependent on the second parameter p8 from the electromotive force difference EdA82, and obtains the magnitude and angle of the ratio Cn8 between the variation factors Cp82 and Cp80 (step 705). The signal conversion unit 5b calculates the magnitude (rk[p8,ω2]/rk[p8,ω0]) of the ratio Cn8 as follows:

$$rk[p8,\omega2]/rk[p8,\omega0]=(|EdA82|/|EdA80|)\cdot(\omega0/\omega2) \quad (261)$$

The signal conversion unit 5b calculates the angle (θ00[p8,ω2]−θ00[p8,ω0]) with respect to the real axis of the ratio Cn8 as follows:

$$\theta00[p8,\omega2]-\theta00[p8,\omega0]=\angle EdA82-\angle EdA80 \quad (262)$$

With the above operation, the processing in step 705 is complete.

The relationship between the second parameter p8 and the magnitude (rk[p8,ω2]/rk[p8,ω0]) of the ratio Cn8 or the relationship between the second parameter p8 and the angle (θ00[p8,ω2]−θ00[p8,ω0]) of the ratio Cn8 is registered in advance in the state storage unit 6b in the form of a mathematical expression or table. In step 706, the state output unit 7b calculates the value of the second parameter p8 corresponding to (rk[p8,ω2]/rk[p8,ω0]) or (θ00[p8,ω2]−θ00[p8,ω0]) by referring to the state storage unit 6b on the basis of the magnitude (rk[p8,ω2]/rk[p8,ω0]) or angle (θ00[p8,ω2]−θ00[p8,ω0]) of the ratio Cn8 calculated by the signal conversion unit 5b (or acquires it from the state storage unit 6b).

The state quantifying unit 8b performs the processing in steps 701 to 706 described above in a cycle T until, for example, the operator designates the end of the measurement (YES in step 707). Note that the processing in steps 702 to 706 is performed in the second excitation state for a duration of T2 sec.

As described above, according to this embodiment, note that when the magnitudes B3 and B4 generated from the exciting coil 3 are equal to each other, the electromotive force differences E830d and E832d can be approximately extracted as the ∂A/∂t components when the exciting angular frequencies are ω0 and ω2, respectively. This embodiment is configured to extract the variation factors Cp80 and Cp82 dependent on the characteristic or state of the fluid or a state in the measuring tube (the second parameter p8) from the approximately extracted two ∂A/∂t components, and obtain the second parameter p8 on the basis of the magnitude or phase of the ratio between the variation factors Cp82 and Cp80. This makes it possible to accurately detect the characteristic or state of the fluid or the state in the measuring tube regardless of the flow velocity of the fluid.

As in the sixth embodiment, the components of the state quantifying unit 8b of this embodiment, except for the detecting unit of the electromotive force differences E830d and E832d, can be implemented by a computer and program. In this embodiment, assume that the exciting current having an angular frequency ω0 is supplied to the exciting coil 3, and E830s represents a sum of the first inter-electrode electromotive force between electrodes 2a and 2b and the second inter-electrode electromotive force between electrodes 2c and 2d. In this case, an inter-electrode electromotive force E830s is obtained by reversing the sign of b4 in equation (239). As a result, the inter-electrode electromotive force E830s can be handled as the v×B component. Therefore, according to this embodiment, the characteristic or state of the fluid or the state in the measuring tube can be detected by using basically the same hardware arrangement as that of an electromagnetic induction type flowmeter.

In this embodiment, it suffices to extract either the magnitude ($rk[p8,\omega2]/rk[p8,\omega0]$) or angle ($\theta00[p8,\omega2]-\theta00[p8,\omega0]$) of the ratio Cn8 between the variation factors. However, the second parameter p8 can be obtained by extracting both the magnitude and angle of the component. In this case, it suffices to select either the magnitude ($rk[p8,\omega2]/rk[p8,\omega0]$) or the angle ($\theta00[p8,\omega2]-\theta00[p8,\omega0]$) which has a higher sensitivity and obtain the second parameter p8 on the basis of the selected magnitude or angle. This makes it possible to improve the detection sensitivity.

In addition, this embodiment has exemplified the case wherein the exciting frequency is switched to ω0 or ω2. However, performing excitation using exciting currents containing components with the angular frequencies ω0 and ω2 makes it unnecessary to switch the exciting frequencies. This can calculate the second parameter p8 at higher speed. For example, it suffices to use the magnetic field represented by equations (225) and (226) instead of equations (41) and (42).

Ninth Embodiment

The ninth embodiment of the present invention will be described next. A state detection device according to this embodiment includes one exciting coil and two pairs of electrodes, and has the same arrangement as that of the state detection device shown in FIG. 13 except for the signal processing system. The principle of this embodiment will therefore be described by using reference numerals in FIG. 13. This embodiment uses the second extraction method as a method of extracting a ∂A/∂t component from a resultant vector, and obtains the second parameter for a variation factor having a frequency characteristic. In this embodiment, two second parameter values are obtained. Of the two second parameters, one is the third parameter, and the other is the fourth parameter.

Assume that the exciting current having an angular frequency ω0 is supplied to an exciting coil 3, the third parameter is p9, and the fourth parameter is q9. In this case, the difference E930d between the first inter-electrode electromotive force between electrodes 2a and 2b and the second inter-electrode electromotive force between electrodes 2c and 2d is represented by the following equation according to equations (54), (85), and (86).

$$E930d = rk[p9, q9, \omega0] \cdot \exp\{j \cdot (\theta3 + \theta00[p9, q9, \omega0])\} \cdot \\ \exp(j \cdot \pi/2) \cdot (b3 + b4 \cdot \exp(j \cdot \Delta\theta4)) \cdot \omega0 + \\ \gamma \cdot \exp(j \cdot \Delta\theta01) \cdot \{b3 - b4 \cdot \exp(j \cdot \Delta\theta4)\} \cdot V] \quad (263)$$

From equations (228) and (229), equations (240) and (241) hold in equation (263). The following expressions represent an electromotive force difference EdA90 which approximates the electromotive force difference E930d in equation (263) by using the condition of expression (241).

$$EdA90 \approx E930d \quad (264)$$

$$EdA90 = rk[p9, q9, \omega0] \cdot \exp\{j \cdot \theta00[p9, q9, \omega0]\} \cdot \exp\{j \cdot (\pi/2 + \theta3)\} \cdot \{b3 + b4 \cdot \exp(j \cdot \Delta\theta4)\} \cdot \omega0 \quad (265)$$

Assume that the exciting current having an angular frequency ω2 is supplied to the exciting coil 3, the third parameter is p9, and the fourth parameter is q9. In this case, the difference E932d between the first inter-electrode electromotive force between the electrodes 2a and 2b and the second inter-electrode electromotive force between the electrodes 2c and 2d is represented by the following equation according to equations (54), (88) and (89).

$$E932d = rk[p9, q9, \omega2] \cdot \exp\{j \cdot (\theta3 + \theta00[p9, q9, \omega2])\} \cdot \\ [\exp(j \cdot \pi/2) \cdot \{b3 + b4 \cdot \exp(j \cdot \Delta\theta4)\} \cdot \omega2 + \\ \gamma \cdot \exp(j \cdot \Delta\theta01) \cdot \{b3 - b4 \cdot \exp(j \cdot \Delta\theta4)\} \cdot V] \quad (266)$$

Since ω2>γ·V holds, equation (245) holds for the electromotive force difference E932d given by equation (266) in consideration of the condition represented by equation (240). The following expressions represent the electromotive force difference EdA92 which approximates the electromotive force difference E932d in equation (266) by using the condition of expression (245).

$$EdA92 \approx E932d \quad (267)$$

$$EdA92 = rk[p9, q9, \omega2] \cdot \exp\{j \cdot \theta00[p9, q9, \omega2]\} \cdot \\ \exp(j \cdot (\pi/2 + \theta3)) \cdot \{b3 + b4 \cdot \exp(j \cdot \Delta\theta4)\} \cdot \omega2 \quad (268)$$

In equations (265) and (268), the ∂A/∂t component in the resultant vector can be extracted by using the difference between the inter-electrode electromotive forces. Equations (265) and (268) are irrelevant to the magnitude V of the flow velocity, and hence are only the component generated by ∂A/∂t. The fluid state except for the flow velocity, and the state in the measuring tube can be measured by using this electromotive force difference.

When a variation factor dependent on the third and fourth parameters is Cpq90 in equation (265), Cpq90=rk[p9,q9,ω0]·exp(j·θ00[p9,q9,ω0]) holds, and the remaining portion is a constant which is provided at the time of calibration. The variation factor Cpq90 is represented by equation (265).

$$Cpq90 = EdA90 / [\exp\{j \cdot (\pi/2 + \theta 3)\} \cdot \{b3 + b4 \cdot \exp(j \cdot \Delta \theta 4)\} \cdot \omega 0] \quad (269)$$

When a variation factor dependent on the third and fourth parameters is Cpq92 in equation (268), Cpq92=rk[p9,q9,ω2]·exp(j·θ00[p9,q9,ω2]) holds, and the remaining portion is a constant which is provided at the time of calibration. The variation factor Cpq92 is represented by equation (268).

$$Cpq92 = EdA92 / [\exp\{j \cdot (\pi/2 + \theta 3)\} \cdot \{b3 + b4 \cdot \exp(j \cdot \Delta \theta 4)\} \cdot \omega 2] \quad (270)$$

Letting m3b and θ3b be the magnitude and angle of [exp{j·(π/2+θ3)}·{b3+b4·exp(j·Δθ4)}] in equations (269) and (270), m3b and θ3b are represented by equations (213) and (214). Upon applying equations (213) and (214) to equation (269), a magnitude rk[p9,q9,ω0] of the variation factor Cpq90 and an angle θ00[p9,q9,ω0] thereof from the real axis are represented by $$rk[p9,q9,\omega 0]=|EdA90|/(m3b \cdot \omega 0) \quad (271)$$

$$\theta 00[p9,q9,\omega 0]=\angle EdA90 - \theta 3b \quad (272)$$

Upon applying equations (120) and (121) to equation (270), a magnitude rk[p9,q9,ω2] of the variation factor Cpq92 and an angle θ00[p9,q9,ω2] thereof from the real axis are represented by $$rk[p9,q9,\omega 2]=|EdA92|/(m3b \cdot \omega 2) \quad (273)$$

$$\theta 00[p9,q9,\omega 2]=\angle EdA92 - \theta 3b \quad (274)$$

The parameters p9 and q9 can be obtained from the relationship between the parameters p9 and q9 and rk[p9,q9,ω0] and rk[p9,q9,ω2], which is checked in advance by measurement or the like at the time of calibration, or the relationship between the parameters p9 and q9, and θ00[p9,q9,ω0] and θ00[p9,q9,ω2].

The specific arrangement and operation of the state detection device according to this embodiment will be described next. The state detection device according to this embodiment has the same arrangement as that of the state detection device in the sixth embodiment. Hence, the same reference numerals as in FIG. 46 denote the same components in this embodiment. The state detection device of this embodiment includes a measuring tube 1, first electrodes 2a and 2b, second electrodes 2c and 2d, an exciting coil 3, a power supply unit 4, and a state quantifying unit 8b.

The state quantifying unit 8b includes a signal conversion unit 5b which obtains the amplitudes and phases of the first resultant electromotive force detected by the first electrodes 2a and 2b and the second resultant electromotive force detected by the second electrodes 2c and 2d, obtains the electromotive force differences having the same frequency component of the first and second resultant electromotive forces with the first and second angular frequencies ω0 and ω2 based on the amplitudes and phases, extracts, from the electromotive force differences, ∂A/∂t components with the plurality of frequency components, and extracts, from the extracted ∂A/∂t components, the magnitude or phase of the variation factors dependent on the plurality of second parameters and frequencies, a state storage unit 6b (equivalent to the above-described third table) which stores in advance the relationship between the plurality of second parameters and the magnitude or phase of the variation factors with the plurality of frequency components, and a state output unit 7b which obtains the plurality of second parameters corresponding to the magnitude or phase of the extracted variation factors based on the relationship stored in the state storage unit 6b.

Figure 53:
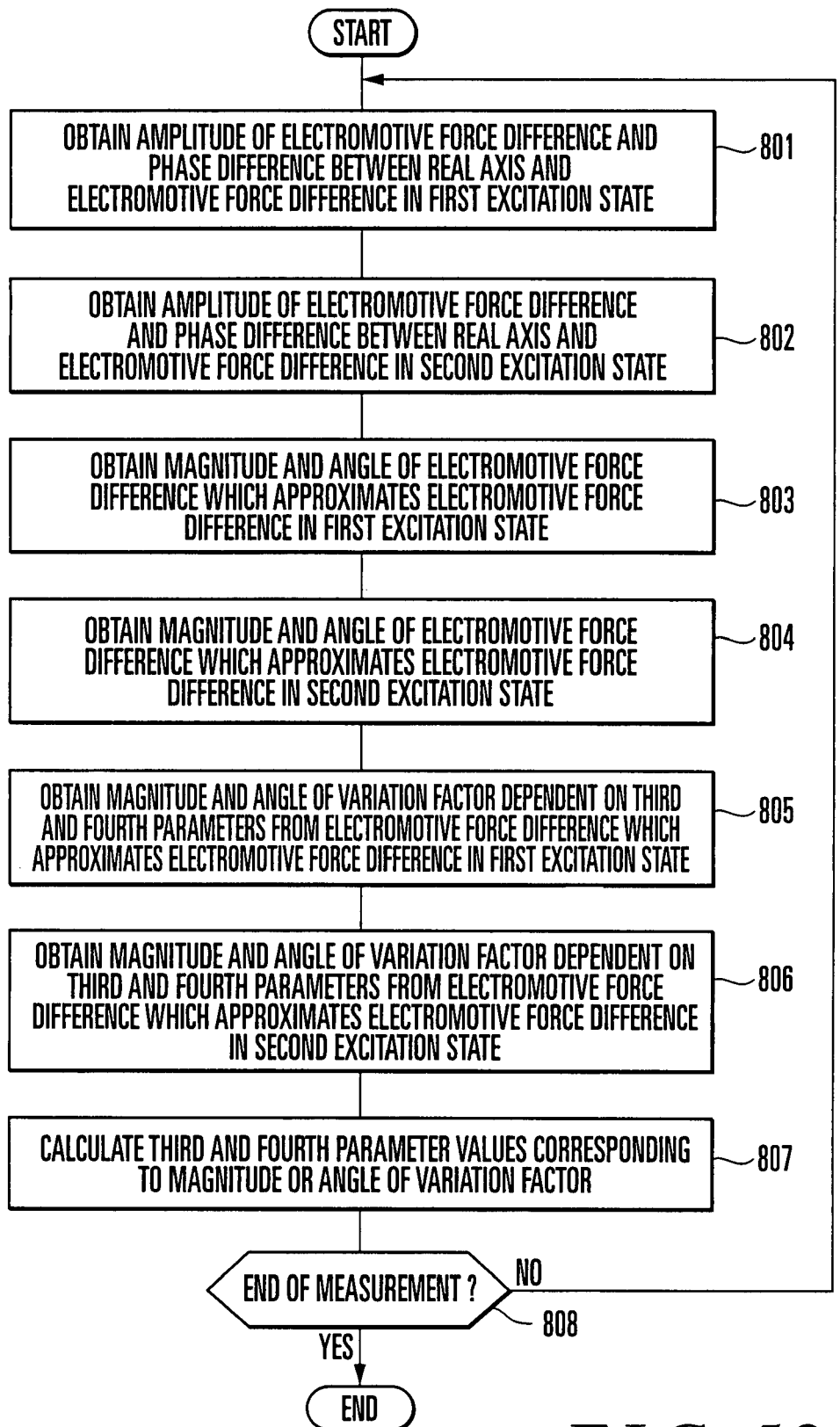
FIG. 53 is a flowchart showing the operation of a state quantifying unit according to the ninth embodiment of the present invention.

The operation of the power supply unit 4b is the same as that in the eighth embodiment. FIG. 53 is a flowchart showing the operation of the state quantifying unit 8b according to this embodiment. First of all, the signal conversion unit 5b obtains an amplitude r930d of the difference between the electromotive force with the angular frequency ω0 component of the first inter-electrode electromotive force between the electrodes 2a and 2b and the electromotive force with the angular frequency ω0 component of the second inter-electrode electromotive force between the electrodes 2c and 2d in the first excitation state, and obtains a phase difference φ930d between the real axis and the electromotive force difference E930d by using a phase detector (not shown) (step 801 in FIG. 53).

Subsequently, the signal conversion unit 5b obtains an amplitude r932d of the difference between the electromotive force with the angular frequency ω2 of the inter-electrode electromotive force and the electromotive force with the frequency ω2 of the second inter-electrode electromotive force in the second excitation state wherein the exciting angular frequency is ω2, and obtains a phase difference φ932d between the real axis and the electromotive force difference E932d by using the phase detector (step 802).

Next, the signal conversion unit 5b calculates the magnitude |EdA90| and an angle ∠EdA90 with respect to the real axis of the electromotive force EdA90 which approximates the electromotive force difference E930d according to the following equation (step 803):

$$|EdA90|=r930d \quad (275)$$

$$\angle EdA90=\phi 930d \quad (276)$$

The signal conversion unit 5b then calculates the magnitude |EdA92| and an angle ∠EdA92 with respect to the real axis of the electromotive force difference EdA92 which approximates the electromotive force difference E932d according to the following equation (step 804):

$$|EdA92|=r932d \quad (277)$$

$$\angle EdA92=\phi 932d \quad (278)$$

The processing in steps 803 and 804 corresponds to the processing of obtaining the ∂A/∂t component, and is equivalent to the calculation of equations (265) and (268).

The signal conversion unit 5b calculates, from the electromotive force difference EdA90, the magnitude rk[p9,q9,ω0] of the variation factor Cpq90 dependent on the third and fourth parameters p9 and q9 and the angle θ00[p9,q9,ω0] with respect to the real axis as follows (step 805):

$$rk[p9,q9,\omega 0]=|EdA90|/(m3b \cdot \omega 0) \quad (279)$$

$$\theta 00[p9,q9,\omega 0]=\angle EdA90 - \theta 3b \quad (280)$$

The signal conversion unit 5b also calculates, from the electromotive force difference EdA92, the magnitude rk[p9,q9,ω2] of the variation factor Cpq92 dependent on the third and fourth parameters p9 and q9 and the angle θ00[p9,q9,ω2] with respect to the real axis as follows (step 806):

$$rk[p9,q9,\omega 2]=|EdA92|/(m3b \cdot \omega 2) \quad (281)$$

$$\theta 00[p9,q9,\omega 2]=\angle EdA92 - \theta 3b \quad (282)$$

Note that m3b and θ3b are constants which can be obtained in advance by calibration or the like.

The relationship between the third and fourth parameters p9 and q9 and the magnitudes rk[p9,q9,ω0] and rk[p9,q9,ω2] of the variation factors Cpq90 and Cpq92 or the relationship between the parameters p9 and q9 and the angles θ00[p9,q9,ω0] and θ00[p9,q9,ω2] of the variation factors Cpq90 and Cpq92 is registered in advance in the state storage unit 6b in the form of a mathematical expression or table.

The state output unit 7b calculates the values of the third and fourth parameters p9 and q9 corresponding to the magnitudes rk[p9,q9,ω0] and rk[p9,q9,ω2]) or angles θ00[p9,q9,ω0] and θ00[p9,q9,ω2] by referring to the state storage unit 6b on the basis of the magnitudes rk[p9,q9,ω0] and rk[p9,q9,ω2]) or angles θ00[p9,q9,ω0] and θ00[p9,q9,ω2]) of the variation factors Cpq90 and Cpq92 calculated by the signal conversion unit 5b (step 807).

The state quantifying unit 8b performs the processing in steps 801 to 807 described above in a cycle T until, for example, the operator designates the end of the measurement (YES in step 808). Note that the processing in steps 802 to 807 is performed in the second excitation state for a duration of T2 sec.

As described above, according to this embodiment, note that when the magnitudes B3 and B4 generated from the exciting coil 3 are equal to each other, the electromotive force differences E930d and E932d can be approximately extracted as the ∂A/∂t components when the exciting angular frequencies of the electromotive force differences E930d and E932d are ω0 and ω2, respectively. This embodiment is configured to extract the variation factors Cp90 and Cp92 dependent on the characteristic or state of the fluid or a state in the measuring tube (the third and fourth parameters p9 and q9) from the approximately extracted two ∂A/∂t components, and obtain the third and fourth parameters p9 and q9 on the basis of the magnitude or phase of the variation factors Cp90 and Cp92. This makes it possible to accurately detect the characteristic or state of the fluid or the state in the measuring tube regardless of the flow velocity of the fluid.

As in the sixth embodiment, the components of the state quantifying unit 8b of this embodiment, except for the detecting unit of the electromotive force differences E930d and E932d, can be implemented by a computer and program. In this embodiment, assume that the exciting current having an angular frequency ω0 is supplied to the exciting coil 3, the third parameter is p9, and the fourth parameter is q9. In this case, when E930s represents a sum of the first inter-electrode electromotive force between the electrodes 2a and 2b and the second inter-electrode electromotive force between the electrodes 2c and 2d, the inter-electrode electromotive force E930s is obtained by reversing the sign of b4 in equation (263). As a result, the inter-electrode electromotive force E930s can be handled as the v×B component. Therefore, according to this embodiment, the characteristic or state of the fluid or the state in the measuring tube can be detected by using basically the same hardware arrangement as that of an electromagnetic induction type flowmeter.

In this embodiment, it suffices to extract either the magnitudes rk[p9,q9,ω0] and rk[p9,q9,ω2]) or angles θ00[p9,q9,ω0] and θ00[p9,q9,ω2] of the variation factors Cpq90 and Cpq92. However, the third and fourth parameters p9 and q9 can be obtained by extracting both the magnitude and angle of the component. In this case, it suffices to select either the magnitudes rk[p9,q9,ω0] and rk[p9,q9,ω2] or the angles θ00[p9,q9,ω0] and θ00[p9,q9,ω2] which has a higher sensitivity and obtain the third and fourth parameters p9 and q9 on the basis of the selected magnitude or angle. This makes it possible to improve the detection sensitivity.

In addition, this embodiment has exemplified the case wherein the exciting frequency is switched to ω0 or ω2. However, performing excitation using exciting currents containing components with the angular frequencies ω0 and ω2 makes it unnecessary to switch the exciting frequencies. This can calculate the parameters p9 and q9 at higher speed. For example, it suffices to use the magnetic field represented by equations (225) and (226) instead of equations (41) and (42).

Furthermore, each of the first to ninth embodiments uses the pair of electrodes 2a and 2b as the first electrodes, and the pair of electrodes 2c and 2d as the second electrodes. However, the present invention is not limited to this, and may use one each of the first and second electrodes. If only one electrode is to be used, since a ground ring or a ground electrode for grounding the potential of a fluid to be measured is provided on the measuring tube 1, it suffices to detect an electromotive force (a potential difference from the ground potential) generated at the single electrode by using the signal conversion unit 5, 5a, or 5b. When a pair of electrodes are to be used, an electrode axis is defined as a straight line connecting the pair of electrodes. Assume that only one electrode is to be used. In this case, assuming that a virtual electrode is placed at a position to face the real electrode through the measuring tube axis PAX on the plane PLN including the single real electrode, the electrode axis is defined as a straight line connecting the real electrode and the virtual electrode.

INDUSTRIAL APPLICABILITY

The present invention can be applied to a state detection device which detects a characteristic or state of a fluid or a state in a measuring tube through which the fluid flows.

The invention claimed is:

1. A state detection device characterized by comprising:
a measuring tube through which a fluid flows;
an exciting unit which applies, to the fluid, a time-changing magnetic field asymmetrical to a first plane perpendicular to an axial direction of said measuring tube;
an electrode which is placed on the first plane in said measuring tube to detect a resultant electromotive force of an electromotive force based on a ∂A/∂t component (A: vector potential, t: time) irrelevant to a flow velocity of the fluid and an electromotive force based on a v×B component (v: flow velocity, B: magnetic flux density) originating from the flow velocity of the fluid, the resultant electromotive force being generated by the magnetic field applied to the fluid and a flow of the fluid; and
a state quantifying unit which extracts the ∂A/∂t component from the resultant electromotive force detected by said electrode, extracts, from the ∂A/∂t component, a variation factor dependent on a parameter to be detected, and quantifies the parameter on the basis of the variation factor,
wherein the parameter is at least one of a characteristic and state of the fluid and a state in said measuring tube.

2. A state detection device according to claim 1, characterized in that
said state quantifying unit comprises
a signal conversion unit which extracts the ∂A/∂t component from the resultant electromotive force detected by said electrode, and extracts the variation factor dependent on the parameter from the ∂A/∂t component,
a state storage unit which stores in advance a relationship between the parameter and the variation factor dependent on the parameter, and a state output unit which obtains the parameter corresponding to the extracted variation factor, on the basis of the relationship stored in said state storage unit.

3. A state detection device according to claim 2, characterized in that
said exciting unit applies magnetic fields to the fluid to provide a plurality of exciting frequencies at one of a simultaneous timing and an alternative timing, and
said signal conversion unit extracts the $\partial A/\partial t$ component by obtaining amplitudes and phases of a plurality of frequency components, of the resultant electromotive force detected by said electrode, which are obtained at one of a simultaneous timing and an alternative timing.

4. A state detection device according to claim 3, characterized in that
said exciting unit comprises an exciting coil placed at a position spaced apart by an offset from the first plane, and a power supply unit which supplies an exciting current to the exciting coil to provide two different exciting frequencies including a first frequency and a second frequency at one of a simultaneous timing and an alternative timing,
said signal conversion unit obtains amplitudes and phases of two frequency components with the first frequency and the second frequency of the resultant electromotive force detected by said electrode, extracts, as a $\partial A/\partial t$ component, an electromotive force difference between the two frequency components on the basis of the amplitudes and the phases, and extracts, from the $\partial A/\partial t$ component, one of a magnitude and phase of the variation factor dependent on the parameter but independent of the frequency, and
said state storage unit stores in advance a relationship between the parameter and one of the magnitude and phase of the variation factor dependent on the parameter.

5. A state detection device according to claim 3, characterized in that
said exciting unit comprises a first exciting coil placed at a position spaced apart by a first offset from the first plane, a second exciting coil placed at a position spaced apart by a second offset from the first plane so as to face the first exciting coil though the first plane, and a power supply unit which supplies an exciting current to the first exciting coil and the second exciting coil to provide two different exciting frequencies including a first frequency and a second frequency at one of a simultaneous timing and an alternative timing,
said signal conversion unit obtains amplitudes and phases of two frequency components with the first frequency and the second frequency of the resultant electromotive force detected by said electrode, extracts, as the $\partial A/\partial t$ component, an electromotive force difference between the two frequency components on the basis of the amplitudes and the phases, and extracts, from the $\partial A/\partial t$ component, one of a magnitude and phase of the variation factor dependent on the parameter but independent of the frequency, and
said state storage unit stores in advance a relationship between the parameter and one of the magnitude and phase of the variation factor dependent on the parameter.

6. A state detection device according to claim 3, characterized in that
said exciting unit comprises an exciting coil which applies a magnetic field to the fluid, and a power supply unit which supplies an exciting current to the exciting coil to provide two different exciting frequencies including a first frequency and a second frequency at one of a simultaneous timing and an alternative timing,
said electrode comprises a first electrode placed at a position spaced apart by a first offset from a second plane which includes an axis of the exciting coil and is perpendicular to an axial direction of said measuring tube, and a second electrode placed at a position spaced apart by a second offset from the second plane so as to face the first electrode through the second plane,
said signal conversion unit obtains an amplitude and phase of each of a first resultant electromotive force detected by the first electrode and a second resultant electromotive force detected by the second electrode, obtains electromotive force differences having a same frequency component of the first resultant electromotive force and the second resultant electromotive force at the first frequency and the second frequency on the basis of the amplitude and the phase, extracts, as the $\partial A/\partial t$ component, a difference between the electromotive force difference at the first frequency and the electromotive force difference at the second frequency, and extracts, from the $\partial A/\partial t$ component, one of a magnitude and phase of the variation factor dependent on the parameter but independent of the frequency, and
said state storage unit stores in advance a relationship between the parameter and one of the magnitude and phase of the variation factor dependent on the parameter.

7. A state detection device according to claim 3, characterized in that
said exciting unit comprises an exciting coil which applies a magnetic field to the fluid, and a power supply unit which supplies an exciting current to the exciting coil to provide two different exciting frequencies including a first frequency and a second frequency at one of a simultaneous timing and an alternative timing,
said electrode comprises a first electrode placed at a position spaced apart by a first offset from a second plane which includes an axis of the exciting coil and is perpendicular to an axial direction of said measuring tube, and a second electrode placed at a position spaced apart by a second offset from the second plane so as to face the first electrode through the second plane,
said signal conversion unit obtains an amplitude and phase of each of a first resultant electromotive force detected by the first electrode and a second resultant electromotive force detected by the second electrode, obtains electromotive force sums having a same frequency component of the first resultant electromotive force and the second resultant electromotive force at the first frequency and the second frequency on the basis of the amplitude and the phase, extracts, as the $\partial A/\partial t$ component, a difference between the electromotive force sum at the first frequency and the electromotive force sum at the second frequency, and extracts, from the $\partial A/\partial t$ component, one of a magnitude and phase of the variation factor dependent on the parameter but independent of the frequency, and
said state storage unit stores in advance a relationship between the parameter and one of the magnitude and phase of the variation factor dependent on the parameter.

8. A state detection device according to claim 2, characterized in that
said exciting unit comprises a first exciting coil placed at a position spaced apart by a first offset from the first plane, a second exciting coil placed at a position spaced apart by a second offset from the first plane so as to face the first exciting coil through the first plane, and a power supply unit which supplies exciting currents with a phase difference to the first exciting coil and the second exciting coil, and said signal conversion unit obtains an amplitude and phase of the resultant electromotive force detected by said electrode to extract the ∂A/∂t component.

9. A state detection device according to claim 8, characterized in that said signal conversion unit obtains the amplitude and phase of the resultant electromotive force detected by said electrode to extract the ∂A/∂t component, and extracts, from the ∂A/∂t component, one of a magnitude and phase of the variation factor dependent on the parameter but independent of the frequency, and said state storage unit stores in advance a relationship between the parameter and one of the magnitude and phase of the variation factor dependent on the parameter.

10. A state detection device according to claim 8, characterized in that the power supply unit supplies, to the first exciting coil and the second exciting coil, the exciting currents with a phase difference to provide at least two exciting frequencies at one of a simultaneous timing and an alternative timing, said signal conversion unit extracts a ∂A/∂t component with the first frequency component and a ∂A/∂t component with the second frequency component by obtaining the amplitudes and phases of two frequency components with the first frequency and the second frequency of the resultant electromotive force detected by said electrode, and extracts one of a magnitude and phase of a ratio between variation factors dependent on the parameter and the frequency, on the basis of a ratio between the ∂A/∂t component with the first frequency component and the ∂A/∂t component with the second frequency component, and the state storage unit stores in advance a relationship between the parameter and one of the magnitude and phase of the ratio between the variation factors.

11. A state detection device according to claim 8, characterized in that the power supply unit supplies, to the first exciting coil and the second exciting coil, the exciting currents with a phase difference to provide a plurality of exciting frequencies at one of a simultaneous timing and an alternative timing, said signal conversion unit extracts a ∂A/∂t component for each of a plurality of frequency components by obtaining the amplitudes and phases of the plurality of frequency components of the resultant electromotive force detected by said electrode, and extracts, from each of the extracted ∂A/∂t components, one of magnitudes and phases of variation factors dependent on a plurality of parameters and frequencies, the state storage unit stores in advance a relationship between the plurality of parameters and one of the magnitude and phase of the variation factor for each of the plurality of frequency components, and the state output unit calculates the plurality of parameters corresponding to one of the magnitude and phase of the extracted variation factor on the basis of the relationship stored in the state storage unit.

12. A state detection device according to claim 2, characterized in that said exciting unit comprises an exciting coil which applies a magnetic field to the fluid, and a power supply unit which supplies an exciting current to the exciting coil, said electrode comprises a first electrode placed at a position spaced apart by a first offset from a second plane which includes an axis of the exciting coil and is perpendicular to an axial direction of said measuring tube, and a second electrode placed at a position spaced apart by a second offset from the second plane so as to face the first electrode through the second plane, and said signal conversion unit obtains an amplitude and phase of each of a first resultant electromotive force detected by the first electrode and a second resultant electromotive force detected by the second electrode, and extracts the ∂A/∂t component from an electromotive force difference between the first resultant electromotive force and the second resultant electromotive force on the basis of the amplitude and the phase.

13. A state detection device according to claim 12, characterized in that said signal conversion unit obtains the amplitude and phase of each of the first resultant electromotive force detected by the first electrode and the second resultant electromotive force detected by the second electrode, extracts the ∂A/∂t component from an electromotive force difference between the first resultant electromotive force and the second resultant electromotive force on the basis of the amplitudes and the phases, and extracts, from the ∂A/∂t component, one of the magnitude and phase of the variation factor dependent on the parameter but independent of the frequency, and the state storage unit stores in advance a relationship between the parameter and one of the magnitude and phase of the variation factor dependent on the parameter.

14. A state detection device according to claim 12, characterized in that the power supply unit supplies the exciting current to the exciting coil to provide the different exciting frequencies including the first frequency and the second frequency at one of a simultaneous timing and an alternative timing, said signal conversion unit obtains an amplitude and phase of each of a first resultant electromotive force detected by the first electrode and a second resultant electromotive force detected by the second electrode, obtains electromotive force differences having a same frequency component of the first resultant electromotive force and the second resultant electromotive force at the first frequency and the second frequency on the basis of the amplitude and the phase, extracts a ∂A/∂t component with the first frequency component and a ∂A/∂t component with the second frequency component from the electromotive force difference, and extracts, from the ratio between the ∂A/∂t component with the first frequency component and the ∂A/∂t component with the second frequency component, one of the magnitude and phase of the ratio between the variation factors dependent on the parameter and the frequency, and the state storage unit stores in advance a relationship between the parameter and one of the magnitude and phase of the ratio between the variation factors.

15. A state detection device according to claim 12, characterized in that the power supply unit supplies the exciting current to the exciting coil to provide a plurality of exciting frequencies at one of a simultaneous timing and an alternative timing, said signal conversion unit obtains an amplitude and phase of each of a first resultant electromotive force detected by the first electrode and a second resultant electromotive force detected by the second electrode, obtains electromotive force differences having a same frequency component of the first resultant electromotive force and the second resultant electromotive force at a plurality of frequency components on the basis of the amplitude and the phase, extracts the $\partial A/\partial t$ components with the plurality of frequency components from the electromotive force difference, and extracts, from the extracted $\partial A/\partial t$ component, one of the magnitude and phase of the ratio between the variation factors dependent on a plurality of parameters and frequencies, said state storage unit stores in advance the relationship between the plurality of parameters and one of the magnitude and phase of the variation factor with each of the plurality of frequency components, and said state output unit calculates the plurality of parameters corresponding to one of the magnitude and phase of the extracted variation factor on the basis of the relationship stored in said state storage unit.

* * * * *